US006632399B1

United States Patent
Kellogg et al.

(10) Patent No.: US 6,632,399 B1
(45) Date of Patent: Oct. 14, 2003

(54) DEVICES AND METHODS FOR USING CENTRIPETAL ACCELERATION TO DRIVE FLUID MOVEMENT IN A MICROFLUIDICS SYSTEM FOR PERFORMING BIOLOGICAL FLUID ASSAYS

(75) Inventors: Gregory Kellogg, Somerville, MA (US); Stephen G. Kieffer-Higgins, Dorchester, MA (US); Mona D. Jensen, Hampstead, NH (US); Shari Ommert, Medford, MA (US); Mikayla Kob, Allston, MA (US); Andrea Pierce, Hollis, NH (US); Keith Morneau, Boston, MA (US); Hsin Chiang Lin, Cambridge, MA (US)

(73) Assignee: Tecan Trading AG, Baar (CH)

( * ) Notice: Subject to any disclaimer, the term of this patent is extended or adjusted under 35 U.S.C. 154(b) by 0 days.

(21) Appl. No.: 09/315,114

(22) Filed: May 19, 1999

Related U.S. Application Data

(63) Continuation-in-part of application No. 09/083,678, filed on May 22, 1998, now Pat. No. 6,063,589.

(51) Int. Cl.[7] .................................................. G01N 1/28
(52) U.S. Cl. .......................... 422/72; 422/101; 436/45; 436/177
(58) Field of Search ..................... 422/72, 101; 436/45, 436/177

(56) References Cited

U.S. PATENT DOCUMENTS

| | | |
|---|---|---|
| 3,679,367 A | 7/1972 | Negersmith et al. |
| 3,713,062 A | 1/1973 | Butler et al. |
| 3,952,116 A | 4/1976 | Trenkler et al. |
| 4,030,834 A | 6/1977 | Bauer et al. |
| 4,154,793 A | 5/1979 | Guigan |
| 4,258,740 A | 3/1981 | Kaartinen et al. |
| 4,381,291 A | 4/1983 | Ekins |
| 4,515,889 A | 5/1985 | Klose et al. |
| 4,676,952 A | 6/1987 | Edelmann |
| 4,690,899 A | * 9/1987 | Klose et al. |
| 4,722,853 A | 2/1988 | Batliwalla et al. |
| 4,729,862 A | 3/1988 | Salatiello et al. |
| 4,745,072 A | 5/1988 | Ekins |

(List continued on next page.)

FOREIGN PATENT DOCUMENTS

| | | |
|---|---|---|
| DE | 4410224 | 9/1995 |
| EP | 322657 | 7/1989 |
| EP | 417305 | 3/1991 |
| EP | 305210 | 12/1993 |
| EP | 616218 | 9/1994 |
| EP | 0637367 B1 | 12/1997 |
| WO | WO 93/22053 | 11/1993 |
| WO | WO 93/22058 | 11/1993 |
| WO | WO 95/33986 | 12/1995 |

OTHER PUBLICATIONS

Anderson, (1968), *Anal. Biochem.*, 28: 545–562.
Renoe et al., (1974), Clin. Chem., 20/8: 955–960.
Burtis et al., (1974), Clin. Chem., 20/8: 932–941.

(List continued on next page.)

*Primary Examiner*—Jan Ludlow
(74) *Attorney, Agent, or Firm*—McDonnell Boehnen Hulbert & Berghoff

(57) ABSTRACT

This invention provides methods and apparatus for performing microanalytic and microsynthetic analyses and procedures. Specifically, the invention provides a microsystem platform for use with a micromanipulation device to manipulate the platform by rotation, thereby utilizing the centripetal force resulting from rotation of the platform to motivate fluid movement through microchannels embedded in the microplatform. The microsystem platforms of the invention are also provided having microfluidics components, resistive heating elements, temperature sensing elements, mixing structures, capillary and sacrificial valves, and methods for using these microsystems platforms for performing biological, enzymatic, immunological and chemical assays.

16 Claims, 38 Drawing Sheets

U.S. PATENT DOCUMENTS

| | | | |
|---|---|---|---|
| 4,872,821 A | | 10/1989 | Weiss |
| 4,940,527 A | | 7/1990 | Kazlauskas et al. |
| 4,999,304 A | * | 3/1991 | Robertson |
| 5,006,749 A | | 4/1991 | White |
| 5,061,381 A | | 10/1991 | Burd |
| 5,122,284 A | | 6/1992 | Braynin et al. |
| 5,160,702 A | | 11/1992 | Kopf-Sill et al. |
| 5,171,533 A | | 12/1992 | Fine et al. |
| 5,171,695 A | | 12/1992 | Ekins |
| 5,173,193 A | | 12/1992 | Schembri |
| 5,173,262 A | | 12/1992 | Burtis et al. |
| 5,186,844 A | | 2/1993 | Burd et al. |
| 5,242,606 A | | 9/1993 | Braynin et al. |
| 5,242,803 A | | 9/1993 | Burtis et al. |
| 5,252,294 A | | 10/1993 | Kroy et al. |
| 5,275,016 A | | 1/1994 | Chatterjee et al. |
| 5,304,348 A | | 4/1994 | Burd et al. |
| 5,304,487 A | | 4/1994 | Wilding et al. |
| 5,368,704 A | | 11/1994 | Madou et al. |
| 5,403,415 A | | 4/1995 | Schembri |
| 5,409,665 A | | 4/1995 | Burd |
| 5,413,732 A | | 5/1995 | Buhl et al. |
| 5,426,032 A | | 6/1995 | Phillips et al. |
| 5,432,009 A | | 7/1995 | Tabata et al. |
| 5,457,053 A | | 10/1995 | Burd et al. |
| 5,472,603 A | | 12/1995 | Schembri |
| 5,478,750 A | | 12/1995 | Bernstein et al. |
| 5,496,520 A | | 3/1996 | Kelton et al. |
| 5,518,930 A | | 5/1996 | Burd |
| 5,590,052 A | | 12/1996 | Kopf-Sill et al. |
| 5,591,643 A | | 1/1997 | Schembri |
| 5,599,411 A | | 2/1997 | Schembri |
| 5,622,819 A | | 4/1997 | Herman |
| 5,624,597 A | | 4/1997 | Buhl et al. |
| 5,639,428 A | | 6/1997 | Cottingham |
| 5,693,233 A | | 12/1997 | Schembri |
| 5,821,116 A | | 10/1998 | Herman |
| 6,319,468 B1 | * | 11/2001 | Sheppard, Jr. et al. |

OTHER PUBLICATIONS

Fritsche et al., (1975), Clin Biochem., 8:240–246.
Burtis et al., (1975), Clin. Chem., 21/9: 1225–1233.
Hadjiioannou et al., (1976), Clin. Chem., 22/6: 802–805.
Lee et al., (1978), Clin. Chem., 24/8: 1361–1365.
Cho et al., (1982), Clin. Chem., 28/9: 1961–1965.
Bertrand et al., (1982), Clinica Chimica Acta, 119: 275–284.
Schembri et al., (1992), Clin. Chem., 38/9: 1665–1670.
Columbus et al., (1987), Clin. Chem., 33/9: 1531–1537.
Ekins et all., (1992), Ann. Biol. Clin., 50: 337–353.
Wilding et al., (1994), Clin. Chem., 40/1:43–47.
Ikada, (1994), Biomaterials, 15/10: 725–736.
Arkles, (1977) Chemtech, 7: 125.
Matsue et al., (1990), Rev. Polarogr., 36: 67.
Aoki et al., (1990), Anal. Chem., 62: 2206–2210.
Linliu et al., (1994), Rev. Sci. Instrum., 65/12: 3823–3828.
Esashi et al., (Jul. 1992), Proc. Micro. Electro Mechanical Systems, 11: 43–48.
Ballantine et al., (Jun. 1989), Anal. Chem., 6/11: 704–715.
Collison et al., (Apr. 1990), Anal. Chem., 62/7: 425–437.
Lamture et al., (1994), Nucleic Acids Res., 22/11: 2121–2125.
Burtis et al., (1974), Clin. Chem., 20/8: 932–941.
Foucault, (1991), Anal. Chem., 63: Page???????.
Poole et al., (Jan. 1994), Anal. Chem., 66/1: 27A–37A.
Shoji & Esahi, (1992), Sensors and Actuators, B8: 205.
Bor Fuh et al., (1995), Biotechnol. Prog., 11: 14–20.
Heineman, (1993), App. Biochem. Biotech., 41: 87–97.
Schembri et al., (Sep. 1992), Clinical Chemistry, vol. 38, No. 9, pp. 1995–1670.
Patent Abstracts of Japan, (Jan. 1992), vol. 40, No. 9, pp. 1805–1809.
Arquint et al., (Sep. 1994), Clinical Chemistry, vol. 40, No. 9, pp. 1805–1809.
Blackburn et al., (1991), Clin. Chem., 37: 1534–1539.
Wilding et al., (1994), Automat. Analyt. Tech., 40: 43–47.
Enclopedia of Polymer Science & Technology, $2^{nd}$ Edition, (1989), vol. 3, pp. 421–430.
Enclopedia of Polymer Science & Technology, $2^{nd}$ Edition, (1989), vol. 3, pp. 675–689.
Veider et al., (1995), Eurosensors IX, pp. 284–286.
Huff et al., (1994), $7^{th}$ International Conference of Solid–State Sensors and Actuators, pp. 98–101.
Glass et al., (Jun. 1987), Appl. Optics, 26/11: 2181–2187.
Haab et al., (1995), Anal. Chem., 67: 3253–3260.
Dessy, (Oct. 1989), Anal. Chem., 61–19: 1079–1094.
Rosenzweig et al., (1994), Anal. Chem., 66:1771–1776.
Reijenga et al., (1983), J. Chromatography, 260:241–254.
Nakagawa et al., (Apr. 1983) Proc. IEEE Workshop of Micro Electro Mechanical Systems, p. 89.

* cited by examiner

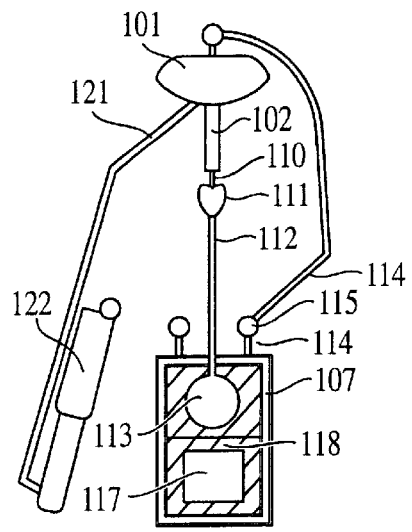
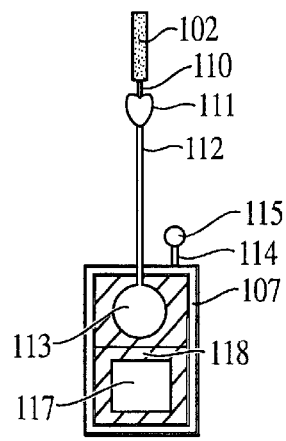
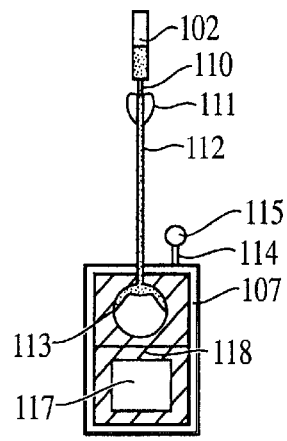
FIG. 3A                FIG. 3B                FIG. 3C
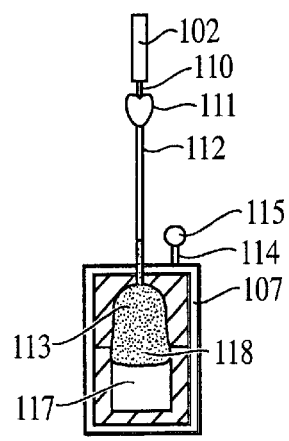
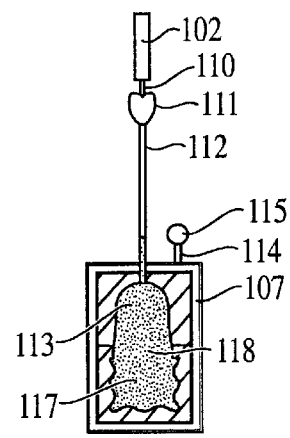
FIG. 3D                FIG. 3E

DEVICES AND METHODS FOR USING CENTRIPETAL ACCELERATION TO DRIVE FLUID MOVEMENT IN A MICROFLUIDICS SYSTEM FOR PERFORMING BIOLOGICAL FLUID ASSAYS

This application is a Continuation-in-Part of U.S. Ser. No. 09/083,678, filed May 22, 1998 now U.S. Pat. No. 6,063,589. This application is also related to U.S. Ser. No. 08/995,056, filed Dec. 19, 1997 now U.S. Pat. No. 6,143, 247, U.S. Ser. No. 08/910,726, filed Aug. 12, 1997 now U.S. Pat. No. 6,143,248, U.S. Ser. No. 08/768,990, filed Dec. 18, 1996 now U.S. Pat. No. 6,319,469 and U.S. Ser. No. 08/761,063, filed Dec. 5, 1996, the disclosures of every one of which are explicitly incorporated by reference herein.

BACKGROUND OF THE INVENTION

1. Field of the Invention

This invention relates to methods and apparatus for performing microanalytic analyses and procedures on fluid samples. In particular, the invention relates to microminiaturization of genetic, biochemical and chemical processes related to analysis, synthesis and purification. Specifically, the invention provides a microsystem platform that is rotationally manipulated by a micromanipulation device, thereby utilizing the centripetal forces resulting from rotation of the platform to motivate fluid movement through microchannels embedded in the microplatform. The microsystem platforms of the invention are provided having microfluidics components, chambers and reservoirs, resistive heating elements, temperature sensing elements, mixing structures, capillary and sacrificial valves, and methods for using these microsystems platforms for performing biological, enzymatic, immunological and chemical assays.

2. Summary of the Related Art

Assays for detecting analytes in fluid samples, particularly complex fluids such as biological fluid samples, are used for a variety of diagnostic, environmental, synthetic and analytical purposes in the medical, biological, chemical, biochemical and environmental arts.

Certain analytes are important for diagnosis and monitoring of acute and chronic disease in humans. For example, diabetes is the fourth major cause of morbidity and mortality in the U.S., even though the biochemical basis for the disease has been known for at least a century and drugs (primarily insulin) and methods for managing the disease are robust and widely used. It has been recognized that sensitive monitoring of blood sugar levels, either directly or by detecting levels of metabolites and disease-associated modifications (such as the relative fraction of glycated hemoglobin in the bloodstream) is important in managing the disease. However, fast and inexpensive ways of performing the assays necessary for efficient management of multiple indicators of the disease state are not currently available.

In the field of medical, biological and chemical assays, mechanical and automated fluid handling systems and instruments are known in the prior art.

U.S. Pat. No. 4,279,862, issued Jul. 21, 1981 to Bertaudiere et al. disclose a centrifugal photometric analyzer.

U.S. Pat. No. 4,381,291, issued Apr. 26, 1983 to Ekins teach analytic measurement of free ligands.

U.S. Pat. No. 4,515,889, issued May 7, 1985 to Klose et al. teach automated mixing and incubating reagents to perform analytical determinations.

U.S. Pat. No. 4,676,952, issued Jun. 30, 1987 to Edelmann et al. teach a photometric analysis apparatus.

U.S. Pat. No. 4,745,072, issued May 17, 1998 to Ekins discloses immunoassay in biological fluids.

U.S. Pat. No. 5,061,381, issued Oct. 29, 1991 to Burd discloses a centrifugal rotor for performing blood analyses.

U.S. Pat. No. 5,122,284, issued Jun. 16, 1992 to Braynin et al. discloses a centrifugal rotor comprising a plurality of peripheral cuvettes.

U.S. Pat. No. 5,160,702, issued Nov. 3, 1993 to Kopf-Sill and Zuk discloses rotational frequency-dependent valves using capillary forces and siphons, dependent on "wettability" of liquids used to prime said siphon.

U.S. Pat. No. 5,171,695, issued Dec. 15, 1992 to Ekins discloses determination of analyte concentration using two labeling markers.

U.S. Pat. No. 5,173,193, issued Dec. 22, 1992 to Schembri discloses a centrifugal rotor for delivering a metered amount of a fluid to a receiving chamber on the rotor.

U.S. Pat. No. 5,242,803, issued Sep. 7, 1993 to Burtis et al. disclose a rotor assembly for carrying out an assay.

U.S. Pat. No. 5,409,665, issued Apr. 25, 1995 to Burd discloses a cuvette filling in a centrifuge rotor.

U.S. Pat. No. 5,413,009, issued Jul. 11, 1995 to Ekins discloses a method for analyzing analytes in a liquid.

U.S. Pat. No. 5,472,603, issued Dec. 5, 1995 to Schembri discloses an analytical rotor comprising a capillary passage having an exit duct wherein capillary forces prevent fluid flow at a given rotational speed and permit flow at a higher rotational speed.

Anderson, 1968, *Anal. Biochem.* 28: 545–562 teach a multiple cuvette rotor for cell fractionation.

Renoe et al., 1974 *Clin. Chem.* 20: 955–960 teach a "minidisc" module for a centrifugal analyzer.

Burtis et al., 1975, *Clin. Chem.* 20: 932–941 teach a method for a dynamic introduction of liquids into a centrifugal analyzer.

Fritsche et al., 1975, *Clin. Biochem.* 8: 240–246 teach enzymatic analysis of blood sugar levels using a centrifugal analyzer.

Burtis et al., 1975, *Clin Chem.* 21: 1225–1233 teach a multipurpose optical system for use with a centrifugal analyzer.

Hadjiioannou et al., 1976, *Clin. Chem.* 22: 802–805 teach automated enzymatic ethanol determination in biological fluids using a miniature centrifugal analyzer.

Lee et al., 1978, *Clin. Chem.* 24: 1361–1365 teach a automated blood fractionation system.

Cho et al., 1982, *Clin. Chem.* 28: 1956–1961 teach a multichannel electrochemical centrifugal analyzer.

Bertrand et al., 1982, *Clinica Chimica Acta* 119: 275–284 teach automated determination of serum 5'-nucleotidase using a centrifugal analyzer.

Schembri et al., 1992, *Clin Chem.* 38: 1665–1670 teach a portable whole blood analyzer.

Walters et al., 1995, *Basic Medical Laboratory Technologies*, 3rd ed., Delmar Publishers: Boston teach a variety of automated medical laboratory analytic techniques.

Recently, microanalytical devices for performing select reaction pathways have been developed.

U.S. Pat. No. 5,006,749, issued Apr. 9, 1991 to White disclose methods apparatus for using ultrasonic energy to move microminiature elements.

U.S. Pat. No. 5,252,294, issued Oct. 12, 1993 to Kroy et al. teach a micromechanical structure for performing certain chemical microanalyses.

U.S. Pat. No. 5,304,487, issued Apr. 19, 1994 to Wilding et al. teach fluid handling on microscale analytical devices.

U.S. Pat. No. 5,368,704, issued Nov. 29, 1994 to Madou et al. teach microelectrochemical valves.

International Application, Publication No. WO93/22053, published Nov. 11, 1993 to University of Pennsylvania disclose microfabricated detection structures.

International Application, Publication No. WO93/22058, published Nov. 11, 1993 to University of Pennsylvania disclose microfabricated structures for performing polynucleotide amplification.

Columbus et al., 1987, Clin. Chem. 33: 1531–1537 teach fluid management of biological fluids.

Ekins et al., 1994 Ann. Biol. Clin. 50: 337–353 teach a multianalytic microspot immunoassay.

Wilding et al., 1994, Clin. Chem. 40: 43–47 disclose manipulation of fluids on straight channels micromachined into silicon.

One drawback in the prior art microanalytical methods and apparati has been the difficulty in designing systems for moving fluids on microchips through channels and reservoirs having diameters in the 10–500 $\mu$m range. Microfluidic systems require precise and accurate control of fluid flow and valving to control chemical reactions and analyte detection. Conventional pumping and valving mechanisms have been difficult to incorporate into microscale structures due to inherent conflicts-of-scale. These conflicts of scale arise in part due to the fact that molecular interactions arising out of mechanical components of such components, which are negligible in large (macroscopic) scale devices, become very significant for devices built on a microscopic scale.

While devices and pumping and valving mechanisms have been developed which overcome some of these conflict-of-scale difficulties, there are other inherent problems with these systems. A number of microanalytical platforms have been developed which use electrokinetic forces for fluid pumping: electroosmotic flow devices; electrohydrodynamic devices; and electrophoretic devices. An inherent drawback in these systems is that they rely on precise control of pH and free charges in the fluid being pumped. This makes them incapable of pumping most raw biological samples, such as blood and urine, and creates difficulties in pumping organic solvents. In cases where these systems may be used, pre-conditioning of the fluid to enhance electrokinetic effects is usually required.

Systems that use centripetal force to effect fluid movement in microstructures address the need for a pumping mechanism to effect fluid flow, but cannot alone solve these scale-related drawbacks of conventional fluidics reduced to microfluidics scale. There remains a need for a simple, flexible, reliable, rapid and economical microanalytic and microsynthetic reaction platform for performing biological, biochemical and chemical analyses and syntheses that can move fluids within the structural components of a microsystems platform. Such a platform should be able to move nanoliter-to microliter amounts of fluid, including reagents and reactants, at rapid rates to effect the proper mixing of reaction components, removal of reaction side products, and isolation of desired reaction products and intermediates. There remains a need in the art for centripetally-motivated microfluidics platforms capable of precise and accurate control of flow and metering of fluids in both microchip-based and centrifugal microplatform-based technologies.

SUMMARY OF THE INVENTION

This invention provides Microsystems platforms as disclosed in co-owned and co-pending U.S. Ser. No. 08/761, 063, filed Dec. 5, 1996 and U.S. Ser. No. 09/083,678, filed May 22, 1998, each of which is incorporated by reference herein. Specifically, this invention provides microfluidics platforms for performing biological, enzymatic, immunological and chemical assays.

It is an advantage of the centrifugal rotors and Microsystems platforms of the invention that an imprecise amount of a fluid comprising a biological sample can be applied to the rotor or platform and a precise volumetric amount of the biological sample is delivered to a fluid reservoir comprising a reaction vessel or other component of the rotor or platform for performing chemical, biochemical, immunological or other analyses. It is an advantage of the centrifugal rotors and microsystems platforms of the invention that metering of said precise amount of a biological fluid sample, for example, a drop of blood, is provided as an intrinsic property of the metering capillary channel of the rotor or platform, thereby avoiding variability introduced by centripetal metering of the sample into a reaction reservoir. It is a further advantage of the centrifugal rotors and Microsystems platforms of the invention that an operator can avoid having to precisely measure an amount of a fluid comprising a biological sample for application to the rotor or microsystem platform, thereby permitting end-users, including consumers, having a lower level of sophistication to use a medically diagnostic or other embodiment of the rotor or microsystem platform of the invention.

It is an advantage of the centrifugal rotors and Microsystems platforms of the invention that fluid movement into and out of fluid reservoirs on the rotor or platform is precisely determined by displacement of a first fluid, such as biological sample, from a fluid reservoir by a second fluid contained in a second reservoir on the rotor or platform. It is also an advantage of the centrifugal rotors and Microsystems platforms of the invention that approximately complete replacement of the volumetric capacity of a first reservoir can be achieved by using fluid displacement as disclosed herein, thereby providing for maximum recovery of a first fluid sample upon displacement by a second fluid, or maximum delivery and replacement of the first fluid by the second fluid. This aspect of the invention is advantageous for providing sequential chemical or biochemical reaction steps wherein mixing of the reagents is not desired.

It is also an advantage of the centrifugal rotors and Microsystems platforms of the invention that these platforms provide an integrated microfluidics system containing components and structures for performing microanalytic assays whereby fluid flow on the platform is motivated by centripetal force and controlled by capillary and/or sacrificial valves. The invention provides such integrated platforms whereby an operator is required simply to apply a sample, most preferably an imprecise volume of a fluid sample, to an entry port on the disk surface, and a complex series of analytical steps are performed without further operator manipulation on the platform. Movement of fluids on the disk, and the sequence of analytical reaction steps performed thereupon, is a consequence of changes in rotor speed and/or the opening of sacrificial valves as directed by an instruction set contained in a program contained on the disk itself or in the memory of the micromanipulation apparatus that controls disk rotation and performance.

The Microsystems platforms also provide disks that can perform a multiplicity of analytical reactions on either several samples or a particular sample, whereby the reactions are performed sequentially or individually. In addition, a wide variety of analytic reactions can be performed on the microsystems platforms of the invention, as further described below.

Specific preferred embodiments of the present invention will become evident from the following more detailed description of certain preferred embodiments and the claims.

DESCRIPTION OF THE DRAWINGS

FIGS. 1 through 8 are schematic representations of microfluidics arrays and components for performing direct analyte detection assays using the microsystems platforms of the invention.

DETAILED DESCRIPTION OF PREFERRED EMBODIMENTS

Figure 1A:
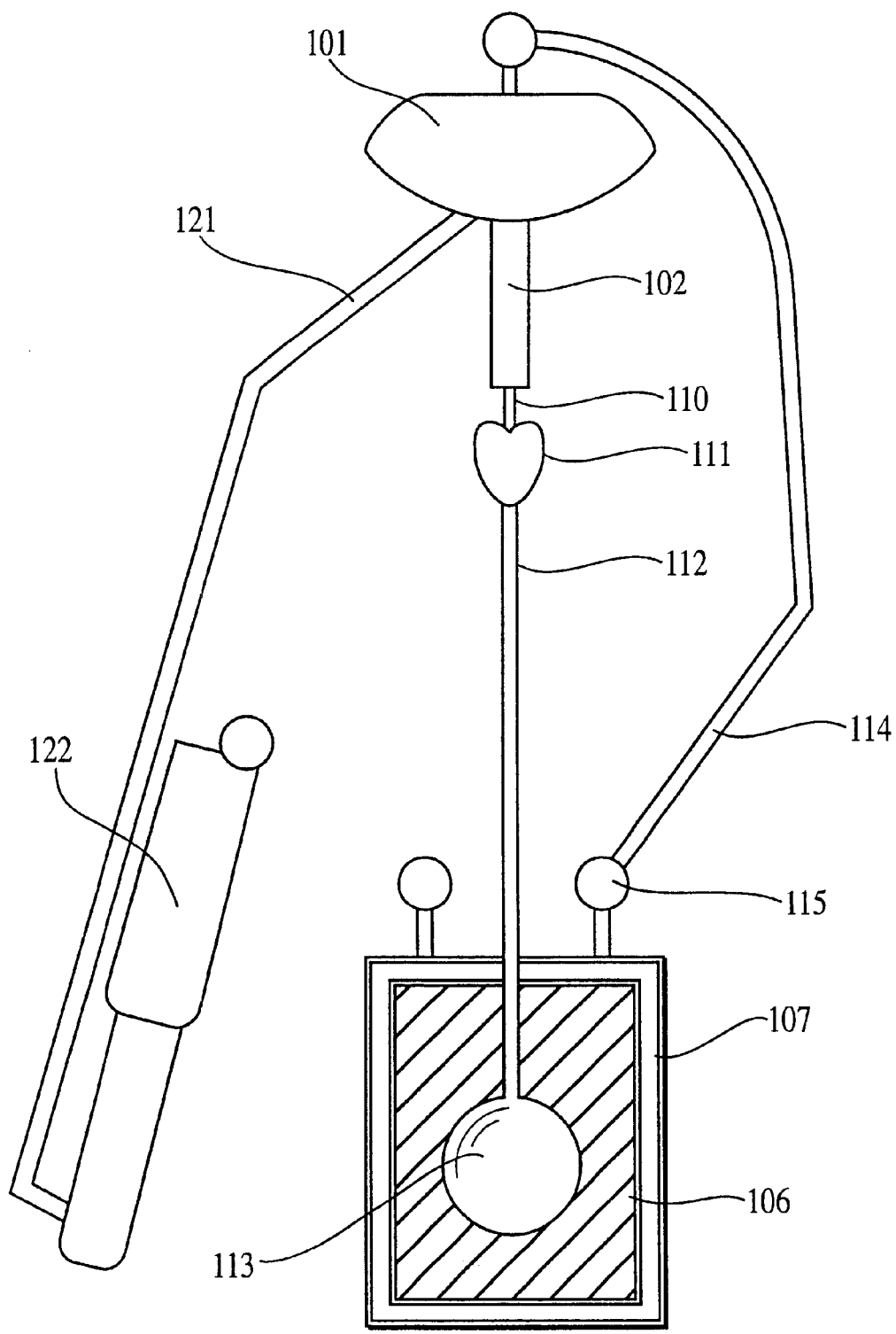

The present invention provides centrifugal rotors and Microsystems platforms for providing centripetally-motivated fluid micromanipulation.

For the purposes of this invention, the term "sample" will be understood to encompass any fluid, solution or mixture, either isolated or detected as a constituent of a more complex mixture, or synthesized from precursor species.

For the purposes of this invention, the term "in fluid communication" or "fluidly connected" is intended to define components that are operably interconnected to allow fluid flow between components. In preferred embodiments, the platform comprises a rotatable platform, more preferably a disk, whereby fluid movement on the disk is motivated by centripetal force upon rotation of the disk.

For the purposes of this invention, the term "a centripetally motivated fluid micromanipulation apparatus" is intended to include analytical centrifuges and rotors, microscale centrifugal separation apparati, and most particularly the microsystems platforms and disk handling apparati of International Application No. WO97/21090, incorporated by reference.

For the purposes of this invention, the term "Microsystems platform" is intended to include centripetally-motivated microfluidics arrays as disclosed in International Application No. WO97/21090.

For the purposes of this invention, the terms "capillary", "microcapillary and "microchannel" will be understood to be interchangeable and to be constructed of either wetting or non-wetting materials where appropriate.

For the purposes of this invention, the term "fluid chamber" will be understood to mean a defined volume on a rotor or Microsystems platform of the invention comprising a fluid.

For the purposes of this invention, the term "entry port" will be understood to mean a undefined volume on a rotor or Microsystems platform of the invention comprising a means for applying a fluid to the rotor or platform.

For the purposes of this invention, the term "capillary junction" will be understood to mean a junction of two components wherein one or both of the lateral dimensions of the junction are larger than the corresponding dimensions of the capillary. In wetting or wettable systems, such junctions are where capillary valving occurs, because fluid flow through the capillaries is stopped at such junctions. In non-wetting or non-wettable junctions, the exit from the chamber or reservoir is where the capillary junction occurs. In general, it will be understood that capillary junctions are formed when the dimensions of the components change from a small diameter (such as a capillary) to a larger diameter (such as a chamber) in wetting systems, in contrast to non-wettable systems, where capillary junctions form when the dimensions of the components change from a larger diameter (such as a chamber) to a small diameter (such as a capillary).

For the purposes of this invention, the term "biological sample" or "biological fluid sample" will be understood to mean any biologically-derived analytical sample, including but not limited to blood, plasma, serum, lymph, saliva, tears, cerebrospinal fluid, urine, sweat, plant and vegetable extracts, semen, cell culture fluids, cellular lysate, aqueous or non-aqueous fractions of the above and ascites fluid.

For the purposes of this invention, the term "air displacement channels" will be understood to include ports in the surface of the platform that are contiguous with the components (such as chambers and reservoirs) on the platform, and that comprise vents and microchannels that permit displacement of air from components of the platforms and rotors by fluid movement.

For the purposes of this invention, the term "capillary action" will be understood to mean fluid flow in the absence of rotational motion or centripetal force applied to a fluid on a rotor or platform of the invention.

For the purposes of this invention, the term "capillary microvalve" will be understood to mean a capillary comprising a capillary junction whereby fluid flow is impeded and can be motivated by the application of pressure on a fluid, typically by centripetal force created by rotation of the rotor or platform of the invention.

The microplatforms of the invention (preferably and hereinafter collectively referred to as discs or disks for the purposes of this invention), the terms "microplatform", "Microsystems platform" and "disc" or "disk" are considered to be interchangeable, and are provided to comprise one or a multiplicity of microsynthetic or microanalytic systems. Such microsynthetic or microanalytic systems in turn comprise combinations of related components as described in further detail herein that are operably interconnected to allow fluid flow between components upon rotation of the disk. These components can be fabricated as described below either integral to the disk or as modules attached to, placed upon, in contact with or embedded in the disk. The invention also comprises a micromanipulation device for manipulating the disks of the invention, wherein the disk is rotated within the device to provide centripetal force to effect fluid flow on the disk. Accordingly, the device provides means for rotating the disk at a controlled rotational velocity, for stopping and starting disk rotation, and advantageously for changing the direction of rotation of the disk. Both electromechanical means and control means, as further described herein, are provided as components of the devices of the invention. User interface means (such as a keypad and a display) are also provided, as further described in International Application WO97/21090.

Fluid (including reagents, samples and other liquid components) movement is controlled by centripetal acceleration due to rotation of the platform. The magnitude of centripetal acceleration required for fluid to flow at a rate and under a pressure appropriate for a particular microsystem is determined by factors including but not limited to the effective radius of the platform, the position angle of the structures on the platform with respect to the direction of rotation and the speed of rotation of the platform.

The capillary junctions and microvalves of the invention are based on the use of rotationally-induced fluid pressure to overcome capillary forces. Fluids which completely or partially wet the material of the microchannels (or reservoirs, reaction chambers, detection chambers, etc.) which contain them experience a resistance to flow when moving from a microchannel of narrow cross-section to one of larger cross-section, while those fluids which do not wet these materials resist flowing from microchannels (or reservoirs, reaction chambers, detection chambers, etc.) of large cross-section to those with smaller cross-section. This capillary pressure varies inversely with the sizes of the two microchannels (or reservoirs, reaction chambers, detection chambers, etc., or combinations thereof), the surface tension of the fluid, and the contact angle of the fluid on the material of the microchannels (or reservoirs, reaction chambers, detection chambers, etc.) Generally, the details of the cross-sectional shape are not important, but the dependence on cross-sectional dimension results in microchannels of dimension less than 500 $\mu$m exhibit significant capillary pressure. By varying the intersection shapes, materials and cross-sectional areas of the components of the Microsystems platform of the invention, valves are fashioned that require the application of a particular pressure on the fluid to induce fluid flow. This pressure is applied in the disks of the invention by rotation of the disk (which has been shown above to vary with the square of the rotational frequency, with the radial position and with the extent of the fluid in the radial direction). By varying capillary valve cross-sectional dimensions as well as the position and extent along the radial direction of the fluid handling components of the microsystem platforms of the invention, capillary valves are formed to release fluid flow in a rotation-dependent manner, using rotation rates of from 100 rpm to several thousand rpm. This arrangement allows complex, multistep fluid processes to be carried out using a pre-determined, monotonic increase in rotational rate. The theoretical principles underlying the use of capillary junctions and microvalves are disclosed in International Patent Application, Publication No. WO98/07019, incorporated by reference.

The instant invention provides Microsystems platforms comprising microfluidics components, heating elements, temperature sensing elements, capillary valves, sacrificial valves and a rotor design for transmitting electrical signals to and from the microsystems platforms of the invention. The invention provides fluidics components for capillary metering of precise amounts of a volume of a fluid sample from the application of a less precise volume of a fluid sample at an entry port on the microsystem platform. These embodiments of the invention provide for delivery of precise amounts of a sample such as a biological fluid sample without requiring a high degree of precision or accuracy by the operator or end-user in applying the fluid to the platform, and is advantageous in embodiments of the Microsystems platforms of the invention that are used by consumers and other relatively unsophisticated users. The invention also provides laminar flow-dependent replacement of a fluid in a first chamber by a second displacement fluid in a second chamber on the platform. These embodiments of the invention provide approximately complete replacement of a fluid in one chamber on the platform with fluid from another, and thereby provide means for practicing sequential chemical reactions and other sequential processes on the platform under conditions wherein mixing of the two fluids is disadvantageous. The invention also provides turbulent flow mixing components, which permit thorough mixing of different fluid components on the platform, and in particular, the invention provides mixing chambers fluidly connected with fluid reservoirs containing equal amounts of two or more different fluids or unequal amounts of two or more different fluids. In addition, the invention provides fluid reservoirs fluidly connected with mixing chamber of the invention and shaped to determine the relative rate of flow of each of the different fluids into the mixing chamber. In these embodiments, gradients of two fluids differing in viscosity, solute concentration or concentration of suspended particulates can be produced using the mixing chambers of the invention, as disclosed; U.S. Ser. No. 09/083,678 incorporated by reference. Such gradients can be transferred to reservoirs on the platform for further analytical manipulations, and can form the basis for controlled testing of concentration-dependent effects of various catalysts, drugs, toxins or other biological or chemical agents.

Platforms of the invention such as disks and the components comprising such platforms are advantageously provided having a variety of composition and surface coatings appropriate for a particular application. Platform composition will be a function of structural requirements, manufacturing processes, and reagent compatibility/chemical resistance properties. Specifically, platforms are provided that are made from inorganic crystalline or amorphous materials, e.g. silicon, silica, quartz, inert metals, or from organic materials such as plastics, for example, poly(methyl methacrylate) (PMMA), acetonitrile-butadiene-styrene (ABS), polycarbonate, polyethylene, polystyrene, polyolefins, polypropylene and metallocene. These may be used with unmodified or modified surfaces. Surface properties of these materials may be modified for specific applications. Surface modification can be achieved by silanization, ion implantation and chemical treatment with inert-gas plasmas (i.e., gases through which electrical currents are passed to create ionization). Also provided by the invention are platforms made of composites or combinations of these materials, for example, platforms manufactured of a plastic material having embedded therein an optically transparent glass surface comprising for example the detection chamber of the platform. Microplatform disks of the invention are preferably fabricated from thermoplastics such as teflon, polyethylene, polypropylene, methylmethacrylates and polycarbonates, among others, due to their ease of molding, stamping and milling. Alternatively, the disks can be made of silica, glass, quartz or inert metal. A fluid handling system is built by sequential application of one or more of these materials laid down in stepwise fashion onto the thermoplastic substrate. Alternatively, the entire disc can be injection molded, embossed or stamped. Disks of the invention are fabricated with an injection molded, optically-clear base layer having optical pits in the manner of a conventional compact disk (CD). The optical pits provide means for encoding instrument control programming, user interface information, graphics, data analysis, and, sound specific to the application and driver configuration. The driver configuration depends on whether the micromanipulation device is a hand-held, benchtop or floor model, and also on the details of external communication and other specifics of the hardware configuration. This layer is then overlaid with a reflective surface, with appropriate windows for external detectors, specifically optical detectors, being left clear on the disk. Other layers of polycarbonate of varying thickness are laid down on the disk in the form of channels, reservoirs, reaction chambers and other structures, including provisions on the disk for valves and other control elements. These layers can be pre-fabricated and cut with the appropriate geometries for a given application and assembled on the disk. Layers comprising materials other than polycarbonate can also be incorporated into the disk. The composition of the layers on the disk depend in large part on the specific application and the requirements of chemical compatibility with the reagents to be used with the disk. Electrical layers can be incorporated in disks requiring electric circuits, such as electrophoresis applications and electrically-controlled valves. Control devices, such as integrated circuits, laser diodes, photodiodes and resistive networks that can form selective heating areas or flexible logic structures can be incorporated into appropriately wired recesses, either by direct fabrication of modular installation onto the disk. Reagents that can be stored dry can be introduced into appropriate open chambers by spraying into reservoirs using means similar to inkjet printing heads, and then dried on the disk. A top layer comprising access ports and air vents, ports or shafts is then applied. Liquid reagents are then injected into the appropriate reservoirs, followed by application of a protective cover layer comprising a thin plastic film.

The platforms of the invention are preferably provided with a multiplicity of components, either fabricated directly onto the platform, or placed on the platform as prefabricated modules. In addition to the integral components, certain devices and elements can be located external to the platform, optimally positioned on a device of the invention in relation to the platform, or placed in contact with the platform either while rotating or when at rest. Components optimally comprising the platforms of the invention or a controlling device in combination therewith include detection chambers, reservoirs, valving mechanisms, detectors, sensors, temperature control elements, filters, mixing elements, and control systems.

This invention provides microsystems platforms comprising the following components.

1. Fluidics Components

The platforms of the invention are provided comprising microfluidics handling structures in fluidic contract with one another. In preferred embodiments, fluidic contact is provided by capillary or microchannels comprising the surface of the platforms of the invention. Microchannel sizes are optimally determined by specific applications and by the amount of delivery rates required for each particular embodiment of the platforms and methods of the invention. Microchannel sizes can range from 0.02 mm to a value close to the thickness of the platform. Microchannel shapes can be trapezoid, circular or other geometric shapes as required. Microchannels preferably are embedded in a platform having a thickness of about 0.1 to 100 mm, wherein the cross-sectional dimension of the microchannels across the thickness dimension of the platform is less than 500 $\mu$m–800 $\mu$m and from 1 to 90 percent of said cross-sectional dimension of the platform. In these embodiments, which are based on the use of rotationally-induced fluid pressure to overcome capillary forces, it is recognized that fluid flow is dependent on the orientation of the surfaces of the components. Fluids which completely or partially wet the material of the microchannels, reservoirs, detection chambers, etc. (i.e., the components) of the platforms of the invention which contain them experience a resistance to flow when moving from a component of narrow cross-section to one of larger cross-section, while those fluids which do not wet these materials resist flowing from components of the platforms of the invention of large cross-section to those with smaller cross-section. This capillary pressure varies inversely with the sizes of the two components, or combinations thereof, the surface tension of the fluid, and the contact angle of the fluid on the material of the components. Generally, the details of the cross-sectional shape are not important, but the dependence on cross-sectional dimension results in microchannels of dimension less than 500 $\mu$m exhibit significant capillary pressure. By varying the intersection shapes, materials and cross-sectional areas of the components of the platform of the invention, "valves" are fashioned that require the application of a particular pressure on the fluid to induce fluid flow. This pressure is applied in the disks of the invention by rotation of the disk (which has been shown above to vary with the square of the rotational frequency, with the radial position and with the extent of the fluid in the radial direction). By varying capillary valve cross-sectional dimensions as well as the position and extent along the radial direction of the fluid handling components of the platforms of the invention, capillary valves are formed to release fluid flow in a rotation-dependent manner, using rotation rates of from 100 rpm to several thousand rpm. This arrangement allows complex, multistep fluid processes to be carried out using a pre-determined, monotonic increase in rotational rate.

A first example of the microfluidics arrays provided by this invention is shown in FIGS. 1A through 1D. A Microsystems platform is provided by the invention that is specifically designed for performing an assay for detecting a chemical species in a complex mixture, preferably an aqueous mixture. These Figures illustrate an array advantageously used for any such assay; detection of blood glucose concentration is illustrated herein. It will be understood that in this description, the use of the words "cell" and "particulate" will be interchangeable, and that cells are a particular example of a specific particulate species comprising the fluid samples, and most preferably the biological fluid samples, analyzed using the present invention.

A microsystems platform provided by the invention and specifically designed for performing blood glucose assay is illustrated in FIG. 1A. Disk embodiments of the platforms of the invention were fashioned, for example, from machined acrylic or injection-molded polycarbonate, polystyrene, polypropylene, acetonitrile-butadiene-styrene, or high-density polyethylene (HDPE). The overall disc dimensions include an outer radius of from about 1 cm to about 15 cm and an inner radius of from about 0.1 cm to about 1 cm, wherein the disk was mounted on the spindle of a rotary device. The thickness of the disc ranged from about 0.2 mm to about 1.5 cm. All surfaces coming into contact with blood on the platform may be advantageously treated with heparin, EDTA or other anticoagulants to facilitate fluid flow thereupon.

The components of the blood glucose assay were prepared as follows. Fluid sample entry port 101 having a depth in the platform surface from about 0.15 cm to about 3 mm and lateral dimensions of from about 0.1 cm to about 2.5 cm were constructed on the platform, and designed to accommodate a volume of from about 5 to about 200 $\mu$L. This entry port was fluidly connected with a metering capillary 102 having a square cross-sectional diameter of from about 0.02 mm to about 2 cm and proximal ends rounded with respect to entry port 101; the length of this metering chamber array was sufficient to contain a total volume of from about 15 to about 150 μL. The entry port was also constructed to be fluidly connected with an overflow capillary 121 having a cross-sectional diameter of from about 0.02 mm to about 2 mm and proximal ends rounded with respect to entry port 101. The overflow capillary was fluidly connected with an overflow chamber 122 having a depth in the platform surface of from about 0.02 mm to about 9 mm, greater than the depth of the overflow capillary 121. Each of the chambers on the platform were also connected with air ports or air channels, such as 114, that have dimensions of from about 0.02 mm to about 2 mm deep and permitted venting of air displaced by fluid movement on the platform. A capillary junction 115 that is from about 0.03 mm to about 2.2 mm deep is present in the air channel to prevent fluid flow into the air channel.

Entry port 101 was positioned on the platform from about 1 cm to about 12 cm from the center of rotation. Metering chamber 102 extended from about 0.25 cm to about 2 cm from entry port 101. The extent of the length of overflow capillary 121 was greater than the extent of the length of metering capillary 102. The position of overflow chamber 122 was, for example, from about 1.2 cm to about 14 cm from the axis of rotation.

Figure 1B:
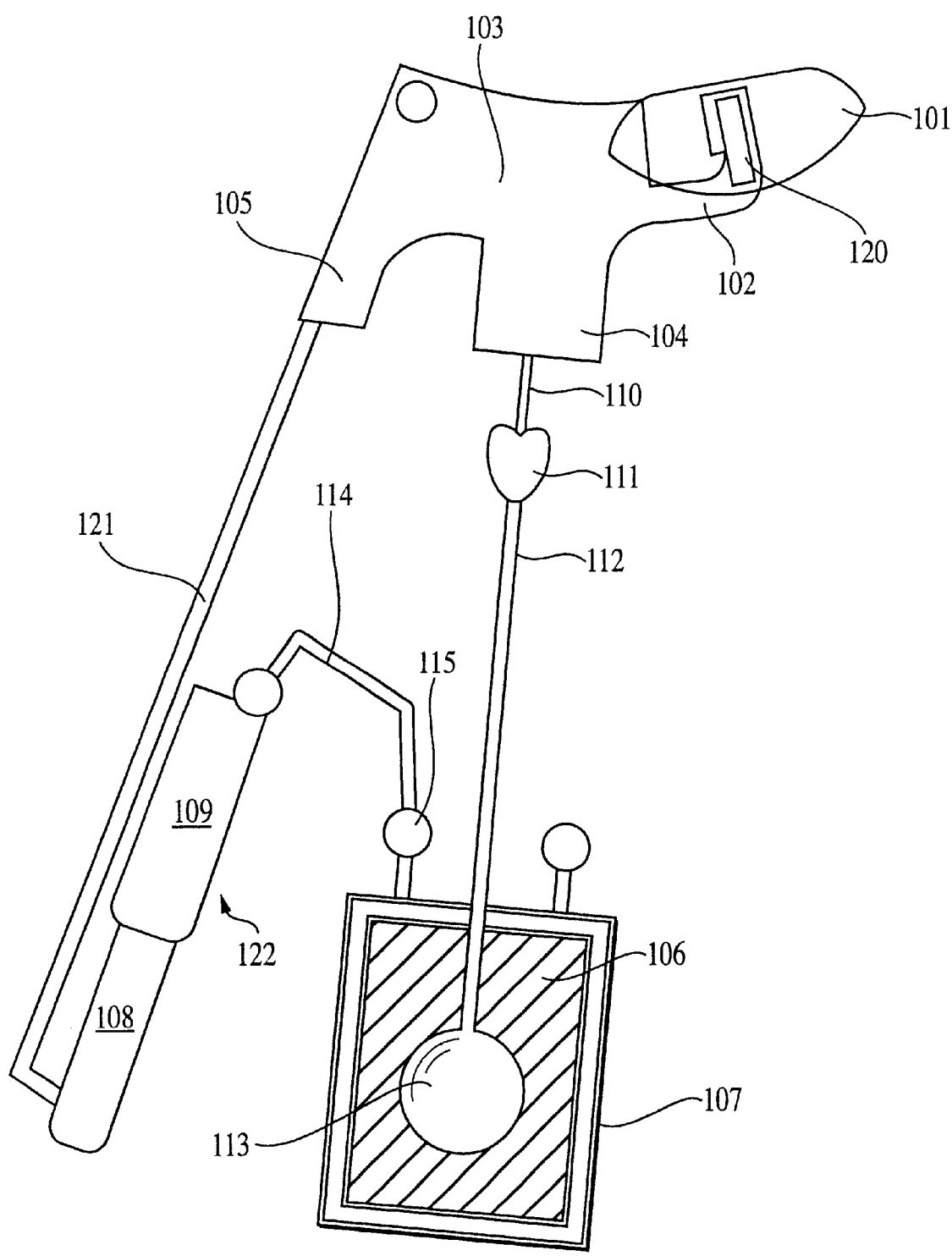

In an alternative embodiment of the fluid metering structures of the invention, shown in FIG. 1B, fluid sample entry port 101 is comprised of a funnel having a depth in the platform surface from about 0.75 mm to 5 mm, lateral dimensions of from about 2 mm to 2 cm in the long dimension and from about 2 mm to 2 cm in the short dimension and positioned from about 0.75 cm to about 5 cm from the center of rotation, and designed to accommodate a volume of about 5 to about 200 μL. The bottom surface of the entry port consists of a slot 120 fluidly connected to microfluidics structures formed in the other (under) side of the microfluidics surface of the platform. Entry port 101 is connected to entry passageway 102 having a rectangular cross-sectional diameter of from about 0.1 mm to 5 mm wide and from about 0.1 mm to 5 mm deep and extending from about 0.1 cm to about 3 cm from entry port 101. The entry passageway 102 is fluidly connected to blood entry chamber 103. Blood entry chamber 103 has a depth of from about 0.1 mm to 5 mm, lateral dimensions of from about 1 mm to about 4 cm, and is positioned from about 0.75 cm to about 2.5 cm from the center of rotation. Blood entry chamber 103 further comprises blood metering volume 104 designed to accommodate a volume of from about 1 μL to about 50 μL and an overflow passageway 105. The overflow passageway was fluidly connected with an overflow capillary 106 having a depth in the platform surface of from about 0.1 mm to about 1 mm. Overflow capillary 121 is further fluidly connected with overflow chamber 122 which is comprised of two parts, a shallow outer portion 108 having a depth from about 0.05 mm to about 0.5 mm and a deeper inner portion 109 having a depth of from about 0.1 mm to 5 mm. Overflow chamber 122 is positioned from about 4 cm to about 5.8 cm from the axis of rotation. The distal end of the blood overflow capillary 121 is chosen to be farther from the center of rotation than the distal end of blood chamber 104. Each of the chambers on the platform were also connected with air ports or air channels 114, that are from about 0.1 mm to about 5 mm deep and permit venting of air displaced by fluid movement on the platform. A capillary junction 115 that is from about 0.03 mm to about 2.2 mm deep is present in the air channel to prevent fluid flow into the air channel. In alternative embodiments, these vents may be multiply connected to one another through a manifold such that fluid flow merely displaces air within the structure, rather than forcing it through vents in the platform surface.

Alternatively, an unmetered amount of a blood sample is placed directly in blood fluid chamber 104, which in this embodiment is open to the surface of the disk to accept blood application. In these embodiments, the amount of blood fluid to be assayed is controlled by the capacity of assay chamber 107 or the matrix 106 contained therein as described below.

As described herein for performing blood glucose assays (and as understood in the art that essentially the same microfluidics structures can be used for a multiplicity of blood analyte assays or, more generally, for analyte assays in any fluid sample, most preferably a biological fluid sample), a capillary barrier prevents movement of the fluid sample directly into the assay chamber 107. In the metering structure shown in FIG. 1A, fluid (or more properly for this illustrative example, blood) metering capillary 102 acted as a capillary barrier that prevented blood fluid flow from metering capillary 102 at a first, non-zero rotational speed $f_1$, ranging from about 200 rpm to about 450 rpm and sufficient to permit fluid flow comprising overflow from the entry port 101 through overflow capillary 121 and into overflow chamber 122. This capillary boundary was constructed to be overcome at a second rotational speed $f_2$, ranging from about 250 rpm to about 900 rpm (where $f_2 > f_1$). In the alternative embodiments shown in FIGS. 1B and 1C, blood fluid chamber 104 acted as a capillary barrier that was maintained during rotation at a rotational speed sufficient to motivate excess fluid sample from the entry port 101 to the overflow chamber 122, and was overcome at a second rotational speed greater than the first rotational speed to permit fluid sample flow into assay chamber 107.

Blood metering capillary 102 and blood fluid chamber 104 were in different alternatives of the Microsystems platforms of the invention fluidly connected to capillary 110 that was from about 0.02 mm to about 2 mm deep and had a cross-sectional diameter of from about 0.02 mm to about 2 mm and was connected to capillary or sacrificial valve 111. Sacrificial or capillary valve 111 was further fluidly connected with capillary 112 that was from about 0.02 mm to about 2 mm deep and had a cross-sectional diameter of from about 0.02 mm to about 2 mm, and further to assay chamber 107. In capillary valve embodiments, the junction between capillary 110 and capillary 112 creates capillary valve 111, wherein said capillary valve 111 was from about 0.03 mm to about 2.2 mm deep and had a cross-sectional diameter of from about 0.03 mm to about 2.2 mm. In order to function as a capillary valve, the junction between capillary 110 and capillary 112 must have a depth and/or cross sectional area greater than that of capillary 110 in a disc fabricated from hydrophilic materials such as acrylic. In sacrificial valve embodiments, intermediate melting temperature materials (including, for example, waxes as described above) are placed in the lumen of capillary 110 forming a fluid-tight seal. In these embodiments, chamber 111 is fluidly connected to the sacrificial valve so that melted wax from the release sacrificial valve is sequestered in the chamber.

Rectangular assay chamber 107 was constructed in the surface of the platform to have a depth of from about 0.2 mm to about 3 mm, most preferably comprising a circular or rectangular depression 113 connected to capillary 112. Depression 113 was constructed to have a volumetric capacity of from half to twice the assay volume. Assay chamber 107 also comprised a pad or matrix 106 of a hydrophilic substance. Materials used to prepare said matrices include but are not limited to derivatized nylons, nitrocellulose, fiberglass and polyesters, most preferably having a pore size of 0.2–2.0 µm, most preferably comprising a positively-charged nylon matrix having a pore size of about 0.8 µm. The upper limit on pore size of matrix 106 is chosen to inhibit or prevent blood cell entry into the matrix. The matrix is positioned in assay chamber 107 to be in fluidic contact with depression 113, more preferably covering depression 113, and most preferably having a surface area greater than the surface area of depression 113. The matrix was further impregnated with immobilized reagents which produce a detectable product proportional to the amount or concentration of glucose in a blood sample. Most preferably, the detectable product is a colored product, i.e., a product absorbing light at a detectable, most preferably a visible, wavelength.

In preparing matrices according to the invention, reagents advantageously used to detect and more preferably quantitate an amount of a component of a biological fluid sample are impregnated into the matrix. As a non-limiting example, glucose is detected according to the invention using a glucose oxidase assays system, as described in additional detail below. Matrices for performing such assays using the microfluidics platforms of the invention are prepared by saturating the matrix membrane with an 8 mL solution of distilled water containing 0.12 g 2,5-ferandione polymer with methoxylene (CAS: 9011-16-9), 10 mg EDTA, 200 mg Polypep® Low Viscosity (Sigma Chemical Company, St. Louis, Mo.), 668 mg sodium citrate, 28.75 mg glucose oxidase and 27.3 mg peroxidase. The saturated membrane is then dried and then saturated with 5 mL acetonitrile and 5 mL distilled water containing 40 mg 3-methyl-2-benzothiazolinone hydrazone and 80 mg 3-dimethylaminobenzoic acid. The saturated membrane is dried and applied to the microfluidics disk of the invention for use.

Figure 15:
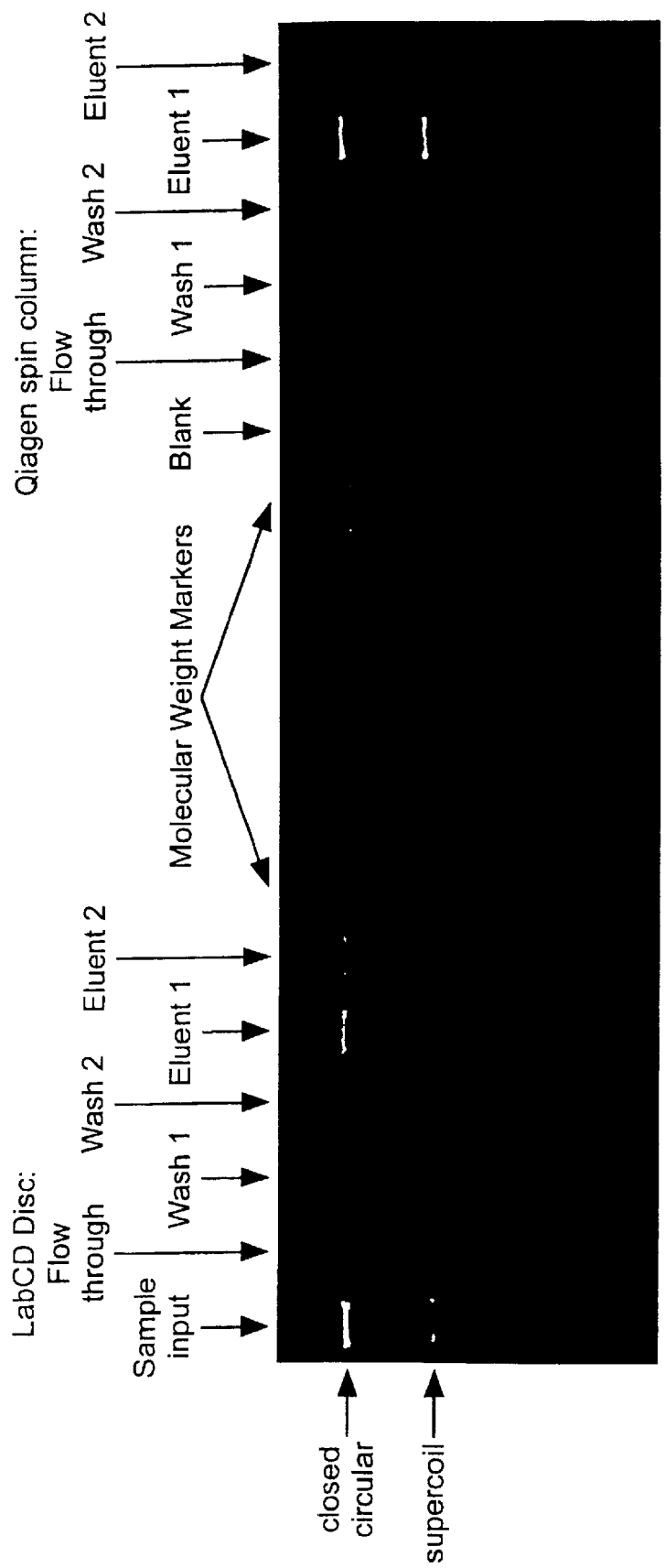
FIG. 15 is a photograph showing DNA recovery using the assays described in Example 4.
Figure 16:
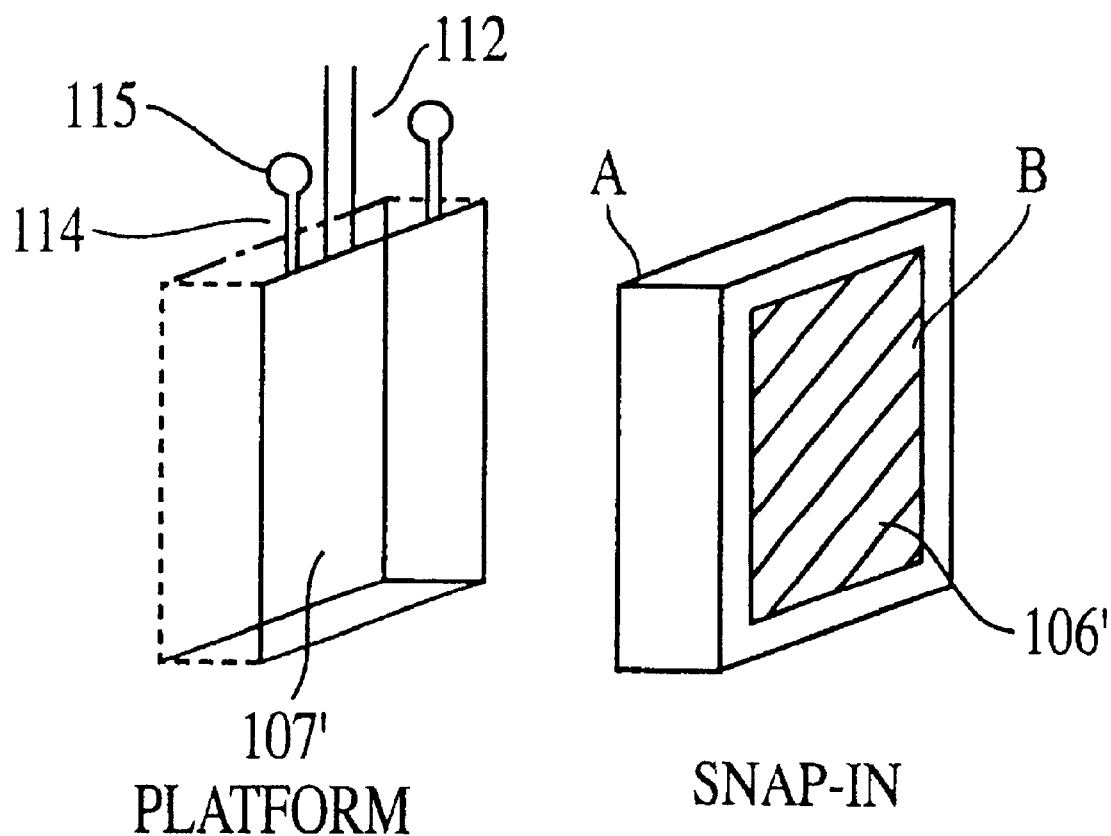
FIG. 16 is a schematic diagram of a snap-in glucose assay component of a Microsystems platform of the invention.
Figure 16:
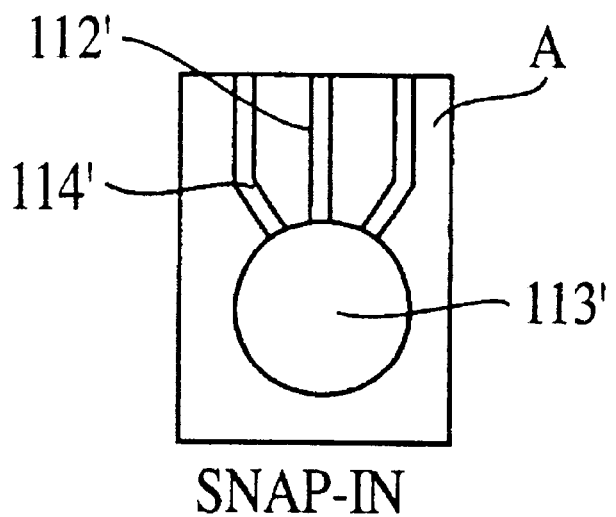

In an alternative embodiment shown in FIG. 15, assay chamber 107 is comprised of a rectangular cavity in the surface of the platform having a depth of from about 0.2 mm to about 3 mm which is fluidly connected at its end proximal to the axis of rotation to capillary 112 and to air displacement channels 114 and ports 115. The second member of the assay chamber is a rectangular piece made from the same material as the platform or other material and designed to snap into the cavity forming liquid-tight seals around all edges. The snap-in piece has two faces, an A face and a B face. The A face consists of a fluid entry channel 112 connected to depression 113; depression 113 is further connected to air displacement channels 114. Depression 113 is from about 0.05 mm to about 5 mm deep and has a dimensions from about 0.5 mm by 4 mm, having a volumetric capacity of from about half to about twice the assay volume applied to the disc. A pad or matrix 106 is attached to the A face of the snap-in piece, comprising a hydrophilic substance possessing a pore size of 0.2–2.0 µm, most preferably comprising a positively-charged nylon matrix having a pore size of about 0.8 µm. The upper limit on pore size of matrix 106 is chosen to inhibit or prevent blood cell entry into the matrix. The matrix is positioned in assay chamber 107 to be in fluidic contact with depression 113, more preferably covering depression 113, and most preferably having a surface area greater than the surface area of depression 113. The matrix is further impregnated with immobilized reagents which produce a detectable product proportional to the amount or concentration of glucose in a blood sample. Most preferably, the detectable product is a colored product, i.e., a product absorbing light at a detectable, most preferably a visible, wavelength.

As illustrated in FIGS. 2A through 2F, in the use of this platform an imprecise volume (ranging from 20–150 µL) of blood was applied to the entry port 101. In embodiments of the platform comprising air displacement channels, the fluid wicked into air channel 114 and was stopped by capillary junction 115. Fluid also wicked into metering capillary 102 and overflow capillary 121. Fluid flowed through the metering capillary 102 and overflow capillary 121 at no rotational speed until the fluid reached capillary junctions at the junction between metering capillary 102 and capillary 110 and overflow capillary 121 and overflow chamber 122. Metering capillary 102 was constructed to define a precise volume from about 15 to about 60 µL of fluid between entry port 101 and capillary junction 111, which was designed to be at least the amount of the fluid placed by the user in entry port 101.

After sample loading by a user and filling of metering capillary 102 and overflow capillary 121 at no rotational speed, the platform was spun at a first rotational speed $f_1$, ranging from about 50 rpm to about 600 rpm, which was sufficient to motivate fluid flow through the overflow capillary 121 in this microfluidics array having an entry port 101 with a depth of from about 0.2 mm to about 3 mm, metering capillary 102 with dimensions of about 0.5 mm×0.5 mm in cross-section and a length of about 2.2–3.8 cm from the center of rotation and an overflow capillary 121 with dimensions of about 0.5 mm×0.5 mm in cross-section and a length of about 5.4 cm from the center of rotation.

Due to the greater distance of the end of overflow capillary 121 from the center of rotation than the end of metering capillary 102, at rotational speed $f_1$ fluid flowed through overflow capillary 121 into overflow chamber 122. The platform was spun until all excess fluid is evacuated from entry port 101 and into overflow chamber 122, except the fluid contained in metering chamber 102.

At a second rotational speed $f_2$ of from about 100 rpm to about 1000 rpm, the precise amount of fluid contained in metering capillary 102 was delivered into assay chamber 107. In embodiments comprising a sacrificial valve 111 in-line with capillary 110 at a position between capillary 110 and 112 shown in FIG. 2B, release of the sacrificial valve resulted in fluid flow through capillary 112 and into assay chamber 107. In said embodiments, fluid flow is achieved at rotational speed $f_2$ with removal of the sacrificial valve. In embodiments of the platforms of the invention comprising capillary valve 111 at a position between capillary 110 and 112 shown in FIG. 2B, capillary 110 preferably filled along with filling of metering capillary 102 until blood reached capillary junction 111 at the junction between capillary 110 and capillary 112; in such embodiments, the capillary junction had a depth of from about 0.03 mm to about 2.2 mm, or at least greater than the depth of capillary 110.

Figure 2A:
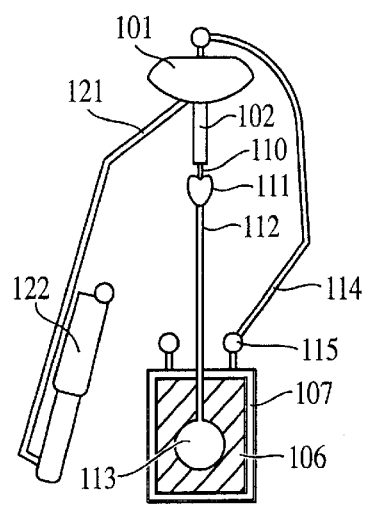
Figure 2B:
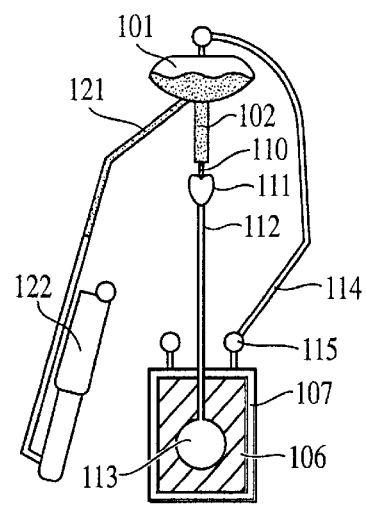
Figure 2C:
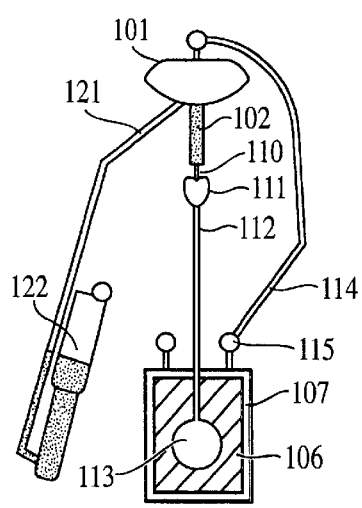

Blood flowing into assay chamber 107 is preferentially directed to depression 113 in the assay chamber; the dimensions of depression 113 are conveniently chosen to be able to contain substantially all of the blood fluid of the sample metered through metering capillary 102 into assay chamber 107 (FIG. 2C). Displaced air flows through air channel 114, and may be vented to the surface of the disc or in communication with blood fluid chamber 104.

As blood flows into depression 113, the fluid component of the blood is driven by pressure and hydrophilic forces into matrix 106; the pore size of the matrix is chosen to prevent the cellular components of the blood from entering the matrix (FIG. 1.4). In preferred embodiment, the cellular component of the blood is retained in depression 113 and the fluid component is efficiently distributed by wicking and by centripetal force into matrix 106. In an alternative embodiment, alternative matrix 118 comprises at least two distinct elements that are compressed or adhered to one another in the assays chamber. The first element is similar to the reagent-containing matrix 106 described above; however, this embodiment of the matrix has a pore size that is not limited by the size of cellular components of the blood, and can be any pore size deemed optimal on experimental, economic, manufacturing or availability grounds. The second element comprises a filtering layer having a pore size that prevents cells and cellular debris from entering this portion of the matrix. In a preferred embodiment, the two elements are rearranged in assay chamber 107 so that second matrix element is in contact with depression 113 wherein the blood aliquot is first contacted with the second matrix component. Blood fluid flows into and through the second matrix element and into the first matrix element, whereby cellular components of blood are prevented from entering assay chamber 107 by the pore size of second matrix element. Preferably, the dimensions of the matrix element is about 1 cm by about 0.75 cm and has a thickness of about 0.05 cm.

As the fluid component of the blood wicks into matrix 106, dried reagents are solubilized and the reaction of the blood component catalyzed by said reagents proceeds. The timescale over which these chemical reactions take place is chosen to be long compared with the time it takes for the fluid component of blood to saturate the matrix 106. The time it takes for the blood fluid to saturate the matrix is dependent on the capacity of the matrix 106 to absorb the fluid and the delivery speed of the blood fluid to the assay chamber 107, which in turn is dependent on the rotational velocity and the cross-sectional dimensions of capillary 110. In preferred embodiments, the reaction(s) goes to completion within about 1 min. Reaction of the blood component(s) with the reagents produce colored product which is then detected (FIG. 2E). In preferred embodiments, detection is performed spectrophotometrically, including absorbance, transmittance, reflection, fluorescence, and chemiluminescence, although visual inspection is also contemplated in alternative embodiments of the invention.

In an alternative embodiment, assay chamber 107 further comprises a detection cell 117 that is laterally adjacent to the portion of assay chamber 107 comprising depression 113 (shown in FIGS. 3A through 3E). This embodiment uses a variation of alternative matrix 118 wherein the matrix comprises a blood separation element and a blood fluid wicking element. These elements are arranged in assay chamber 107 so that the blood separation element is in contact with depression 113 and the blood fluid wicking element is compressed or attached to the blood separation element along its entire extent. A blood fluid wicking element having dimensions as described above and sufficient to encompass the entire surface extent of the blood separation element and to further extend throughout the complete extent of assay chamber 107, including detection cell 117. Reagents are only present in the portion of the blood fluid wicking element in that portion of the element comprising detection cell 117; this arrangement is shown in detail in FIG. 3A.

In the practice of this embodiment of the invention, blood delivered to depression 113 wicks through the blood separation element and into the blood fluid wicking element (FIGS. 3B and 3C). As the region of blood fluid wicking element above depression 113 saturates with blood plasma, the blood fluid wicks laterally into the portion of the matrix 118 comprising detection cell 117 (FIG. 3D). Wetting of this portion of the matrix, which comprises the immobilized reagents and initiates the glucose detection reaction(s) as described in Example 1, with the production of a colored product (FIG. 3E). The amount of colored product produced is detected and the amount of glucose in the blood sample determined thereby.

Another alternative embodiment of a blood glucose assay Microsystems platform is shown in FIGS. 4A through 4E. Construction of the disk embodiments of the platforms of the invention were as described above.

The blood application and metering components and their dimensions and relationships to one another are identical to those described above, comprising sample entry port chamber 201, metering capillary 202, overflow capillary 203, and overflow chamber 205. As in Example 1, each of the overflow and fluid chambers is also connected with air ports or air channels, such as 214, and capillary junction(s) 215, that permit venting of air displaced by fluid movement on the platform.

Metering capillary 202 is fluidly connected to capillary 210 that was from about 0.02 mm to about 2 mm deep and has a cross-sectional diameter of from about 0.02 mm to about 2 mm and is connected to capillary or sacrificial valve 211. Sacrificial or capillary valve 211 is further fluidly connected with capillary 212 that is from about 0.02 mm to about 2 mm deep and has a cross-sectional diameter of from about 0.02 mm to about 2 mm; capillary 212 is further fluidly connected to assay chamber 207. Where capillary 210 is connected with capillary valve 211, said capillary valve 211 is from about 0.03 mm to about 2.2 mm deep and has a cross-sectional diameter of from about 0.03 mm to about 2.2 mm.

Assay chamber 207 comprises a depression in the surface of the platform having a depth of from about 0.2 mm to about 3 mm preferably comprising a circular or rectangular depression 213 connected to capillary 212 and most preferably wherein a metered or otherwise controlled amount of blood can be contained in the assay chamber. Assay chamber 207 also comprises a pad or matrix 206 of a hydrophilic substance possessing a pore size of from about 0.2 to about 2 $\mu$m, most preferably about 0.8 $\mu$m. The upper limit on pore size of matrix 206 is chosen to inhibit or prevent blood cell entry into the matrix, and to promote entry or wicking of the fluid component of blood (plasma or serum) to enter the body of the matrix. The matrix is positioned in assay chamber 207 to be in fluidic contact with depression 213, more preferably covering depression 213, and most preferably having a surface area greater than the surface area of depression 213; in embodiments not having depression 213 as a component of assay chamber 207, the matrix substantially fills the volumetric extent of the assay chamber. The matrix is further impregnated with immobilized reagents which produce a detectable product proportional to the amount or concentration of glucose in a blood sample. Most preferably, the detectable product is a colored product, i.e., a product absorbing light at a detectable, most preferably a visible, wavelength.

In an alternative embodiment, assay chamber 207 comprises a surface wherein reagents 219 are directly dried or otherwise immobilized on the surface of the chamber, and in such embodiments the assay chamber does not comprise matrix 206.

Assay chamber 206 is further fluidly connected with capillary 220 at a position preferably most distal to the axis of rotation. Capillary 220 is from about 0.02 mm to about 2 mm deep and has a cross-sectional diameter of from about 0.02 mm to about 2 mm, and is further fluidly connected with waste reservoir 221. Waste reservoir 221 is positioned from about 1.2 cm to about 14 cm from the axis of rotation, and has a depth in the platform of from about 0.2 mm to about 3 mm. Assay chamber 206 is also fluidly connected with capillary 222 at a position preferably most proximal to the axis of rotation. Capillary 222 is from about 0.02 mm to about 2 mm deep and has a cross-sectional diameter of from about 0.02 mm to about 2 mm, and is further fluidly connected with wash buffer reservoir 223 . Wash buffer reservoir 223 has a depth in the platform of from about 0.2 mm to about 3 mm and is positioned from about 1.2 cm to about 14 cm from the axis of rotation, and in any event more proximal to the axis than assay chamber 206. Fluid flow from wash buffer reservoir 223 through capillary 222 is controlled by either capillary valve 224 or sacrificial valve 225. Where capillary 222 was connected with capillary valve 224, said capillary valve 224 is from about 0.03 mm to about 2.2 mm deep and has a cross-sectional diameter of from about 0.03 mm to about 2.2 mm.

As illustrated in FIGS. 4A through 4D, in the use of this platform an imprecise volume (ranging from 20–150 $\mu$L of fluid) of blood is applied to the entry port 201. Application of blood to the platform and delivering a metered amount of blood to metering capillary 202 was achieved as described above. Alternatively, an unmetered amount of blood is introduced onto the platform directly into assay chamber 207. Preferably, from about 15 $\mu$L to about 150 $\mu$L of blood is delivered to assay chamber 207.

Figure 4A:
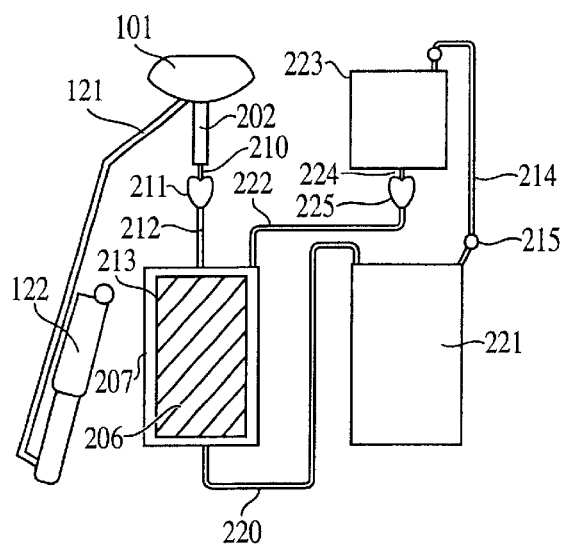
Figure 4B:
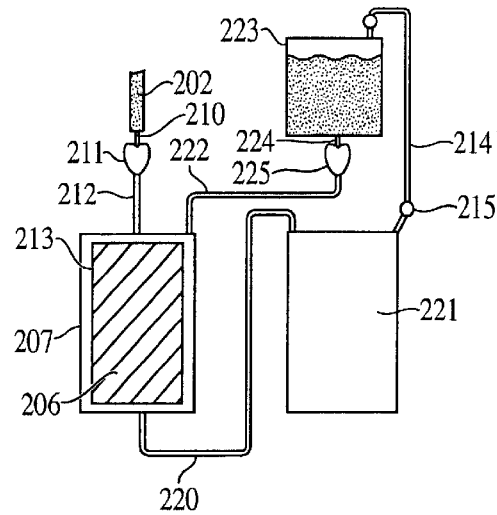
Figure 4C:
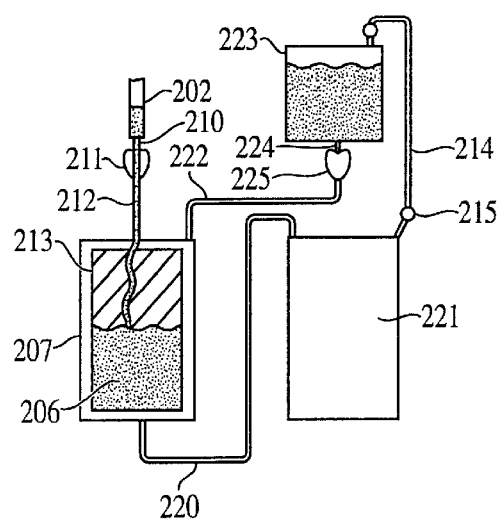

At a rotational speed $f_2$ of about 100–1000 rpm, the precise amount of fluid contained in metering capillary 202 is delivered into assay chamber 207. In embodiments comprising a sacrificial valve 211 in-line with capillary 210 at a position between capillary 210 and assay chamber 207, release of the sacrificial valve results in fluid flow through capillary 212 and into assay chamber 207. In said embodiments, fluid flow is achieved at rotational speed $f_2$ with removal of the sacrificial valve. In embodiments of the platforms of the invention comprising capillary valve 211 at a position between capillary 210 and 212, capillary 210 preferably fills along with filling of blood metering capillary 202 until blood reaches capillary junction 211 at the junction between capillary 210 and capillary 212; in such embodiments, the capillary junction had a depth of from about 0.03 mm to about 2.2 mm. At a rotational speed $f_2$ of about 100–1000 rpm, the fluid contained in blood metering capillary 202 is delivered into assay chamber 207 (FIG. 4C).

Blood flowing into assay chamber 207 is directed to matrix 206 in the assay chamber; the dimensions of matrix 206 are conveniently chosen to be able to contain substantially all of the blood fluid of the sample metered through metering capillary 202 into assay chamber 207. Displaced air flows through air channel 214, and may be vented to the surface of the disc or in communication with blood metering capillary 202 or entry port 201. Alternatively, in embodiments wherein the blood sample is unmetered, the capacity of the matrix 206 is sufficient to absorb a controlled amount of blood. In further alternative embodiments, wherein assay chamber does not comprise matrix 206, the assay chamber is provided having a capacity for a controlled volume of blood.

As blood flows into assay chamber 207, the fluid component of the blood wicks into matrix 206; the pore size of the matrix is chosen to prevent the cellular components of the blood from entering the matrix. In preferred embodiment, the cellular component of the blood is retained in assay chamber 207 and the fluid component is efficiently wicked uniformly throughout matrix 206.

As the fluid component of the blood wicks into matrix 206, dried reagents are solubilized and the reaction of the blood component catalyzed by said reagents proceeds. The timescale over which these reactions take place is chosen to be long compared with the time it takes for the fluid component of blood to saturate the matrix 206; however, in preferred embodiments, the reaction(s) goes to completion within about 0.5 to about 5 min. Reaction of the blood component(s) with reagents produce colored product which is then detected. In preferred embodiments, detection is performed spectrophotometrically, although visual inspection is also contemplated in alternative embodiments of the invention.

Figure 4D:
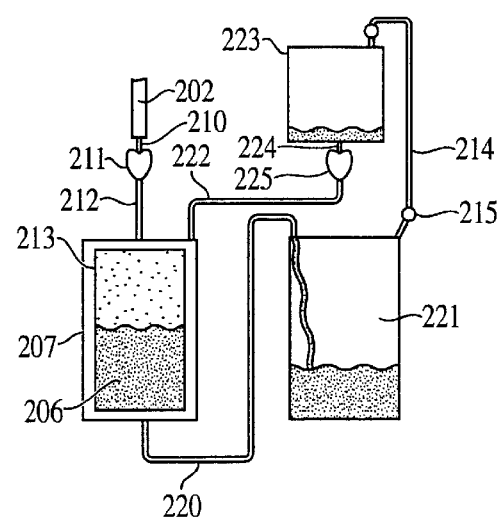

After a time sufficient to produce a detectable amount of a colored product, the wash buffer is released from wash buffer reservoir 223 through capillary 222 and into assay chamber 207. In embodiments comprising a sacrificial valve 225 in-line with capillary 222 at a position between capillary 222 and assay chamber 207, release of the sacrificial valve results in fluid flow through capillary 222 and into assay chamber 207. In said embodiments, fluid flow is achieved at rotational speed $f_3$ of about 250 rpm to about 1500 rpm with removal of the sacrificial valve. In embodiments of the platforms of the invention comprising capillary valve 224 at a position between capillary 222 and assay chamber 207, capillary 222 preferably fills along with filling of blood fluid chamber 204 until blood reached capillary junction 224; in such embodiments, the capillary junction had a depth of from about 0.03 mm to about 2.2 mm. At a higher rotational speed $f_4$ of about 400–2000 $\mu$m, the fluid contained in wash reservoir 223 is delivered into assay chamber 207 (FIG. 4D). Because the fluid flow of wash buffer into the assay chamber and fluid from the assay chamber to the waste chamber is laminar, there is very little mixing of the washing fluid with the fluid initially in the assay chamber. The wash fluid displaces the fluid sample in the assay by pushing it into the waste chamber. The exit of capillary 220 into chamber 221 is at a radial position such that assay chamber 207 must remain filled with fluid during this washing process. The quality of fluid removal is such that no more than 1 part in 1000 of the fluid in the chamber 207 (which has not been imbibed into matrix 206) remains. The fluid which has wicked into matrix 206 is not removed during this wash because of the small pore size of the matrix which resists fluid flow; furthermore, color reagents do not diffuse out of matrix 206 if the wash time is relatively short (less than a few hundred seconds). As a result, interfering blood fluid components such as hemoglobin are removed from chamber 207 while substantially leaving behind color reagents in matrix 206. These are then interrogated spectrophotometrically in assay chamber 207.

Another alternative embodiment of a blood glucose assay microsystems platform is shown in FIGS 5A through 5E. Construction of the disc embodiments of the platforms of the invention were as described above.

The blood application and metering components and their dimensions and relationships to one another are identical to those described above, comprising sample entry port chamber 301, metering capillary 302, overflow capillary 303, and overflow chamber 305. As in Example 1, each of the overflow and fluid chambers is also connected with air ports or air channels, such as 314, and capillary junction(s) 315, that permit venting of air displaced by fluid movement on the platform.

Metering capillary 302 is fluidly connected to capillary 310 that is from about 0.02 mm to about 2 mm deep and has a cross-sectional diameter of from about 0.02 mm to about 2 mm and is connected to capillary or sacrificial valve 311. Sacrificial or capillary valve 311 is further fluidly connected with capillary 312 that is from about 0.02 mm to about 2 mm deep and has a cross-sectional diameter of from about 0.02 mm to about 2 mm, and is further fluidly connected to assay chamber 307. Where capillary 310 is connected with capillary valve 311, said capillary valve 311 is from about 0.03 mm to about 2.2 mm deep and has a cross-sectional diameter of from about 0.03 mm to about 2.2 mm.

Assay chamber 307 comprises a pad or matrix 306 of a hydrophilic substance possessing a pore size of from about 0.2 $\mu$m to about 2 $\mu$m, most preferably about 0.8 $\mu$m. The upper limit on pore size of matrix 306 is chosen to inhibit or prevent blood cell entry into the matrix. The matrix is further impregnated with immobilized reagents which produce a detectable product proportional to the amount or concentration of glucose in a blood sample. Most preferably, the detectable product is a colored product, i.e., a product absorbing light at a detectable, most preferably a visible, wavelength.

As illustrated in FIGS. 5A through 5E, in the use of this platform an imprecise volume (ranging from about 15 $\mu$L to about 150 $\mu$L of fluid) of blood is applied to the entry port 301. Application of blood to the platform and delivering a metered amount of blood to blood metering capillary 302 was achieved as described above. Alternatively, an unmetered amount of blood is introduced onto the platform directly into assay chamber 307, preferably, from about 15 $\mu$L to about 150 $\mu$L.

At a rotational speed $f_1$ of 100–1000 rpm the precise amount of fluid contained in metering chamber 302 is delivered into assay chamber 307. In embodiments comprising a sacrificial valve 311 in-line with capillary 310 at a position between capillary 310 and 312 shown in FIG. 5A, release of the sacrificial valve results in fluid flow through capillary 312 and into assay chamber 307. In said embodiments, fluid flow is achieved at rotational speed $f_1$ with removal of the sacrificial valve. In embodiments of the platforms of the invention comprising capillary valve 311 at a position between capillary 310 and 312 shown in FIG. 5B, capillary 310 preferably fills along with filling of blood metering capillary 302 until blood reaches capillary junction 311 at the junction between capillary 310 and capillary 312; in such embodiments, the capillary junction has a depth of from about 0.03 mm to about 2.2 mm. At a higher rotational speed $f_2$ of about 250 rpm to about 1500 rpm, the fluid contained in blood metering capillary 302 is delivered into assay chamber 307 (FIG. 5C).

Figure 5A:
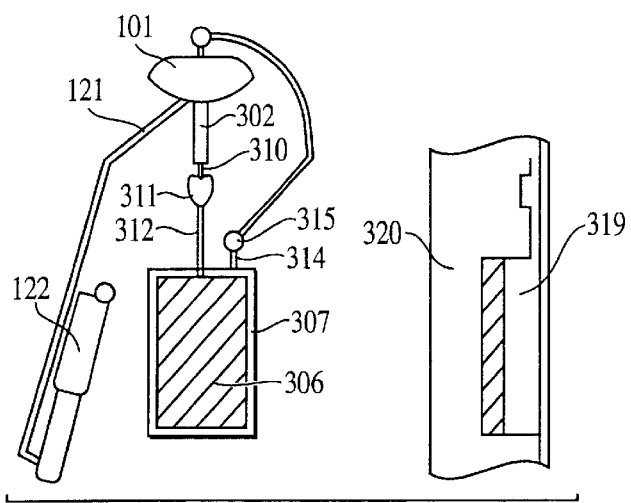
Figure 5B:
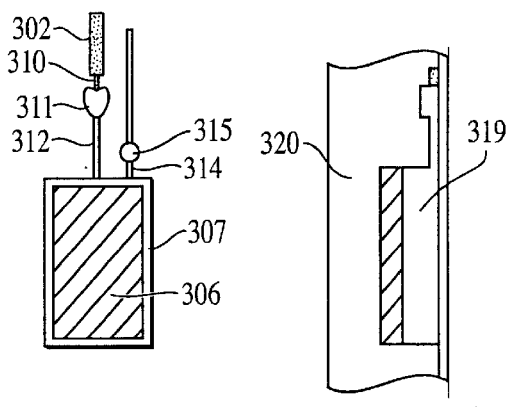
Figure 5C:
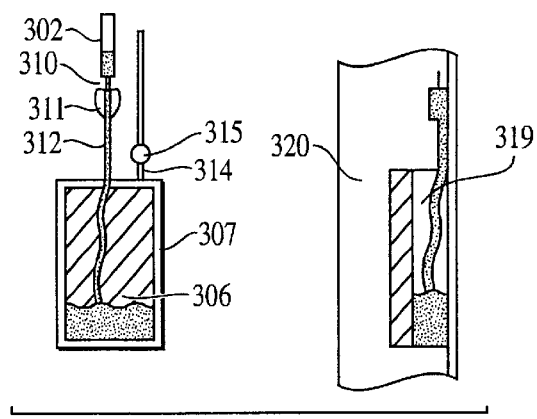

Blood flows into assay chamber 307 with displaced air flowing through air channel 314, and may be vented to the surface of the disc or in communication with blood metering capillary 302 or entry port 301 (FIG. 5C). As blood flows into assay chamber 307, the fluid component of the blood wicks into matrix 306; the pore size of the matrix is chosen to prevent the cellular components of the blood from entering the matrix. In an alternative embodiment, alternative matrix 318 comprises at least two distinct elements that are compressed or adhered to one another in the assays chamber. The first element is similar to the reagent-containing matrix 306 described above; however, this embodiment of the matrix has a pore size that is not limited by the size of cellular components of the blood, and can be any pore size deemed optimal on experimental, economic, manufacturing or availability grounds. The general dimensions of the matrix are equivalent to the dimensions disclosed above, so that the matrices are advantageously standardized and interchangeable on the Microsystems platforms of the invention.

The second element comprises a filtering layer having a pore size that prevents cellular components from entering this portion of the matrix. In a preferred embodiment, these elements are arranged in assay chamber 307 so that the second matrix element is in contact with the surface of assay chamber 307 wherein the blood aliquot is first contacted with the second matrix component. Blood fluid wicks into and through second matrix element and into the first matrix element, whereby cellular components of blood are prevented from entering assay chamber 307 by the pore size of second matrix element.

Figure 5D:
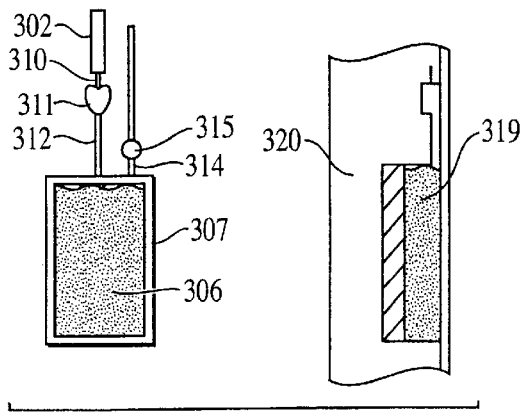
Figure 5E:
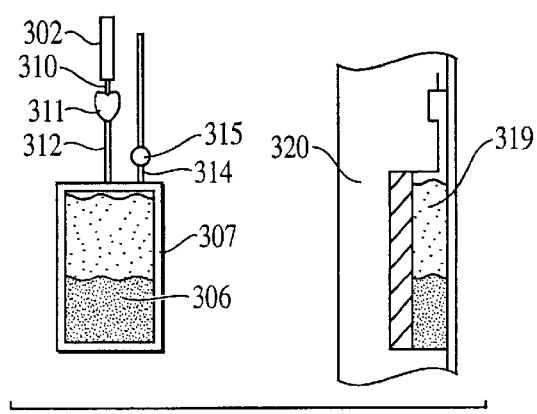

As the fluid component of the blood wicks into matrix 306, dried reagents are solubilized and the reaction of the blood component catalyzed by said reagents proceeds as described below. The timescale over which these reactions take place is chosen to be long compared with the time it takes for the fluid component of blood to saturate the matrix 306; however, in preferred embodiments, the reaction(s) goes to completion within about 0.5 to about 5 min. Reaction of the blood component(s) with reagents produce colored product (FIG. 5D). After sufficient time for the reaction to proceed, the platform is centrifuged at a speed of from about 800 rpm to about 200 rpm, wherein said speed pellets the cellular component of the blood, particularly the red blood cell component thereof, to the "bottom" or most axially distal portion of assay chamber 307. Detection of the colored product of the glucose detecting reaction in matrix 306 is performed at a position in assay chamber 307 radially more proximal to the axis of rotation than the position to which the cellular fraction has been pelleted (FIG. 5E). In preferred embodiments, detection is performed spectrophotometrically, although visual inspection is also contemplated in alternative embodiments of the invention. The amount of colored product produced is detected and the amount of glucose in the blood sample determined thereby.

Another alternative embodiment of a blood glucose assay Microsystems platform is shown in FIGS. 6A through 6E. Construction of the disk embodiments of the platforms of the invention were as described above.

The blood application and metering components and their dimensions and relationships to one another are identical to those described above, comprising sample entry port chamber 401, metering capillary 402, overflow capillary 403, and overflow chamber 405. As in Example 1, each of the overflow and fluid chambers is also connected with air ports or air channels, such as 414, and capillary junction(s) 415, that permit venting of air displaced by fluid movement on the platform.

Metering capillary 402 is fluidly connected to capillary 410 that is from about 0.02 mm to about 2 mm deep and has a cross-sectional diameter of from about 0.02 mm to about 2 mm and is connected to capillary or sacrificial valve 411. Sacrificial or capillary valve 411 is further fluidly connected with capillary 412 that is from about 0.02 mm to about 2 mm deep and has a cross-sectional diameter of from about 0.02 mm to about 2 mm. Capillary 412 is further fluidly connected to cell separation chamber 407. Where capillary 410 is connected with capillary valve 411, said capillary valve 411 is from about 0.02 mm to about 2 mm deep and has a cross-sectional diameter of from about 0.02 mm to about 2 mm.

Cell separation chamber 407 comprised a depression in the surface of the platform having a depth of from about 0.02 mm to about 3 cm, most preferably comprising a circular or rectangular depression 413 connected to capillary 412. Cell separation chamber also comprises a filter 406 consisting of a porous material whose pores are sized (from about 0.2 μm to about 2 μm) to filter red blood cells. Filter 406 is in contact with and more preferably adhered to the surface of cell separation chamber 407 and most extends over depression 413. Blood flowing into cell separation chamber 407 is directed to depression 413 by capillary 412. As depression 413 fills, serum is both wicked and driven by rotation-induced pressure through the filter 406 to the upper surface of cell separation chamber 407, leaving red blood cells and other cellular components trapped beneath filter 406 in depression 413. The volume of blood fluid at the upper surface of cell separation chamber 407 ranges from about 15 μL to about 150 μL.

Cell separation chamber 407 is fluidly connected at a radial position distal from the axis of rotation to capillary 420 that is from about 0.02 mm to about 2 mm deep and has a cross-sectional diameter of from about 0.02 mm to about 2 mm. Capillary 420 is further fluidly connected with assay chamber 421 that is from about 0.02 mm to about 3 cm deep and has a cross-sectional diameter of from about 0.02 mm to about 10 cm. Assay chamber 421 comprises a pad or matrix 422 of a hydrophilic substance possessing any convenient pore size, for example, a pore size of 0.2–2.0 μm, such as a pore size of about 0.8 μm. The matrix is further impregnated with immobilized reagents which produce a detectable product proportional to the amount or concentration of glucose in a blood sample. Most preferably, the detectable product is a colored product, i.e., a product absorbing light at a detectable, most preferably a visible, wavelength.

As illustrated in FIGS. 6A through 6E, in the use of this platform an imprecise volume (ranging from 15 to about 150 μL of fluid) of blood is applied to the entry port 401. Application of blood to the platform and delivering a metered amount of blood to metering capillary 402 was achieved as described in Example 1 above. At a rotational speed $f_1$ of 100–1000 rpm, the precise amount of fluid contained in metering capillary 402 is delivered into assay chamber 407. Alternatively, an unmetered amount of blood is introduced onto the platform directly into assay chamber 407, preferably, from about 15 μL to about 150 μL.

Figure 6A:
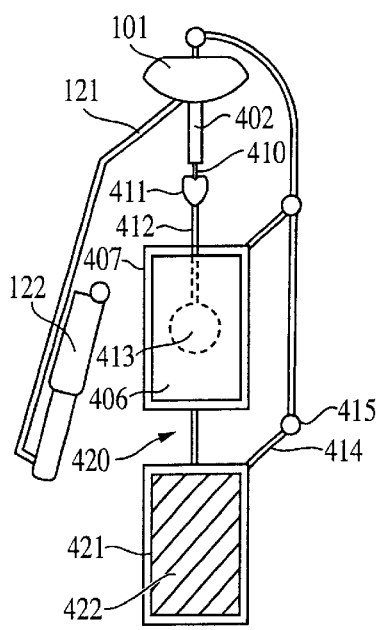
Figure 6B:
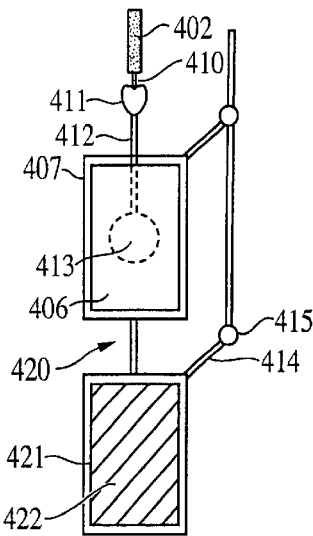

Fluid movement into metering capillary 402 is accompanied by filling of capillary 410. In embodiments comprising a sacrificial valve 411 in-line with capillary 410 at a position between capillary 410 and 412 shown in FIG. 6A, release of the sacrificial valve results in blood fluid flow through capillary 412 and into cell separation chamber 407. In said embodiments, fluid flow is achieved at rotational speed $f_1$ with removal of the sacrificial valve. In embodiments of the platforms of the invention comprising capillary valve 411 at a position between capillary 410 and 412 shown in FIG. 6A, capillary 410 preferably fills along with filling of metering capillary 402 until blood reaches capillary junction 411 at the junction between capillary 410 and capillary 412. In such embodiments, the capillary junction has a depth of from about 0.03 mm to about 2.2 mm. In these embodiments, the fluid contained in metering capillary 402 is delivered into cell separation chamber 407 by rotation of the disc at a higher rotational speed $f_2$ of from about 250 rpm to about 1500 rpm (FIG. 6B).

Figure 6C:
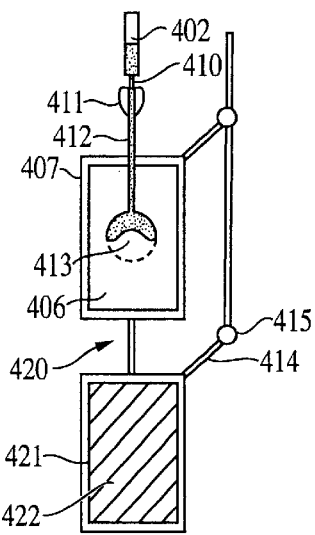
Figure 6D:
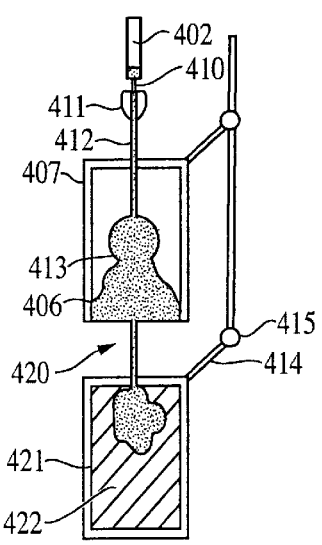

Blood flows into cell separation chamber 407 with displaced air flowing through air channel 414, and may be vented to the surface of the disc or in communication with metering capillary 402 or entry port 401 (FIG. 6C). As blood flows into cell separation chamber 407, the fluid component of the blood wicks into matrix 406; the pore size of the matrix is chosen to prevent the cellular components of the blood from entering the matrix. In a preferred embodiment, matrix 406 is arranged in cell separation chamber 407 so that the matrix is in contact with or more preferably adhered to the lower surface of cell separation chamber 407. Blood fluid, such as plasma or serum, traverses matrix 406 by wicking and under rotation-induced pressure, saturating the matrix and filling a space formed between the top surface of the matrix and the top surface of cell separation chamber 407 (FIG. 6C).

Figure 6E:
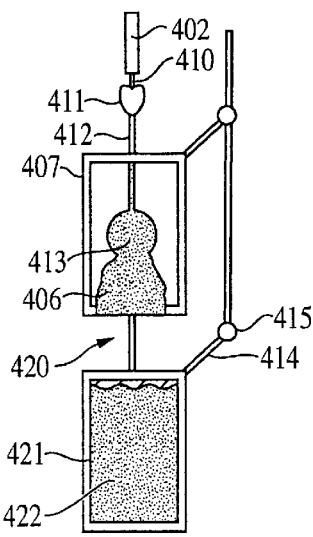

Blood fluid exits cell separation chamber 407 through capillary 420 and flows into assay chamber 421 (FIG. 6D), with displaced air flowing through air channel 414, and may be vented to the surface of the disc or in communication with cell separation chamber 407. Blood fluid flows into assay chamber 421 and wicks into matrix 422. As the blood fluid wicks into matrix 422, dried reagents are solubilized and the reaction of the blood component catalyzed by said reagents proceeds as described below. The timescale over which these reactions take place is chosen to be long compared with the time it takes for the fluid component of blood to saturate the matrix 422; however, in preferred embodiments, the reaction(s) goes to completion within about 0.5 min to about 5 min. Reaction of the blood component(s) with reagents produce a colored product (FIG. 6E). In preferred embodiments, detection of colored product is performed spectrophotometrically, although visual inspection is also contemplated in alternative embodiments of the invention. The amount of colored product produced is detected and the amount of glucose in the blood sample determined thereby.

Another alternative embodiment of a blood glucose assay microsystems platform is shown in FIGS. 7A–7E. Construction of the disk embodiments of the platforms of the invention were as described above.

The blood application and metering components and their dimensions and relationships to one another are identical to those described above, comprising sample entry port chamber 501, metering capillary 502, overflow capillary 503, and overflow chamber 505. As in Example 1, each of the overflow and fluid chambers is also connected with air ports or air channels, such as 514, and capillary junction(s) 515, that permit venting of air displaced by fluid movement on the platform.

Metering capillary 502 is fluidly connected with capillary 510, having a cross-sectional diameter of from about 0.02 mm to about 2 mm and extending from about 1 mm to about 5 cm from the blood fluid chamber. Capillary 510 is also fluidly connected with mixing chamber 515 that is from about 0.02 mm to about 3 cm deep and having a cross-sectional diameter of from about 0.02 mm to about 10 cm, and is positioned from about 1.2 cm to about 14 cm from the center of rotation. Mixing chamber 515 is also fluidly connected with capillary 520 having a cross-sectional diameter of from about 0.02 mm to about 2 mm. Capillary 520 is further fluidly connected with reagent chamber 521, wherein reagents 508 for detecting blood glucose and determining the concentration thereof are stored. Reagent chamber 521 is from about 0.02 mm to about 3 cm deep and having a cross-sectional diameter of from about 0.02 mm to about 10 cm, and is positioned from about 1.2 cm to about 14 cm from the center of rotation. In certain embodiments, reagents 508 are stored on the disc in solution; in these embodiments, fluid flow through capillary 520 is preferably controlled using sacrificial valve 525. In alternative embodiments, reagents 508 are stored in reagent chamber 521 in dry form. In these embodiments, capillary 520 can preferably comprise sacrificial valve 525 or capillary valve 525 positioned between mixing chamber 515 and reagent chamber 521. In these embodiments, reagent chamber 521 further comprises means for a user to add an appropriate amount of a reagent diluent 530, or the platform further comprises diluent chamber 531 fluidly connected to reagent chamber 521 by way of capillary 532. In these embodiments, reagent diluent chamber 531 that is from about 0.02 mm to about 3 cm deep and having a cross-sectional diameter of from about 0.02 mm to about 10 cm, and is positioned from about 1.2 cm to about 14 cm from the center of rotation. In these embodiments, reagents 508 are solubilized in reagent chamber 521 immediately prior to or during use.

Mixing chamber 515 is fluidly connected by capillary channel 536 having a cross-sectional diameter of from about 0.02 mm to about 2 mm and extending from about 1 mm to about 5 cm from the mixing chamber. Capillary channel 536 is further fluidly connected with mixed fluid receiving chamber 537. Mixed fluid chamber 537 is from about 0.02 mm to about 3 cm deep and having a cross-sectional diameter of from about 0.02 mm to about 10 cm, and is positioned from about 1.2 cm to about 14 cm from the center of rotation. Alternatively, capillary 536 is further fluidly connected to second mixing chamber 540. Second mixing chamber 540 is from about 0.02 mm to about 3 cm deep and having a cross-sectional diameter of from about 0.02 mm to about 10 cm, and is positioned from about 1.2 cm to about 14 cm from the center of rotation. Second mixing chamber is fluidly connected by a capillary channel 546 which is further connected with mixed fluid receiving chamber 537. In these embodiments, capillary channel 546 has a cross-sectional diameter of from about 0.02 mm to about 2 mm and extends from about 1 mm to about 5 cm from the second mixing chamber.

Capillary channels 510 and 520, and capillary channels 536 and 546, may be offset in their connection with the mixing chamber(s). As a consequence, fluid flowing through capillary channels 536 and 546 is forced to encounter the opposite wall of mixing chambers 515 and 540 before fluid flow can proceed through further capillary channels. The fluid streams entering a small channel flow in a laminar fashion and therefore mix only by diffusion; the mixing chamber allows the fluids to move in a turbulent fashion and thus mix more effectively. This results in the creation of turbulence in the mixed laminar fluid stream in capillary channels 536 and 546 caused by the conjoint flow of fluid from the input capillaries without appreciable mixing. The turbulence created by the structure of mixing chambers 515 and 540 is sufficient to disrupt laminar flow and cause fluid mixing in the chamber prior to continued fluid flow through capillary channel 546 and into mixed fluid receiving chamber 537.

As illustrated in FIGS. 7A through 7D, in the use of this platform a volume of blood is applied to metering capillary 502, either directly or using the metering components of the platform described above. Fluid enters the each of the capillaries 510 and 520 and stops at capillary junction(s) or sacrificial valve(s) 525.

Figure 7A:
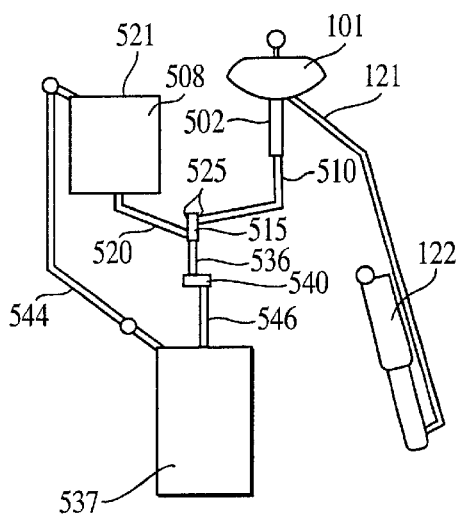
Figure 7B:
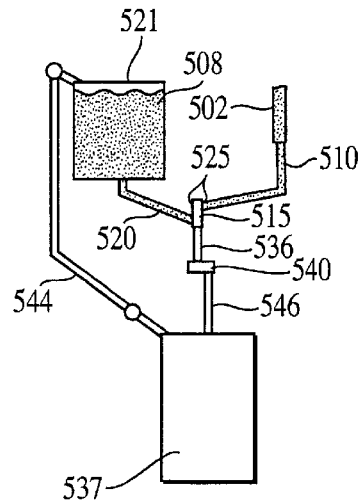

At a rotational speed $f_1$ of 100 to 1000 rpm, the fluids from each capillary flow past capillary junction 525 and through mixing chamber 515 (FIG. 7B). Alternatively, fluid flow is activated by release of sacrificial valves 525. Fluid flow within mixing chamber 515 is turbulent, in contrast to fluid flow through capillaries 510 and 520, which is primarily laminar, so that mixing occurs predominantly in mixing chamber 515. Fluid flow proceeds through channel 536 and then either through second mixing chamber 540 or directly through capillary 546 into mixed fluid receiving chamber 537 (FIG. 7C).

Figure 7C:
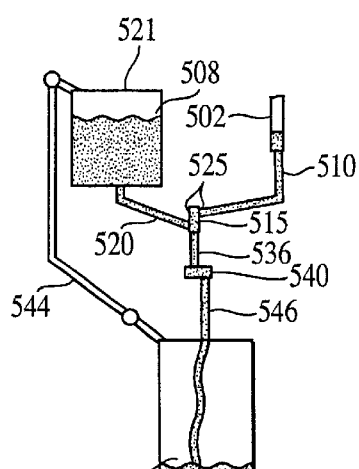
Figure 7D:
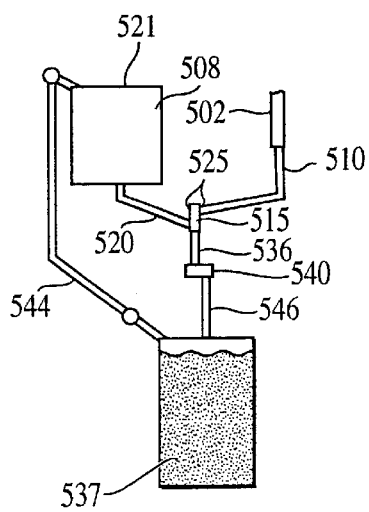
Figure 7E:
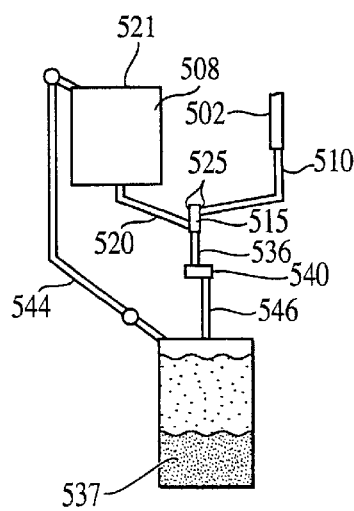

Glucose detection reagents mixed with blood reacts in mixed fluid receiving chamber 537 (FIG. 7C). The timescale over which these reactions take place preferably goes to completion within about 0.5 min to about 5 min. Reaction of the blood component(s) with reagents 508 produce a colored product (FIG. 7D). After sufficient time for the reaction to proceed, the platform is centrifuged at a speed of about 500 rpm to about 300 rpm, wherein said speed pellets the cellular component of the blood, particularly the red blood cell component thereof, to the "bottom" or most axially distal portion of mixed fluid receiving chamber 537. Detection of the colored product of the glucose detecting reaction is performed at a position in mixed fluid receiving chamber 537 radially more proximal to the axis of rotation than the position to which the cellular fraction has been pelleted (FIG. 7D). In preferred embodiments, detection is performed spectrophotometrically, although visual inspection is also contemplated in alternative embodiments of the invention. The amount of colored product produced is detected and the amount of glucose in the blood sample determined thereby.

Another alternative embodiment of a blood glucose assay Microsystems platform is shown in FIGS. 8A through 8D. Construction of the disk embodiments of the platforms of the invention were as described above.

The blood application and metering components and their dimensions and relationships to one another are identical to those described above, comprising sample entry port chamber 601, metering capillary 602, overflow capillary 603, and overflow chamber 605. As in Example 1, each of the overflow and fluid chambers is also connected with air ports or air channels, such as 634, and capillary junction(s) 635, that permit venting of air displaced by fluid movement on the platform.

Metering capillary 602 is fluidly connected to capillary 610 that is from about 0.02 mm to about 2 mm deep and has a cross-sectional diameter of from about 0.02 mm to about 2 mm and is connected to capillary or sacrificial valve 611. Sacrificial or capillary valve 611 is further fluidly connected with capillary 612 that is from about 0.02 mm to about 2 mm deep and has a cross-sectional diameter of from about 0.02 mm to about 2 mm. Capillary 612 is further fluidly connected to cell separation chamber 607. Cell separation chamber 607 is from about 0.02 mm to about 3 cm deep, has a cross-sectional diameter of from about 0.02 mm to about 3 cm, and is positioned from about 1.2 cm to about 14 cm from the center of rotation. Where capillary 610 is connected with capillary valve 611, said capillary valve 611 is from about 0.03 mm to about 2.2 mm deep and has a cross-sectional diameter of from about 0.03 mm to about 2.2 mm.

Cell separation chamber 607 comprises a depression in the surface of the platform having a depth of from about 0.02 mm to about 3 cm, most preferably comprising a circular or concave depression 613 connected to capillary 612. Depression 613 has a depth of from about 0.02 mm to about 1 cm and a volume of from 15 µL to about 150 µL. Cell separation chamber 607 also comprises a filter 606 consisting of a porous material whose pores are sized to filter red blood cells, ranging from about 0.2 µm to about 2 µm. Filter 606 is in contact with and more preferably adhered to the surface of cell separation chamber 607 and most preferably extends over depression 613. Blood flowing into cell separation chamber 607 is directed to depression 613 by capillary 612. As depression 613 fills, serum is both wicked and driven by rotation-induced pressure through the filter 606 to the upper surface of cell separation chamber 607, leaving red blood cells and other cellular components trapped beneath filter 606 in depression 613. The volume of blood fluid at the upper surface of cell separation chamber 607 is from about 15 µL to about 150 µL.

Cell separation chamber 607 is fluidly connected at a radial position distal from the axis of rotation to capillary 620 that is from about 0.02 mm to about 2 mm deep, has a cross-sectional diameter of from about 0.02 mm to about 2 mm and extends from about 1 mm to about 5 cm from cell separation chamber 607. Capillary 620 is further fluidly connected with mixing chamber 615 that is from about 0.02 mm to about 3 cm deep, has a cross-sectional diameter of from about 0.02 mm to about 10 cm, and is positioned from about 1.2 cm to about 14 cm from the center of rotation. Capillary 620 is further fluidly connected with reagent chamber 621, wherein reagents 608 for detecting blood glucose and determining the concentration thereof is stored. Reagent chamber 621 is from about 0.02 mm to about 3 cm deep, has a cross-sectional diameter of from about 0.02 mm to about 10 cm, and is positioned from about 1.2 cm to about 14 cm from the center of rotation. In certain embodiments, reagents 608 are stored on the disc in solution; in these embodiments, fluid flow through capillary 620 is preferably controlled using sacrificial valve 625. In alternative embodiments, reagents 608 are stored in reagent chamber 621 in dry form. In these embodiments, the platform further comprises diluent chamber 631 fluidly connected to reagent chamber 621 by way of capillary 632. Diluent chamber 631 is from about 0.02 mm to about 3 cm deep, has a cross-sectional diameter of from about 0.02 mm to about 10 cm, and is positioned from about 1.2 cm to about 14 cm from the center of rotation. Capillary 632 has a cross-sectional diameter of from about 0.02 mm to about 2 mm, and is positioned from about 1.2 cm to about 14 cm from the center of rotation. In these embodiments, reagents 608 are solubilized in reagent chamber 621 immediately prior to or during use.

Mixing chamber 615 is fluidly connected by capillary channel 636 having a cross-sectional diameter of from about 0.02 mm to about 2 mm and extending from about 1 mm to about 5 cm from the mixing chamber. Capillary channel 636 is further fluidly connected with mixed fluid receiving chamber 637. Mixed fluid chamber 637 is from about 0.02 mm to about 2 mm deep, has a cross-sectional diameter of from about 0.02 mm to about 2 mm, and is positioned from about 1.2 cm to about 14 cm from the center of rotation.

Alternatively, capillary 636 is further fluidly connected to second mixing chamber 640. Second mixing chamber 640 is from about 0.02 mm to about 3 cm deep, has a cross-sectional diameter of from about 0.02 mm to about 10 cm, and is positioned from about 1.2 cm to about 10 cm from the center of rotation. Second mixing chamber is fluidly connected by a capillary channel 646 which is further connected with mixed fluid receiving chamber 637. Capillary channel 646 has a cross-sectional diameter of from about 0.02 mm to about 2 mm and extends from about 1 mm to about 5 cm from the second mixing chamber.

Capillary channels 610 and 620, and capillary channels 636 and 646, may be offset in their connection with the mixing chamber(s). As a consequence, fluid flowing through capillary channels 636 and 646 are forced to encounter the opposite wall of mixing chambers 615 and 640 before fluid flow can proceed through further capillary channels. This results in the creation of turbulence in the mixed laminar fluid stream in capillary channels 636 and 646 caused by the conjoint flow of fluid from the input capillaries without appreciable mixing. The turbulence created by the structure of mixing chambers 615 and 640 is sufficient to disrupt laminar flow and cause fluid mixing in the chamber prior to continued fluid flow through capillary channel 646 and into mixed fluid receiving chamber 637. Mixed fluid receiving chamber 637 is from about 0.02 mm to about 3 cm deep, has a cross-sectional diameter of from about 0.02 mm to about 10 cm, and is positioned from about 1.2 cm to about 14 cm from the center of rotation.

Figure 8A:
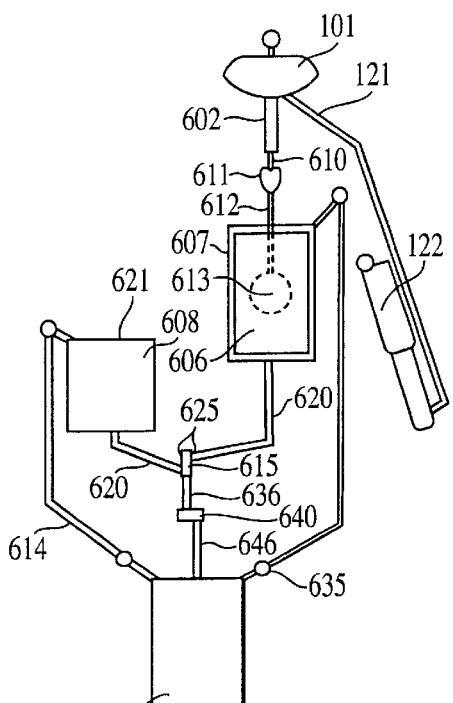
Figure 8B:
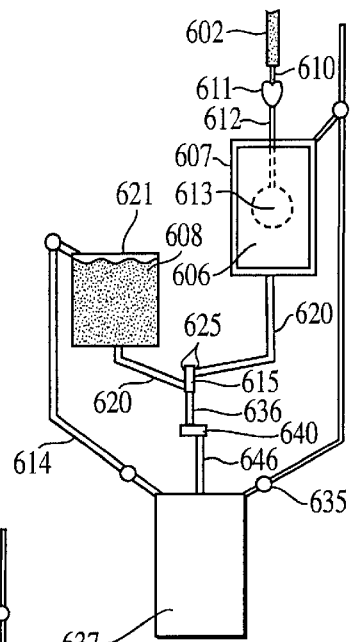
Figure 8C:
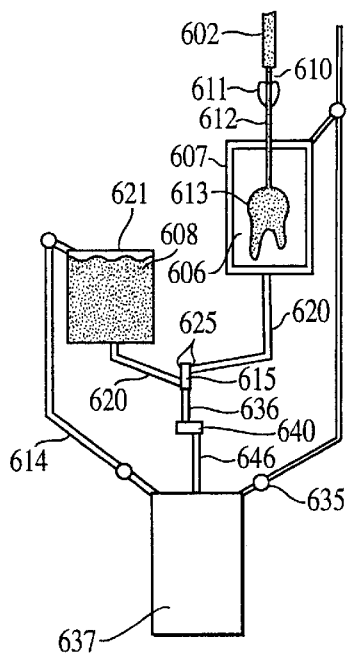

As illustrated in FIGS. 8A through 8E, in the use of this platform a volume of blood is applied to metering capillary 602, either directly or using the metering components of the platform described above. Blood flows into cell separation chamber 607 with displaced air flowing through air channel 654, and may be vented to the surface of the disc or in communication with blood fluid chamber 604 (FIG. 8B). As blood flows into cell separation chamber 607, the fluid component of the blood wicks into matrix 606; the pore size of the matrix (from about 0.2 $\mu$m to about 2 $\mu$m) is chosen to prevent the cellular components of the blood from entering the matrix. In a preferred embodiment, matrix 606 is arranged in cell separation chamber 607 so that the matrix is in contact with or more preferably adhered to the lower surface of cell separation chamber 607. Blood fluid, such as plasma or serum, traverses matrix 606 by wicking and under rotation-induced pressure, saturating the matrix and filling a space formed between the top surface of the matrix and the top surface of cell separation chamber 607 (FIG. 8C).

Figure 8D:
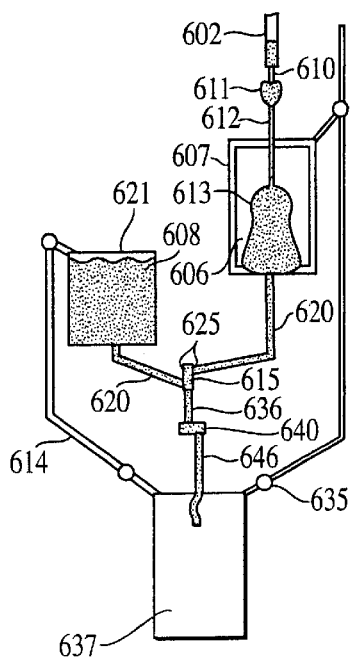
Figure 8E:
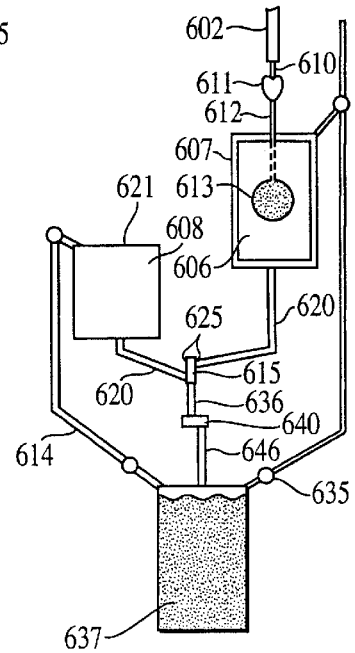

Blood fluid exits cell separation chamber 607 through capillary 620 and flows into mixing chamber 615. Similarly, at a rotational speed of from about 200 rpm to about 2000 rpm sufficient to overcome capillary valve 625, or upon release of sacrificial valve 625, solubilized reagents 608 flow through capillary 620 and into mixing chamber 615. Fluid flow within mixing chamber 615 is turbulent, in contrast to fluid flow through capillaries 610 and 620, which is primarily laminar, so that mixing occurs predominantly in mixing chamber 615. Fluid flow proceeds through channel 636 and then either through second mixing chamber 640 or directly through capillary 646 into mixed fluid receiving chamber 637 (FIG. 8D).

Reaction of the blood component(s) with reagents 608 produce a colored product (FIG. 8E) in the mixed fluid receiving chamber 637. The timescale over which these reactions take place preferably goes to completion within about 0.5 min. to about 5 min. Detection of the colored product of the glucose detecting reaction is performed in mixed fluid receiving chamber 637. In preferred embodiments, detection is performed spectrophotometrically, although visual inspection is also contemplated in alternative embodiments of the invention. The amount of colored product produced is detected and the amount of glucose in the blood sample determined thereby.

The microfluidics structures of the invention are used to detect the amount or concentration of a chemical species in a solution or complex mixture, most preferably an aqueous solution or mixture. In certain preferred embodiments, the chemical species to be detected in glucose in blood. In one embodiment, blood glucose in blood is detected using a hexokinase assay.

In this assay, hexokinase converts glucose to glucose-6-phosphate (G-6-P) in the presence of magnesium cation. G-6-P is then converted to 6-phosphogluconate (6-PG) by glucose-6-phosphate dehydrogenase in the presence of NADP producing a stoichiometric amount of NADPH. NADPH is oxidized by reaction with phenazine methosulfate (PMS) as an intermediate, which is then oxidized by reaction with indotetrotazolium chloride, which forms a colored product that absorbs visible light at 520 nm. Optimum reagent component concentrations vary according to the specifics of the application of this chemical assay, as well understood and practiced by one versed in the art. This reaction scheme is illustrated as follows:

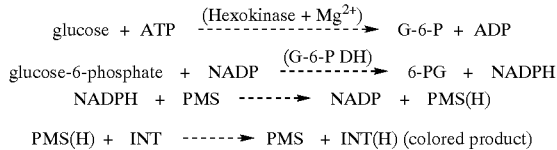

The amount of glucose in the blood fluid is directly related to the amount of reduced indotetrotazolium chloride, and the concentration of reduced indotetrotazolium chloride was related to glucose concentration using light spectroscopy as described below, as understood by those with skill in the art. All of these reagents are preferably provided as dried reagents 108 applied to the disc, for example, comprising matrix 106 shown in FIGS. 1 through 8. These reagents can be lyophilized or air dried directly onto the surface of the disk, for example by "inkjet" methods, or can be applied as dried beads or other particulate components.

In a variation of this reaction scheme, reduction of NADP is assayed directly without the use of PMS or indotetrazolium chloride. In this embodiment, the concentration of oxidized NADP is detected spectrophotometrically by illuminating the sample with light at 340 nm, and detecting absorbance. The amount of glucose in the sample is inversely proportional to the amount of oxidized NADP present in the sample after reaction. In these embodiments, the amount of NADP must be precisely controlled to be certain that the inverse proportionality between oxidized NADP and glucose is maintained.

Detection is performed by transmission, reflection or reflectance spectroscopy. In transmission spectroscopy, light at a wavelength of 520 nm produced by a narrow band light source, most preferably using a light emitting diode (LED) with a filter, enters one face of an assay chamber, ore preferably at a position in the chamber that comprises a detection cell, and the light transmitted through the detection cell is detected using a photomultiplier tube, photodiode, photodiode array, or avalanche photodiode. The photomultiplier tube is calibrated so that the amount of transmitted light detected is interpreted according to Beer's law to determine optical density and hence concentration of glucose in the sample by the well-known linear relation between the logarithm of the incident intensity/transmitted intensity and the concentration of colored (absorbing) product.

Alternatively, production of colored reaction products is detected by reflection spectroscopy. Light at a wavelength of 520 nm is produced by a narrow band light source, most preferably a further combination with a monochromator, grating, or filter. Monochromatic light sources such as lasers or rare gas lamps as well as quasi-monochromatic light sources such as LEDs may also be used and enters one face of an assay chamber, more preferably at a position in the chamber that comprises a detection cell. In preferred embodiments, the face of the assay chamber or detection cell opposite to the face illuminated by the light source comprises a reflective surface, preferably formed using a reflective material, including but not limited to an aluminum layer, a metallized glass, a mirror, and high gloss paint, or a diffusely reflecting surface such as $TiO_2$, underneath the colored fluid, which advantageously decreases the contribution of scratches or rotor wobble. Illuminated light is reflected back through the detection cell at a direct or through an oblique angle and is detected using a photomultiplier tube photodiode, photodiode array, or avalanche photodiode.

For embodiments of the platforms of the invention wherein the assay chamber comprises a solid or porous matrix, production of colored reaction products is most preferably detected by a variation on reflection spectroscopy described above. Light at a wavelength of 520 nm is produced by a narrow band light source, most preferably in further combination with a monochromator is produced that enters one face of an assay chamber, more preferably at a position in the chamber that comprises a detection cell. Light is absorbed from the colored reaction products comprising the matrix and is scattered from the matrix which comprises a diffusely-scattering material. The diffusely scattered, reflected light is detected.

In an alternative reaction protocol, glucose oxidase is used to produce hydrogen peroxide by oxidation of glucose in the blood sample. In this reaction scheme, glucose oxidase converts glucose to gluconic acid and hydrogen peroxide; a twice-stoichiometric amount of hydrogen peroxide is produced relative to the amount of glucose present in the blood sample. The hydrogen peroxide then oxidizes a dye precursor present in the assay chamber or preferably within a detection cell, yielding a colored product. A variety of dye precursors are useful in the practice of this aspect of the invention, including but not limited to O-dianisidine, O-toluidine, O-tolidine, benzidine, 2,2'-azinodi-(3-ethylbenzthiazoline sulfonic acid), 3-methyl-2-benzthiazolinone hydrazone plus N,N-dimethylaniline, phenol plus 4-aminophenzanone, sulfonated 2,4-dichlorophenol plus 4-aminophenzanone, 3-methyl-2-benzothiazolinone hydrazone plus 3-(dimethylamino)benzoic acid, 2-methoxy-4-allyl phenol and 4-aminoantipyrene-dimethylaniline. Optimum reagent component concentration vary according to the specifics of the application of this chemical assay, as well understood and practiced by one versed in the art. This reaction scheme is illustrated as follows:

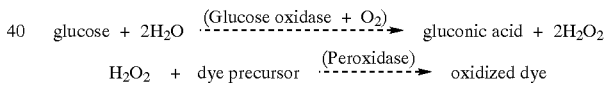

The amount of glucose in the blood fluid is directly related to the amount of oxidized dye produced. The concentration of oxidized dye produced is determined by Beers law and light spectroscopy measurements. The total amount of oxidized dye produced is then used to calculate the sample glucose concentration. Alternatively and preferably, the rate of oxidized dye production is measured and that rate related to the sample glucose concentration. Calibration, to relate glucose concentration to optical measurements calculated by either method above, are well understood by one versed in this art. All of these reagents are preferably provided as dried reagents 108 applied to the disc; for example, comprising matrix 106 shown in FIGS. 1 through 8. These reagents can be applied, by for example methods, including but not limited to, filling, spraying, dipping, rolling and stamping a solution containing reagent components followed by lyophilization or air drying. Several applications may be made sequentially, with different components.

Figure 9:
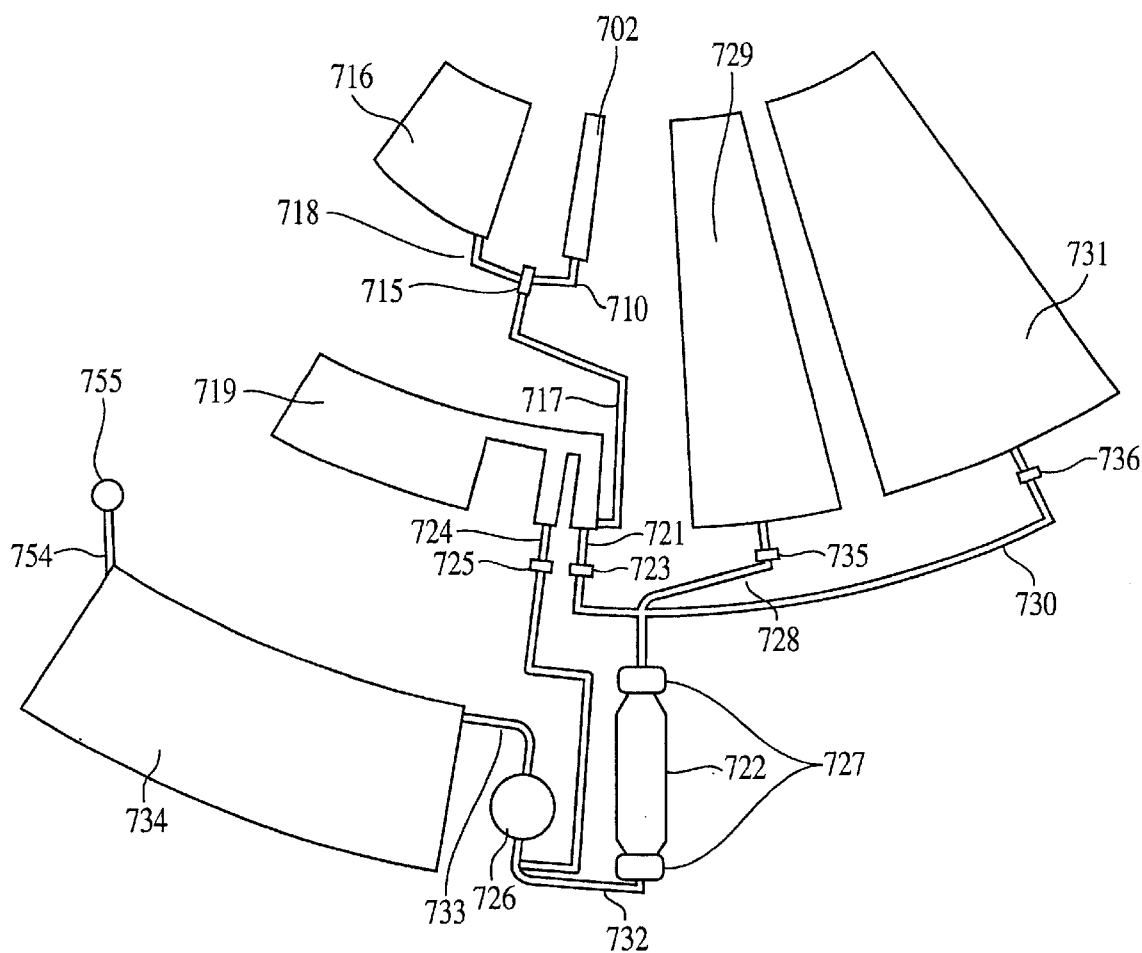
FIGS. 9 through 11 are schematic representations of microfluidics arrays and components for performing separations of analyte from a fluid sample using the Microsystems platforms of the invention.

The invention also provides microsystem platforms for performing separations of particular components of a solution or complex mixture. In particular, the invention provides disc embodiments of the platforms of the invention comprising separation chambers containing components or matrices that specifically bind and retain particular chemical species comprising a chemical solution or complex mixture. This aspect of the invention is illustrated by a microfluidics array for separating glycated hemoglobin from a blood sample, as shown in FIG. 9.

Construction of the disk embodiments of the platforms of the invention were as described above. The blood application and metering components and their dimensions and relationships to one another are identical to those described above, comprising sample entry port chamber 701, metering capillary 702, overflow capillary 703, and overflow chamber 705. As in Example 1, each of the overflow and fluid chambers is also connected with air ports or air channels, such as 754, and capillary junction(s) 755, that permit venting of air displaced by fluid movement on the platform.

Metering capillary 702 is fluidly connected to capillary 710 that is from about 0.02 mm to about 2 mm deep and has a cross-sectional diameter of from about 0.02 mm to about 2 mm. Capillary 710 is further fluidly connected to mixing chamber 715 that is from about 0.02 mm to about 3 cm deep, has a cross-sectional diameter of from about 0.02 mm to about 10 cm, and is positioned from about 1.2 cm to about 14 cm from the center of rotation. Lysis buffer chamber 716 containing blood lysis buffer is from about 0.02 mm to about 3 cm deep, has a cross-sectional diameter of from about 0.02 mm to about 10 cm, and is positioned from about 1.2 cm to about 14 cm from the center of rotation. Lysis buffer chamber 716 is positioned more proximally to the axis of rotation that mixing chamber 715, and has a volumetric capacity of from about 15 $\mu$L to about 150 $\mu$L of lysis buffer, composed of 0.1% Triton X100 in 50 mM Tris pH 9.5. Lysis buffer chamber 715 is fluidly connected through capillary 718 to mixing chamber 715.

Mixing chamber 715 is fluidly connected to capillary 717 that is from about 0.02 mm to about 2 mm deep and has a cross-sectional diameter of from about 0.02 mm to about 2 mm and is connected to secondary metering structure 719. Secondary metering structure 719 is from about 0.02 mm to about 3 cm deep, and is positioned from about 1.2 cm to about 14 cm from the center of rotation. Secondary metering structure 719 is constructed to comprise three sections. A first metering section is arranged proximal to the entry position of capillary 717 and is separated from a second metering section by a septum that extends from the distal wall of the structure to a position just short of the proximal wall of the structure. This arrangement produces a fluid connection between the first metering section having a volumetric capacity of from about 5 $\mu$L to about 15 $\mu$L and second metering section having a volumetric capacity of from about 5 $\mu$L to about 15 $\mu$L. An overflow chamber is positioned adjacent to the second metering section and separated by a septum that extends from the distal wall of the structure to a position just short of the proximal wall of the structure. This arrangement produces a fluid connection between the second metering section and the overflow sections of the secondary metering structure 719.

Capillary 721 is in fluid connection with secondary metering structure 719 at the distal wall of the first metering section. Capillary 721 is from about 0.02 mm to about 2 mm deep and has a cross-sectional diameter of from about 0.02 mm to about 2 mm and is fluidly connected to boronate affinity matrix chamber 722. Boronate affinity matrix chamber 722 is from about 0.02 mm to about 0.3 cm deep, has a cross-sectional diameter of from about 0.02 mm to about 10 cm and is positioned from about 1.2 cm to about 14 cm from the axis of rotation. Boronate affinity matrix chamber 722 further comprises 20–50 $\mu$L boronate-functionalized agarose beads having a mean diameter of about 60 $\mu$m; the beads are maintained in the chamber 722 using a porous frit 727. Fluid flow through capillary 721 is connected to capillary or sacrificial valve 723. Capillary 724 is in fluid connection with secondary metering structure 719 at the distal wall of the second metering section. Capillary 724 is from about 0.02 mm to about 2 mm deep and has a cross-sectional diameter of from about 0.02 mm to about 2 mm and is connected to read window 726. Read window 726 is from about 0.02 mm to about 3 cm deep, has a cross-sectional diameter of from about 0.02 mm to about 10 cm and is positioned from about 1.2 cm to about 14 cm from the axis of rotation. Read window is comprised of a material transparent to light at a wavelength of about 430 nm. Fluid flow through capillary 724 is connected to capillary or sacrificial valve 725.

Boronate affinity matrix chamber 722 is further fluidly connected to capillary 728. Capillary 728 is from about 0.02 mm to about 2 mm deep and has a cross-sectional diameter of from about 0.02 mm to about 2 mm and is connected to column preparation buffer reservoir 729. Column preparation buffer reservoir 729 is from about 0.02 mm to about 3 cm deep and has a cross-sectional diameter of from about 0.02 mm to about 10 cm and is positioned from about 1.2 cm to about 12 cm from the axis of rotation, more proximal than boronate affinity matrix chamber 722. Column preparation buffer reservoir 729 comprises from about 100 $\mu$L to about 500 $\mu$L of column preparation buffer comprising magnesium chloride, taurine, D,L-methionine, sodium hydroxide, antibiotics and stabilizers (obtained from IsoLab as described in the Examples below). Fluid flow through capillary 728 is connected to capillary or sacrificial valve 735.

Boronate affinity matrix chamber 722 is further fluidly connected to capillary 730. Capillary 730 is from about 0.02 mm to about 2 mm deep and has a cross-sectional diameter of from about 0.02 mm to about 2 mm and is connected to column wash buffer reservoir 731. Column wash buffer reservoir 731 is from about 0.02 mm to about 3 cm deep and has a cross-sectional diameter of from about 0.02 mm to about 10 cm and is positioned from about 1.2 cm to about 14 cm from the axis of rotation, more proximal than boronate affinity matrix chamber 722. Column wash buffer reservoir 731 comprises from about 100 $\mu$L to about 500 $\mu$L of column preparation buffer as described above. Fluid flow through capillary 730 is connected to capillary or sacrificial valve 736.

Figure 9A:
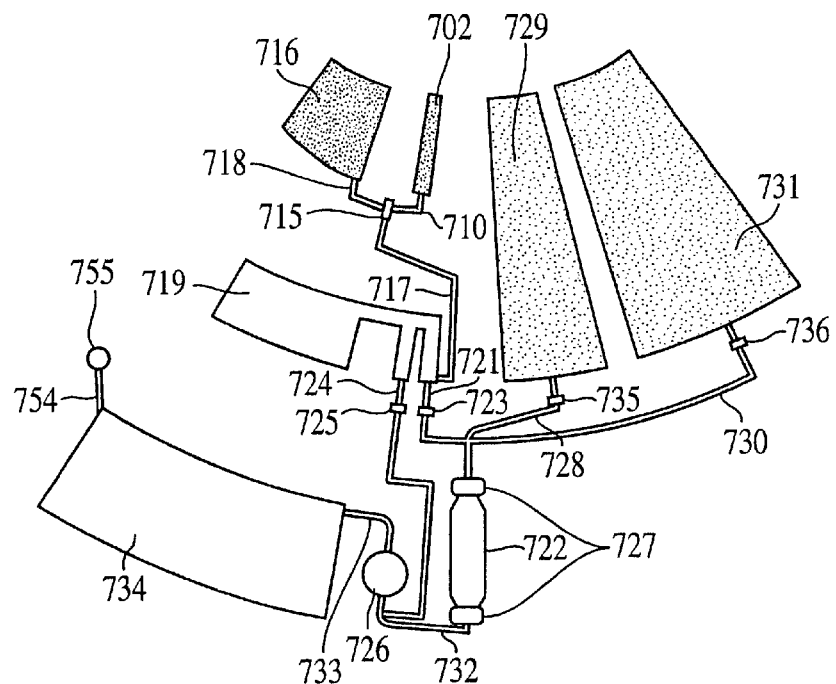
Figure 9B:
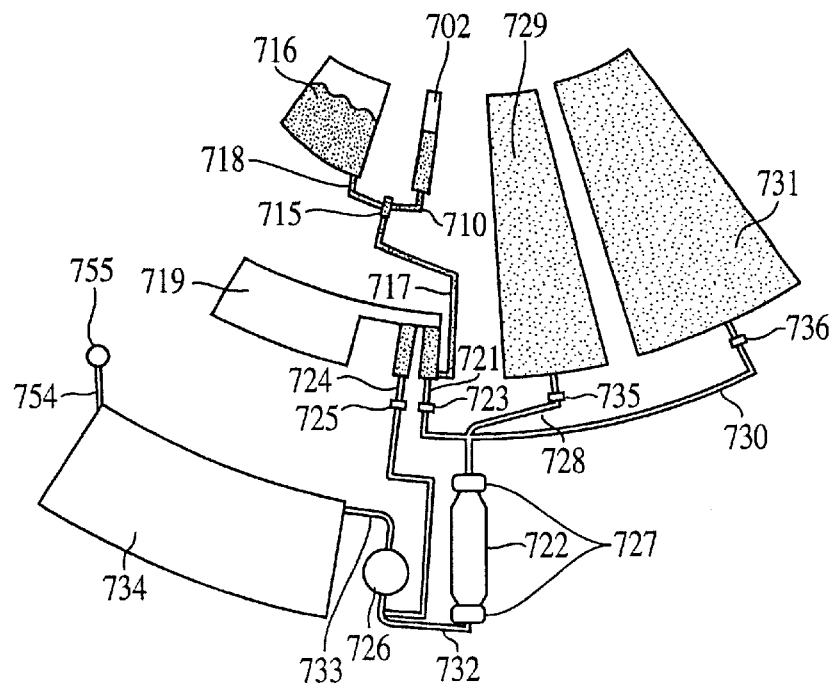
Figure 9C:
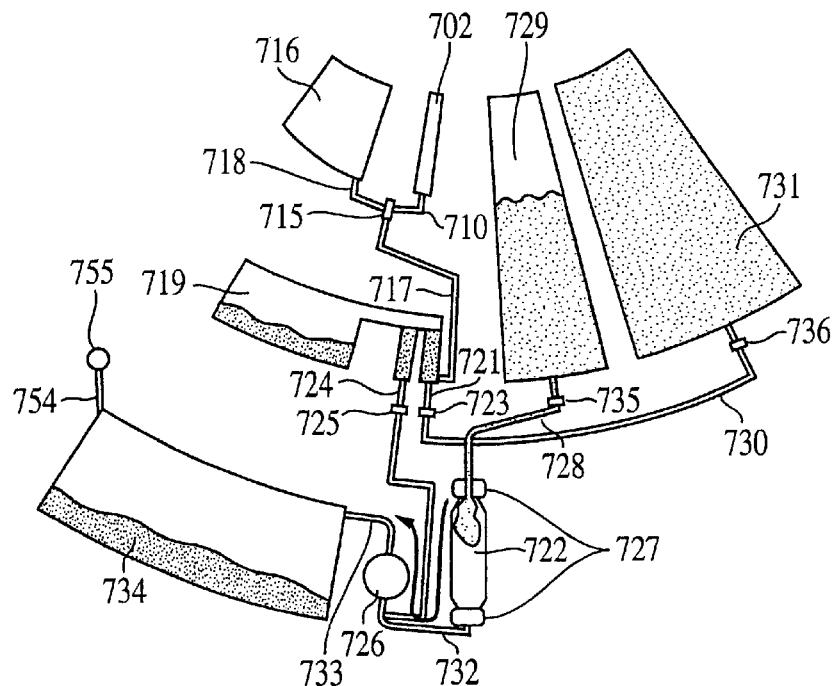
Figure 9D:
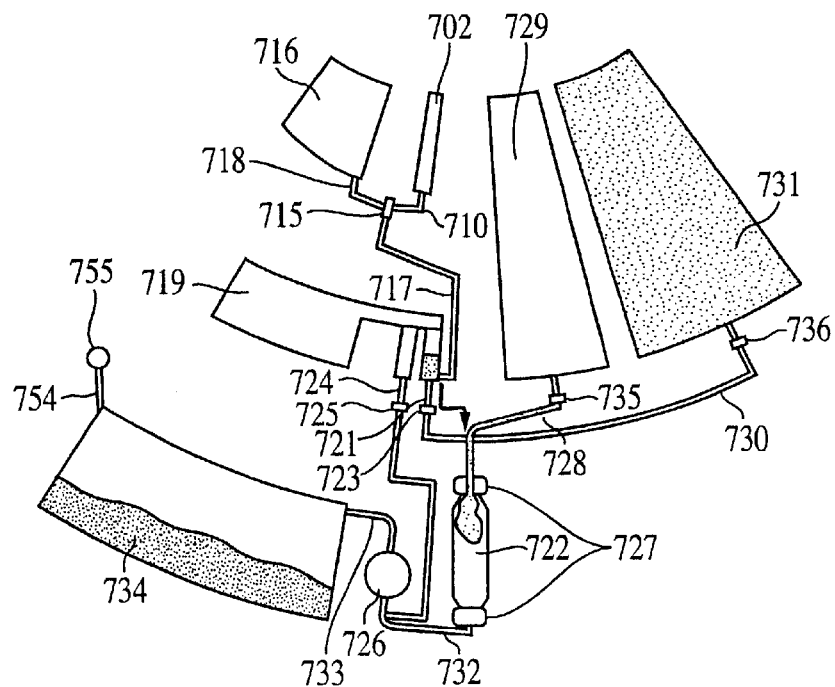
Figure 9E:
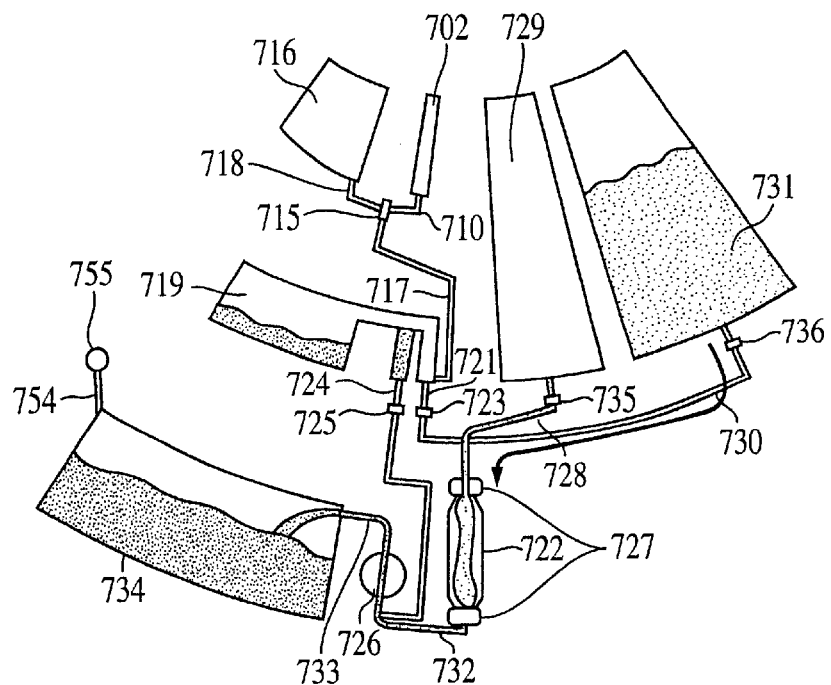
Figure 9F:
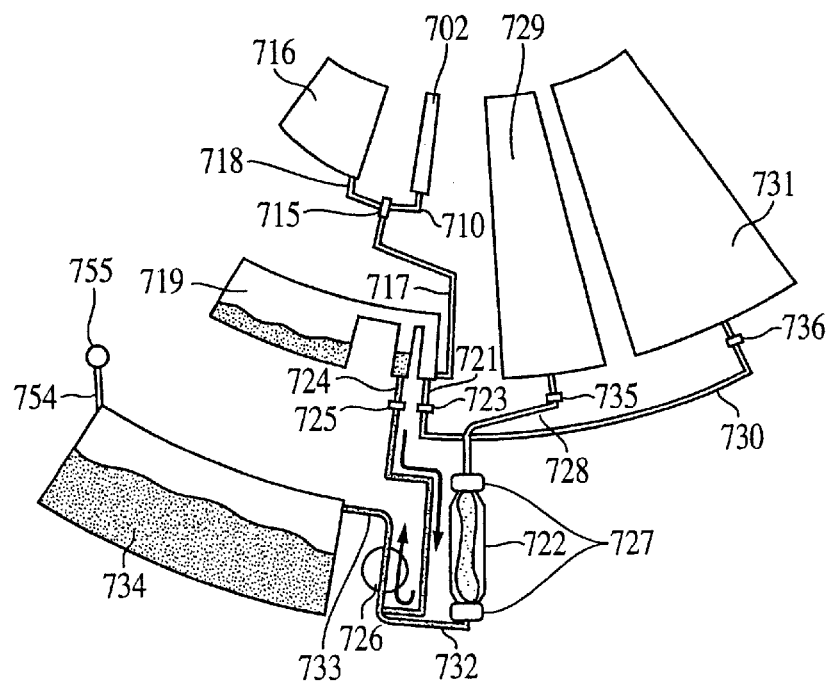

In alternative embodiments, column preparation buffer reservoir 729 and column wash buffer reservoir 731 can be the same reservoir, or can be fluidly connected as shown in FIG. 9A.

Boronate affinity matrix chamber 722 is further fluidly connected to capillary 732. Capillary 732 is from about 0.02 mm to about 2 mm deep and has a cross-sectional diameter of from about 0.02 mm to about 2 mm and is connected to read window 726.

Read window 726 is further fluidly connected to capillary 733. Capillary 733 is from about 0.02 mm to about 2 mm deep and has a cross-sectional diameter of from about 0.02 mm to about 2 mm and is connected to waste reservoir 734. Waste reservoir 734 is from about 0.02 mm to about 3 cm deep and has a cross-sectional diameter of from about 0.02 mm to about 10 cm and is positioned from about 1.2 cm to about 14 cm from the axis of rotation.

As illustrated in FIG. 9, in the use of this platform a volume of blood from about 15 $\mu$L to about 150 $\mu$L is applied to metering capillary 702, either directly or using the metering components of the platform described above. Blood flowing through capillary 710 and lysis buffer flowing through capillary 718 are mixed in mixing chamber 715 by overcoming capillary valve 711 or release of sacrificial valve 711. A volume of lysis buffer from about 25 μL to about 90 μL was mixed with the blood sample. Fluid flow within mixing chamber 715 is turbulent, in contrast to fluid flow through capillaries 710 and 718, which is primarily laminar, so that mixing occurs predominantly in mixing chamber 715. Fluid flow proceeds through channel 717 and into secondary metering structure 719.

The mixture of lysis buffer and blood, comprising a lysed blood sample, flows at a rotational speed $f_2$ from about 200 rpm to about 2000 rpm into secondary metering structure 719. The lysed blood sample enters and fills the first section of secondary metering structure 719. Continued lysed blood sample flow into secondary metering structure 719 then fills the second section of secondary metering structure 719. Any additional lysed blood sample then empties into the overflow chamber of secondary metering structure 719. Most preferably, a sufficient volume of lysis buffer and blood sample is applied to the disc to fill at least the first and second metered sections of secondary metering structure 719.

After the lysed blood sample is completely transferred to secondary metering structure 719, capillary or sacrificial valve 735 is released, allowing from 100 μL to about 500 μL of column preparation buffer to flow at rotational speed $f_2$ through capillary 730 and into boronate affinity matrix 722. Continued or discontinuous rotation motivates column preparation buffer through boronate affinity matrix 722, capillary 732, read window 726, capillary 733 and into waste reservoir 734.

After the column preparation buffer is applied to boronate affinity matrix chamber 722, capillary or sacrificial valve 723 is released, allowing the metered lysed blood sample from the first metered section of secondary metering structure 719 through capillary 721 and into boronate affinity matrix 722 and allowed to incubate in the affinity matrix chamber for from about 0.5 to about 5 min. Capillary or sacrificial valve 736 is then released, allowing from 100 μL to about 500 μL of column wash buffer to flow at rotational speed $f_2$ through capillary 730 and into boronate affinity matrix 722. Continued or discontinuous rotation motivates column preparation buffer through boronate affinity matrix 722, capillary 732 and into read window 726. During fluid flow of wash buffer through the boronate affinity matrix chamber, read window is preferably illuminated by light at a wavelength of 430 nm and the concentration of hemoglobin in the sample after glycated hemoglobin has been removed by the boronate affinity matrix is determined thereby.

Capillary or sacrificial valve 725 is released at rotational speed $f_3$ of from about 100–1000 rpm and the metered lysed blood sample from the second metered section of secondary metering structure 719 flows through capillary 724 and into read window 726. Read window is then illuminated by light at a wavelength of 430 nm and the concentration of hemoglobin in the sample determined transmission, reflection, or reflectance spectroscopy. The amount of glycated hemoglobin in the sample is determined by subtracting the amount of hemoglobin obtained in the first reading from the amount of hemoglobin obtained in the second reading.

An alternative embodiment of the glycated hemoglobin assay microsystem platform of the invention is shown in FIG. 10. Construction of the disk embodiments of the platforms of the invention were as described above. The blood application and metering components and their dimensions and relationships to one another are identical to those described above, comprising sample entry port chamber 801, metering chamber 802, overflow capillary 803, and overflow chamber 805. As in Example 1, each of the overflow and fluid chambers is also connected with air ports or air channels, such as 854, and capillary junction(s) 855, that permit venting of air displaced by fluid movement on the platform.

Metering capillary 802 is fluidly connected to capillary 810 that is about 0.02 mm to about 2 mm deep and has a cross-sectional diameter of from about 0.02 mm to about 2 mm. Capillary 810 is further fluidly connected to mixing chamber 815 that is from about 0.02 mm to about 3 cm deep, has a cross-sectional diameter of from about 0.02 mm to about 10 cm, and is positioned from about 1.2 cm to about 14 cm from the center of rotation. Lysis buffer chamber 816 containing blood lysis buffer is from about 0.02 mm to about 3 cm deep, has a cross-sectional diameter of from about 0.02 mm to about 10 cm, and is positioned from about 1.2 cm to about 14 cm from the center of rotation. Lysis buffer chamber 816 is positioned more proximally to the axis of rotation than mixing chamber 815, and has a volumetric capacity of from about 15 μL to about 150 μL of lysis buffer, composed of 0.1% Triton X100 in 50 mM Tris pH 9.5. Lysis buffer chamber 815 is fluidly connected through capillary 818 to mixing chamber 815.

Mixing chamber 815 is fluidly connected to capillary 817 that is from about 0.02 mm to about 2 mm deep and has a cross-sectional diameter of from about 0.02 mm to about 2 mm and is connected to secondary metering structure 819. Secondary metering structure 819 is from about 0.02 mm to about 3 cm deep, and is positioned from about 1.2 cm to about 14 cm from the center of rotation. Secondary metering structure 819 is constructed to comprise two sections. A metering section is arranged proximal to the entry position of capillary 817 and is separated from an overflow section by a septum that extends from the distal wall of the structure to a position just short of the proximal wall of the structure. This arrangement produces a fluid connection between the metering section having a volumetric capacity of from about 5 μL to about 15 μL and the overflow chamber.

Capillary 821 is in fluid connection with secondary metering structure 819 at the distal wall of the first metering section. Capillary 821 is from about 0.02 mm to about 2 mm deep and has a cross-sectional diameter of from about 0.02 mm to about 2 mm and is fluidly connected to boronate affinity matrix chamber 822. Boronate affinity matrix chamber 822 is from about 0.02 mm to about 0.3 cm deep, has a cross-sectional diameter of from about 0.02 mm to about 10 cm and is positioned from about 1.2 cm to about 14 cm from the axis of rotation. Boronate affinity matrix chamber 822 further comprises 20–50 μL boronate-functionalized agarose beads having a mean diameter of about 60 cm; the beads are maintained in the chamber 822 using a porous frit 827. Boronate affinity matrix chamber 822 further comprises at least one surface that is translucent to light of at least wavelength of about 430 nm, permitting direct illumination and interrogation of the amount of glycated hemoglobin that is bound thereto. Fluid flow through capillary 821 is connected to capillary or sacrificial valve 823.

Boronate affinity matrix chamber 822 is further fluidly connected to capillary 828. Capillary 828 is from about 0.02 mm to about 2 mm deep and has a cross-sectional diameter of from about 0.02 mm to about 2 mm and is connected to column preparation buffer reservoir 829. Column preparation buffer reservoir 829 is from about 0.02 mm to about 3 cm deep and has a cross-sectional diameter of from about 0.02 mm to about 10 cm and is positioned from about 1.2 cm to about 12 cm from the axis of rotation, more proximal than boronate affinity matrix chamber 822. Column preparation buffer reservoir 829 comprises from about 100 μL to about 500 μL of column preparation buffer comprising magnesium chloride, taurine, D,L-methionine, sodium hydroxide, antibiotics and stabilizers (obtained from IsoLab as described in the Examples below). Fluid flow through capillary 828 is connected to capillary or sacrificial valve 835.

Boronate affinity matrix chamber 822 is further fluidly connected to capillary 830. Capillary 830 is from about 0.02 mm to about 2 mm deep and has a cross-sectional diameter of from about 0.02 mm to about 2 min and is connected to column wash buffer reservoir 831. Column wash buffer reservoir 831 is from about 0.02 mm to about 3 cm deep and has a cross-sectional diameter of from about 0.02 mm to about 10 cm and is positioned from about 1.2 cm to about 14 cm from the axis of rotation, more proximal than boronate affinity matrix chamber 822. Column wash buffer reservoir 831 comprises from about 100 μL to about 500 μL of column preparation buffer as described above. Fluid flow through capillary 830 is connected to capillary or sacrificial valve 836.

Figure 10A:
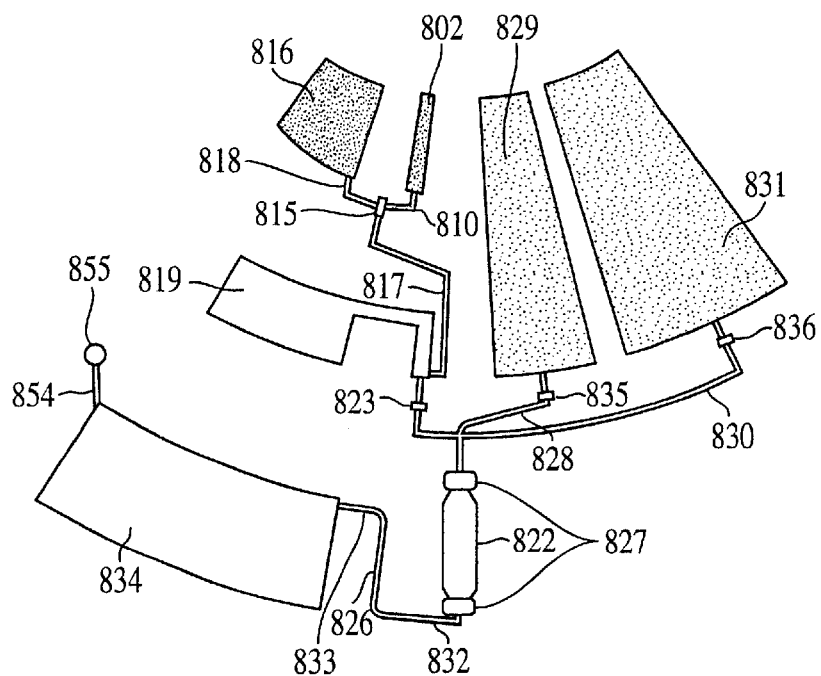
Figure 10B:
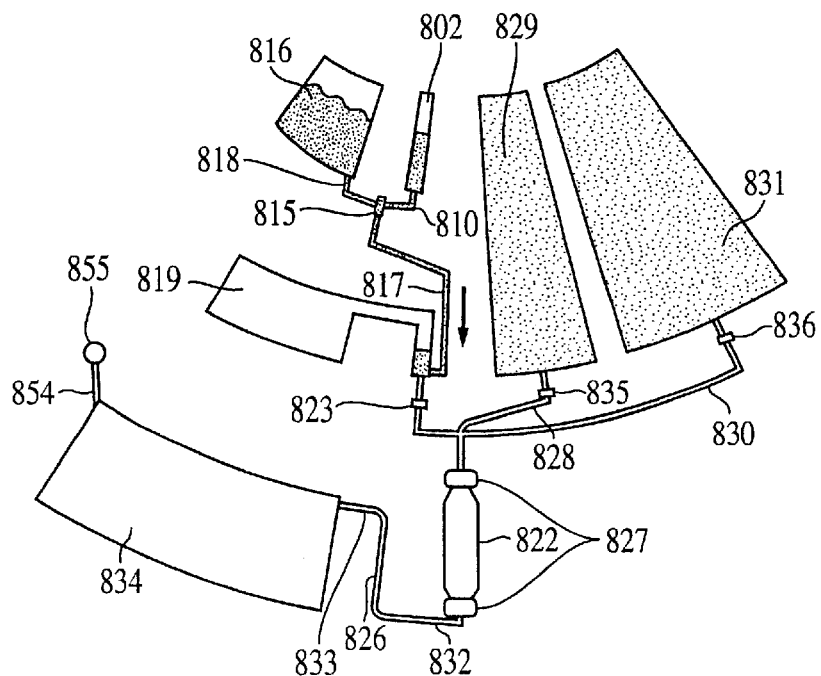
Figure 10C:
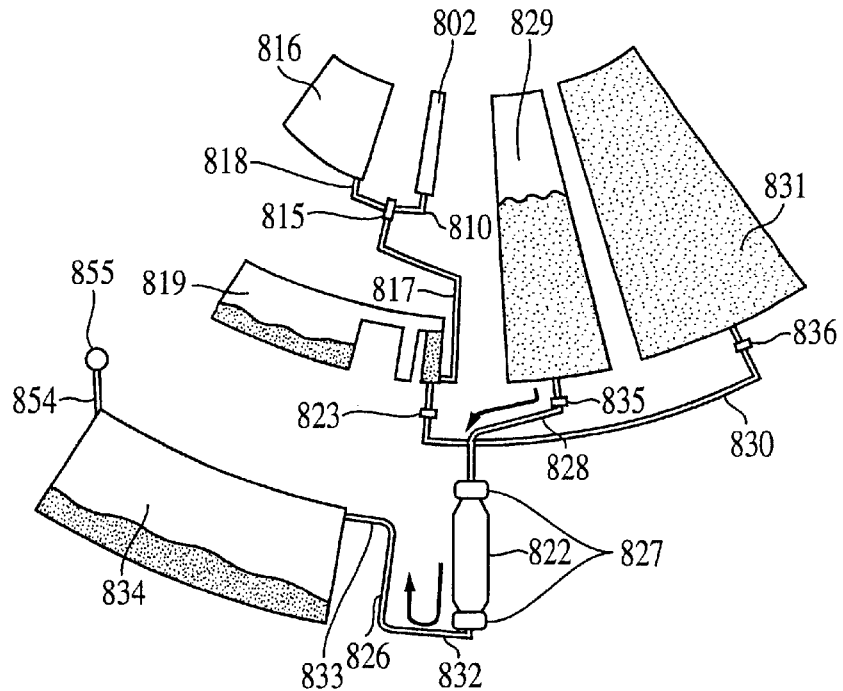
Figure 10D:
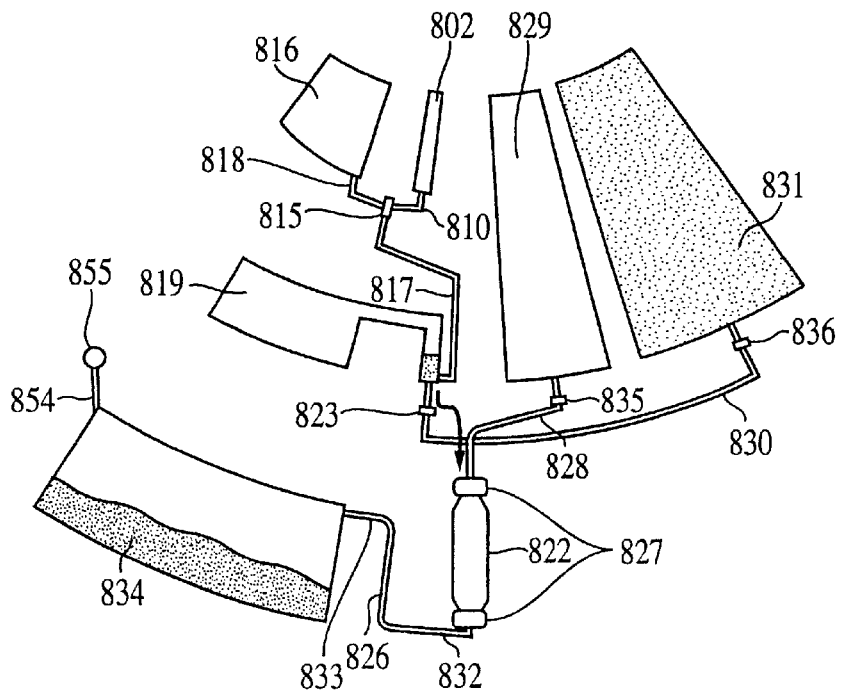
Figure 10E:
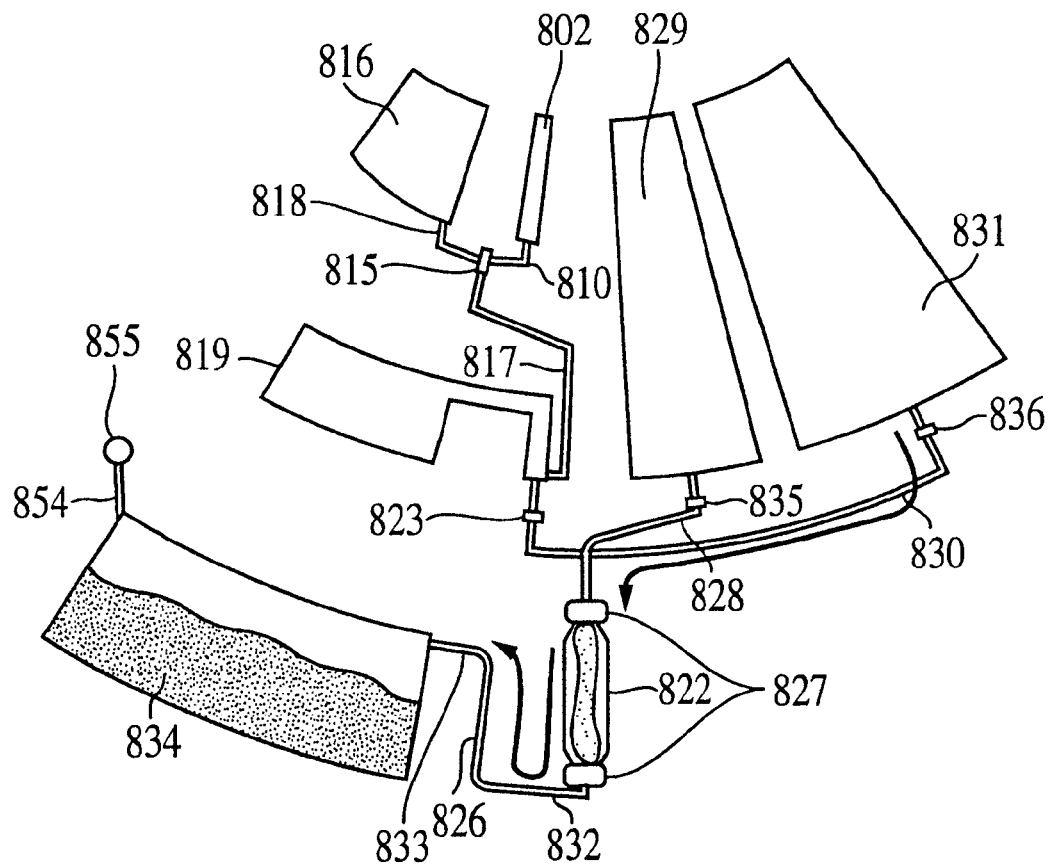

In alternative embodiments, column preparation buffer reservoir 829 and column wash buffer reservoir 831 can be the same reservoir, or can be fluidly connected as shown in FIG. 10A.

Boronate affinity matrix chamber 822 is further fluidly connected to capillary 832. Capillary 832 is from about 0.02 mm to about 2 mm deep and has a cross-sectional diameter of from about 0.02 mm to about 2 mm. Capillary 832 is further fluidly connected with waste reservoir 834. Waste reservoir 834 is from about 0.02 mm to about 3 cm deep and has a cross-sectional diameter of from about 0.02 mm to about 10 cm and is positioned from about 1.2 cm to about 14 cm from the axis of rotation.

As illustrated in FIG. 10A, in the use of this platform a volume of blood from about 15 μL to about 150 μL is applied to metering capillary 802, either directly or using the metering components of the platform described above. Blood flowing through capillary 810 and lysis buffer flowing through capillary 818 are mixed in mixing chamber 815 by overcoming capillary valve 811 or release of sacrificial valve 811. A volume of lysis buffer from about 25 μL to about 90 μL was mixed with the blood sample. Fluid flow within mixing chamber 815 is turbulent, in contrast to fluid flow through capillaries 810 and 818, which is primarily laminar, so that mixing occurs predominantly in mixing chamber 815. Fluid flow proceeds through channel 817 and into secondary metering structure 819.

The mixture of lysis buffer and blood, comprising a lysed blood sample, flows at a rotational speed $f_2$ from about 200 rpm to about 2000 rpm into secondary metering structure 819. The lysed blood sample enters and fills the metering section of secondary metering structure 819. Any additional lysed blood sample then empties into the overflow chamber of secondary metering structure 819. Most preferably, a sufficient volume of lysis buffer and blood sample is applied to the disc to fill at least the metered sections of secondary metering structure 819.

After the lysed blood sample is completely transferred to secondary metering structure 819, capillary or sacrificial valve 835 is released, allowing from 100 μL to about 500 μL of column preparation buffer to flow at rotational speed $f_2$ through capillary 830 and into boronate affinity matrix 822. Continued or discontinuous rotation motivates column preparation buffer through boronate affinity matrix 822, capillary 832, and into waste reservoir 834.

After the column preparation buffer is applied to boronate affinity matrix chamber 822, capillary or sacrificial valve 823 is released, allowing the metered lysed blood sample from the first metered section of secondary metering structure 819 through capillary 821 and into boronate affinity matrix 822 and allowed to incubate in the affinity matrix chamber for from about 0.5 to about 5 min. Capillary or sacrificial valve 836 is then released, allowing from 100 μL to about 500 μL of column wash buffer to flow at rotational speed $f_2$ through capillary 830 and into boronate affinity matrix 822. Continued or discontinuous rotation motivates column preparation buffer through boronate affinity matrix 822, capillary 732 and into waste reservoir 834. During fluid flow of wash buffer through the boronate affinity matrix chamber, the chamber is preferably illuminated by light at a wavelength of 430 nm through the translucent portion of the chamber. The concentration of glycated hemoglobin in the sample is determined thereby.

An alternative embodiment of the glycated hemoglobin assay microsystem platform of the invention is shown in FIG. 11. Construction of the disk embodiments of the platforms of the invention were as described above. The blood application and metering components and their dimensions and relationships to one another are identical to those described above, comprising sample entry port chamber 901, metering capillary 902, overflow capillary 903, and overflow chamber 905. As in Example 1, each of the overflow and fluid chambers is also connected with air ports or air channels, such as 954, and capillary junction(s) 955, that permit venting of air displaced by fluid movement on the platform.

Metered capillary 902 is fluidly connected to capillary 910 that is from about 0.02 mm to about 2 mm deep and has a cross-sectional diameter of from about 0.02 mm to about 2 mm and is connected to sacrificial wax valve 911. Sacrificial wax valve 911 is further fluidly connected with capillary 912 that is from about 0.03 mm to about 2.2 mm. Capillary 912 is further fluidly connected to blood lysis chamber 915 that is from about 0.02 mm to about 3 cm deep, has a cross-sectional diameter of from about 0.02 mm to about 10 cm, is positioned from about 1.2 cm to about 14 cm from the center of rotation, and contains from about 25 μL to about 90 μL of blood 1 lysis solution (0.1% Triton-X100 in 50 mM Tris, pH 9.5). Blood lysis chamber 915 is further fluidly connected with capillary 918 that is from about 0.02 mm to about 2 mm deep and has a cross-sectional diameter of from about 0.02 mm to about 2 mm and is connected to sacrificial wax valve 913. Sacrificial wax valve 913 is further fluidly connected with wax recrystallization chamber 914 that is from about 0.02 mm to about 2 mm deep and has a volumetric capacity sufficient to sequester melted wax from a released wax valve and prevent occlusion of the lumen of the capillary 918 controlled by the valve.

Capillary 918 is further fluidly connected to secondary metering structure 919. Secondary metering structure 919 is from about 0.02 mm to about 3 cm deep, and is positioned from about 1.2 cm to about 14 cm from the center of rotation. Secondary metering structure 919 is constructed to comprise three sections. A first section comprises a throwaway section sample having a volumetric capacity of from about 5 μL to about 10 μL because it is thought that by taking the second section a more representative sample would be obtained. This throwaway section is arranged proximal to the entry position of capillary 918 and is separated from a metering section by a septum that extends from the distal wall of the structure to a position just short of the proximal wall of the structure. This arrangement produces a fluid connection between the throw away section and the metering section. The metering section has a volumetric capacity of from about 5 µL to about 10 µL and is fluidly connected to an overflow section having an excess volumetric capacity of from about 15 µL to about 150 µL. The volumetric capacity of the overflow section is sufficient to accommodate the largest blood fluid volume applied to the disk.

Capillary 921 is in fluid connection with secondary metering structure 919 at the distal wall of the metering section. Capillary 921 is from about 0.02 mm to about 2 mm deep and has a cross-sectional diameter of from about 0.02 mm to about 2 mm and is connected to boronate affinity matrix chamber 922. Boronate affinity matrix chamber 922 is from about 0.02 mm to about 3 cm deep, has a cross-sectional diameter of from about 0.02 mm to about 10 cm and is positioned from about 1.2 cm to about 14 cm from the axis of rotation. Boronate affinity matrix chamber 922 further comprises. 10–50 µL of boronate-functionalized agarose beads having a mean diameter of about 60 cm; the beads are maintained in the chamber 922 using a porous frit 927. Fluid flow through capillary 921 is connected to sacrificial valve 923. Sacrificial wax valve 923 is further fluidly connected with wax recrystallization chamber 924 that is from about 0.03 mm to about 2.2 mm deep and has a volumetric capacity sufficient to sequester melted wax from a released wax valve and prevent occlusion of the lumen of the capillary 923 controlled by the valve.

Boronate affinity matrix chamber 922 is further fluidly connected to capillary 928. Capillary 928 is from about 0.02 mm to about 2 mm deep and has a cross-sectional diameter of from about 0.02 mm to about 2 mm and is connected to column wash buffer reservoir 929. Column wash buffer reservoir 929 is from about 0.02 mm to about 3 cm deep and has a cross-sectional diameter of from about 0.02 mm to about 10 cm and is positioned from about 1.2 cm to about 14 cm from the axis of rotation, more proximal than boronate affinity matrix chamber 922. Column wash buffer reservoir 929 comprises from about 100 µL to about 500 µL of column wash buffer as described above. Fluid flow through capillary 928 is connected to sacrificial valve 936. Sacrificial wax valve 936 is further fluidly connected with wax recrystallization chamber 937 that is from about 0.03 mm to about 2.2 mm deep and has a volumetric capacity sufficient to sequester melted wax from a released wax valve and prevent occlusion of the lumen of the capillary 928 controlled by the valve.

Boronate affinity matrix chamber 922 is further fluidly connected to capillary 932. Capillary 932 is from about 0.02 mm to about 2 mm deep and has a cross-sectional diameter of from about 0.02 mm to about 10 cm and is connected to sample collection cuvette array 934. Sample collection cuvette array 934 is from about 0.02 mm to about 3 cm deep and has a cross-sectional diameter of from about 0.02 mm to about 10 cm and is positioned from about 1.2 cm to about 14 cm from the axis of rotation. Sample collection cuvette array 934 is separated into a multiplicity of individual chambers, each separated from one another by septa that extend from the distal wall of the cuvettes to a position adjacent to the proximal wall of the cuvettes, so that a fluid passage 950 is maintained between each of the cuvettes. The fluid passage 950 is formed by the back (proximal wall) of the sample collection cuvette array 934 and the row of septa separating each of the sections of the sample collection cuvettes 934. Capillary 932 is fluidly connected to sample collection cuvette array 934 at a position adjacent to the proximal wall of the array and directed to the cuvette most proximal to the boronate affinity matrix chamber 922.

Alternatively, the septa can be eliminated in sample collection cuvette array 934, wherein the sample cuvette is a single chamber.

Capillary 941 is fluidly connected to secondary metering structure 919. Capillary 941 is from about 0.02 mm to about 2 mm deep and has a cross-sectional diameter of from about 0.02 mm to about 2 mm and is connected to secondary metering structure 919 at a position between the metering section and the overflow section. Capillary 941 is further fluidly connected with total hemoglobin read chamber 942. Total hemoglobin read chamber 942 is from about 0.02 mm to about 3 cm deep, is positioned from about 1.2 cm to about 14 cm from the center of rotation, and has a volumetric capacity of from about 50 µL to about 250 µL. Total hemoglobin read chamber 942 is positioned radially more distal from the center of rotation than secondary metering structure 919, and comprises a read window translucent to light having a wavelength of from about 430 nm. In addition, there is no capillary or sacrificial valving controlling fluid flow in capillary 941.

The platform also comprises control sample read cuvettes 943 and 944, advantageously positioned in proximity to total hemoglobin read chamber 942. Control sample read cuvettes 943 and 944 are each from about 0.02 mm to about 3 cm deep, positioned from about 1.2 cm to about 14 cm from the center of rotation, and have a volumetric capacity of from about 50 µL to about 200 µL. Control sample read cuvettes 943 and 944 comprise a read window translucent to light having a wavelength of from about 430 nm. Control sample read cuvettes 943 and 944 are not fluidly connected to any other structure on the platform and contain standards and/or calibration reagents.

As illustrated in FIG. 11, in the use of this platform a volume of blood from about 15 µL to about 150 µL is applied to metering capillary 902, either directly or using the metering components of the platform described above (FIG. 11A). Release of sacrificial valve 911 and rotation of the platform at a rotational speed $f_1$ of from about 50 rpm to about 1000 rpm motivates blood flow through capillary 910 and into blood lysis chamber 915 (FIG. 11C). The mixture of blood and blood lysis buffer in blood lysis chamber 915 is mixed by agitation, wherein the platform is accelerated repeatedly from about +2000 rpm/sec to −2000 rpm/sec (wherein "+" and "−" indicate rotation in different directions) over a time period of about 30 sec to about 600 sec (FIG. 11D and 11E). Release of sacrificial valve 913 and rotation of the platform at a rotational speed $f_2$ of from about 200 rpm to about 2000 rpm motivates the lysed blood sample to flow through capillary 918 and into secondary metering structure 919 (FIG. 11F). Continued rotation motivates lysed blood solution to fill the metering section of secondary metering structure 919; after filling of this section of the structure, excess lysed blood sample flows through capillary 941 and into total hemoglobin read chamber 942. After filling of total hemoglobin read chamber 942, any excess lysed blood sample is displaced into the overflow section of secondary metering structure 919.

Figure 11A:
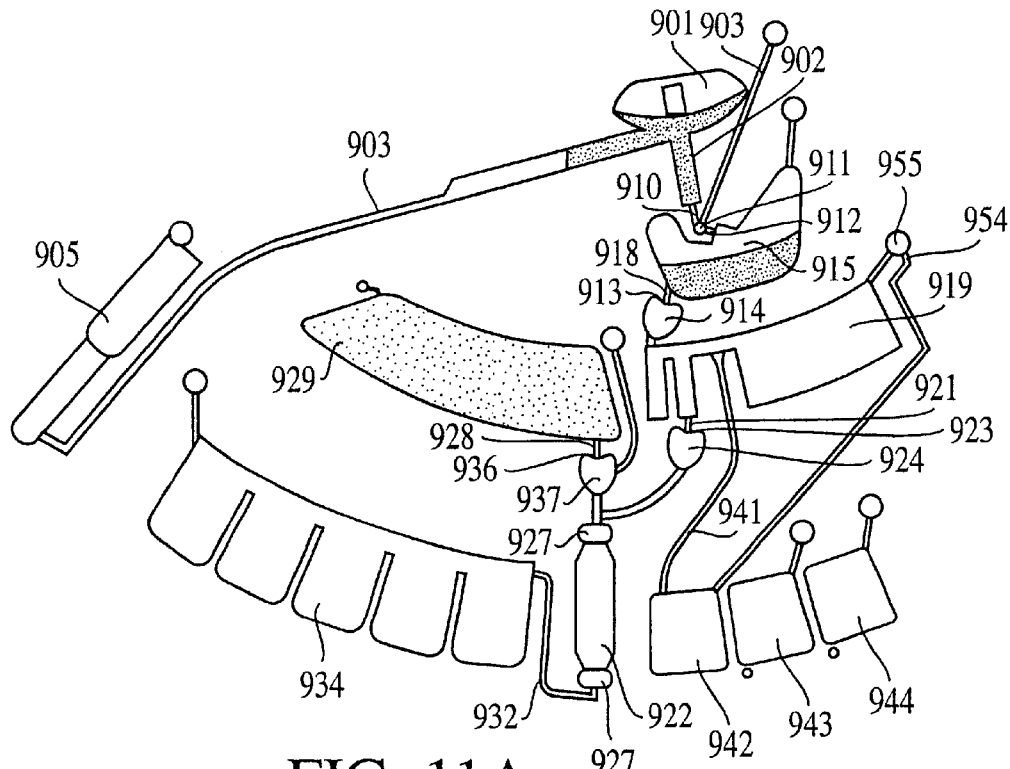
Figure 11B:
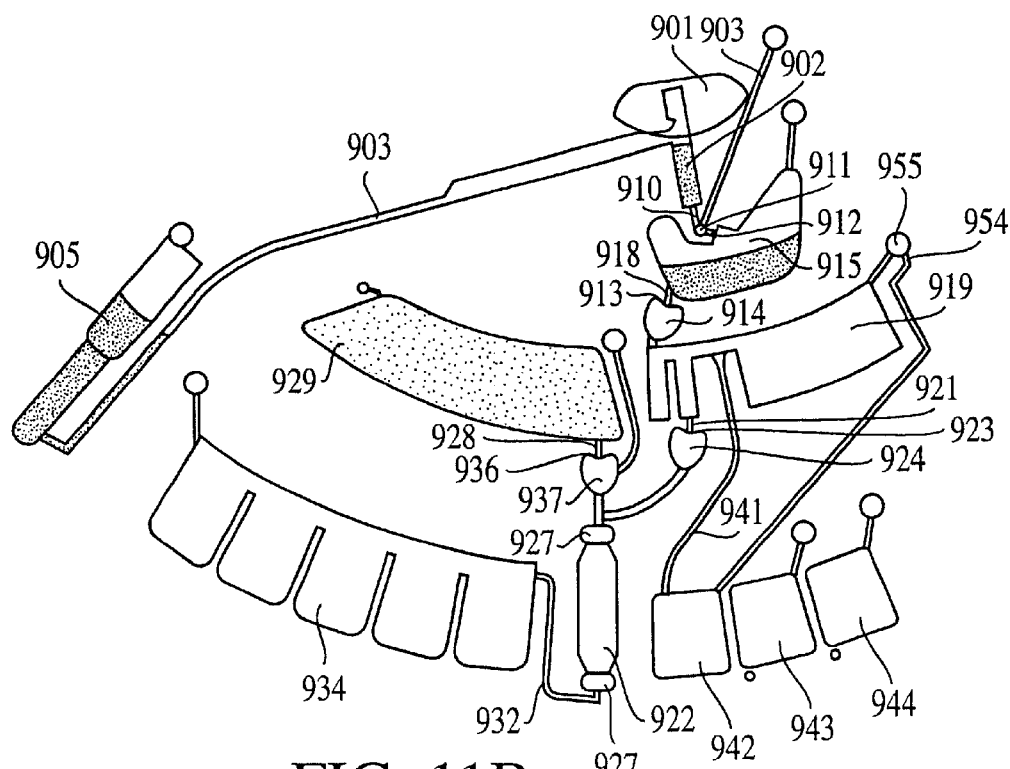
Figure 11C:
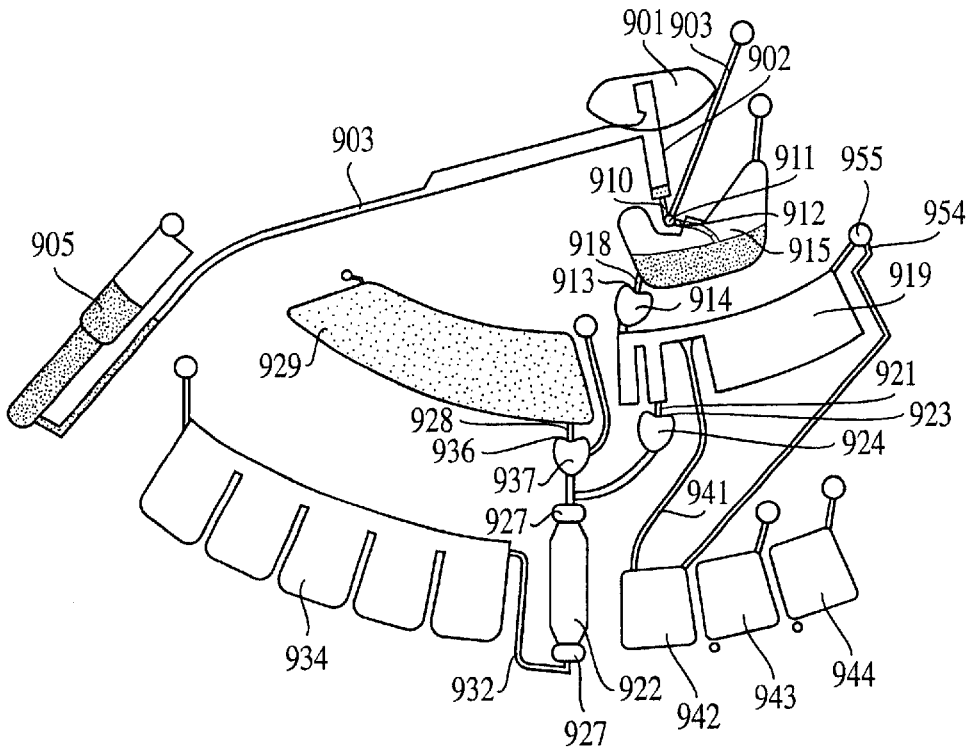
Figure 11D:
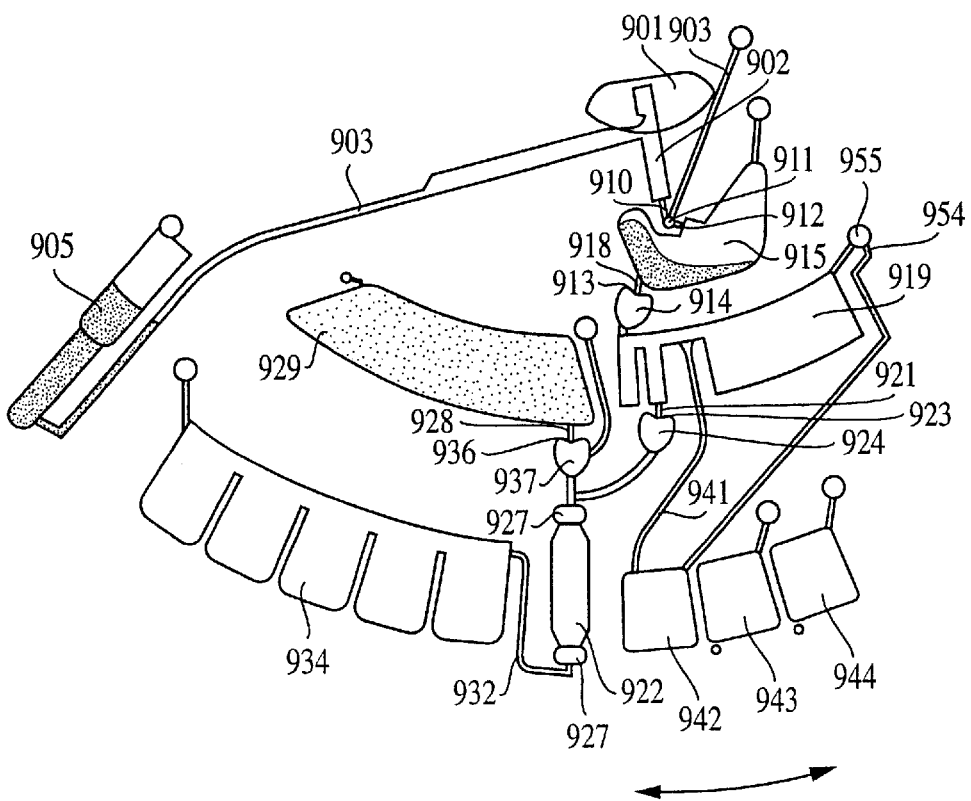
Figure 11E:
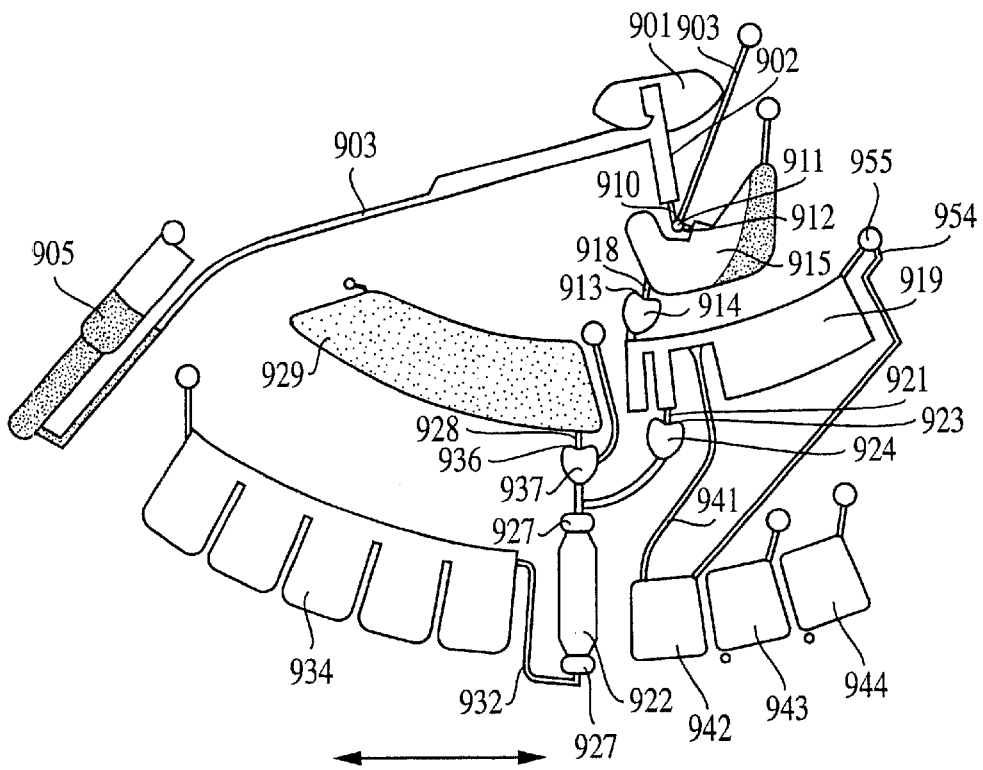
Figure 11F:
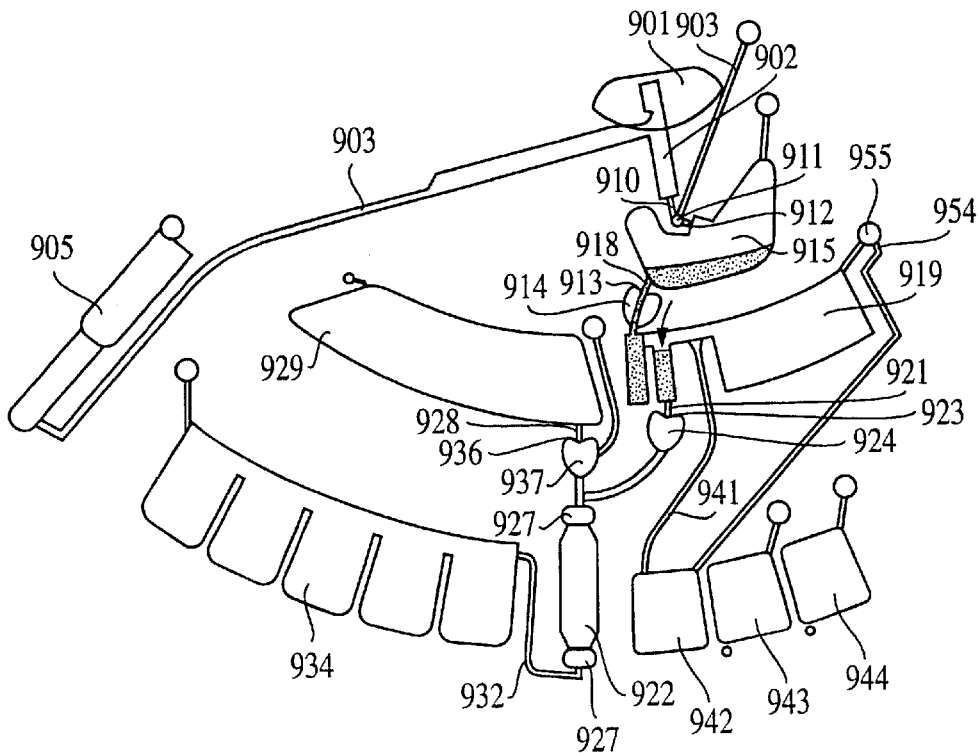
Figure 11G:
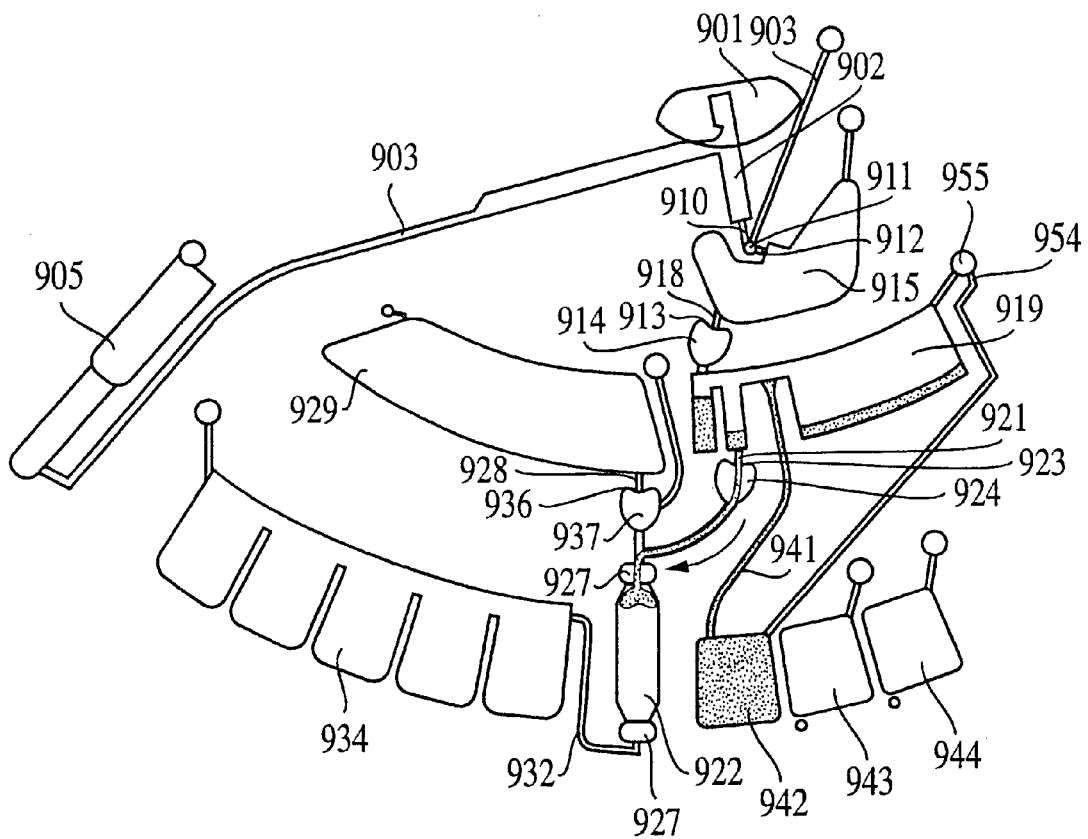
Figure 11H:
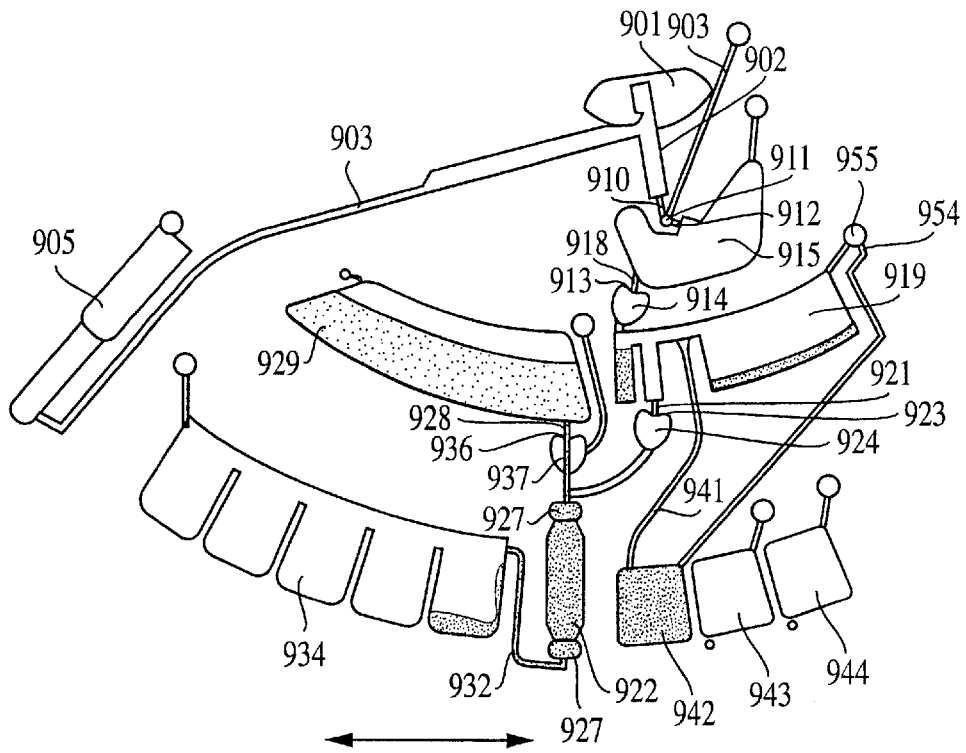
Figure 11J:
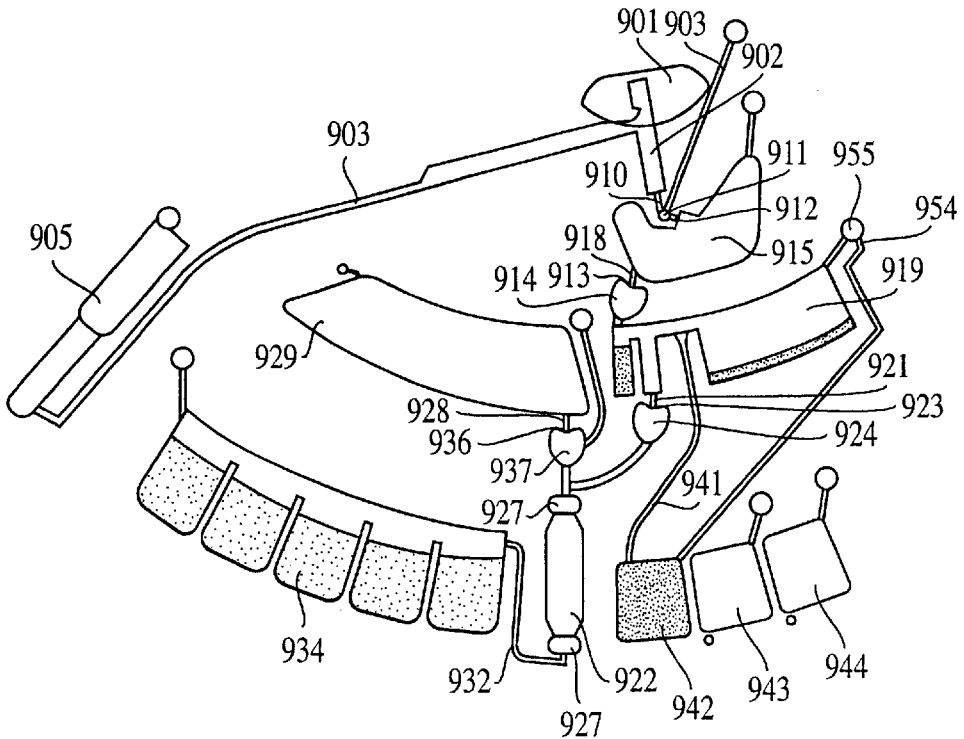

Release of sacrificial valve 923 and rotation of the platform at a rotational speed $f_3$ of from about 200 rpm to about 2000 rpm motivates the metered lysed blood sample in the metering section of secondary metering structure 922 to flow through capillary 921 and into boronate affinity matrix chamber 922 (FIG. 11G). After incubation of the metered lysed blood sample 956 in boronate affinity matrix chamber 922, sacrificial valve 936 is released and the platform is rotated at a rotational speed $f_4$ of from about 200 rpm to about 3000 rpm. Column wash buffer flows from column wash buffer reservoir 929 through capillary 921 and into boronate affinity matrix chamber 922, displacing the unbound hemoglobin fraction through capillary 932 and into sample collection cuvette array 934 (FIG. 11H). Continued rotation of the platform displaces the collected sample sequentially into the separate cuvettes radially away from the position of boronate affinity matrix chamber 922 on the platform (FIG. 11J). Sample collection cuvette array 934 is then interrogated by illumination with light at a wavelength of 430 nm, and the concentration of non-glycated hemoglobin in the blood sample determined. Additionally, illumination of total hemoglobin read chamber 942 with light at a wavelength at 415 nm is performed to determine the concentration of total hemoglobin in the blood sample. The amount of glycated hemoglobin is calculated by subtracting the amount of non-glycated hemoglobin in the sample from the total hemoglobin concentration in the sample. Control sample read cuvettes 943 and 944 are used to calibrate the spectrophotometric readings.

In alternative embodiments of these microfluidics systems, the boronate affinity matrix is replaced by other substances capable of differentially binding glycated or non-glycated hemoglobin species. In a first embodiment of such an alternative, m-aminophenylboronate polyacrylic acid is used to derivatize, a positively-charged nylon 66 membrane (such as Biodyne-B, Pall Biosupport Division, Port Washington, N.Y.). This membrane is used in substitution for the boronate-functionalized agarose beads in the boronate affinity matrix chambers of the invention. In preferred embodiments, the boronate affinity matrix chambers are modified to contain the membrane in contact with or more preferably adhered to the platform surface within the chamber, so that one face of the membrane derivatized with m-aminophenylboronate polyacrylic acid is in contact with the lysed blood sample. Binding of glycated hemoglobin to the membrane is quantitated by visible light reflectance spectroscopy at a wavelength of 415 nm.

A second alternative embodiment of the glycated hemogoblin microsystems assays of the invention comprises inositol hexaphosphate. In these embodiments, inositol an hexaphosphate is attached (covalently or by electrostatic interactions) to a solid support, including but not limited to beads, membranes, pads, etc. The lysed blood sample is treated with sodium dithionite to convert it to the deoxy form. In the microsystems platforms of the invention, an effective amount of sodium dithionite is provided with the lysis buffer, or as a component of the secondary metering structures, most preferably as a dry powder coating on the walls of one or both of the metering sections thereof. The deoxygenated lysed blood sample is then placed in contact with the solid support comprising inositol hexaphosphate, preferably comprising and in substitution for the boronate affinity matrix chamber of the glycated hemoglobin platforms of the invention. In these embodiments, the portion of hemoglobin that does not bind to the inositol phosphate-containing solid support is the glycated fraction, which can be delivered to a read chamber, cuvette or other optically-appropriate component of the platform and the amount of glycated hemoglobin determine directly by visible light reflectance spectrophotometry at a wavelength of 415 nm.

The invention also provides microsystem platforms for performing a multiplicity of reactions including identification of chemical species from solutions or complex mixtures and separations of particular components of a solution or complex mixture. This aspect of the invention is illustrated by a microfluidics array for determining glucose concentration and separating glycated hemoglobin from a blood sample, as shown in FIGS. 12A through 12Q and 13A through 13D.

Figure 13A:
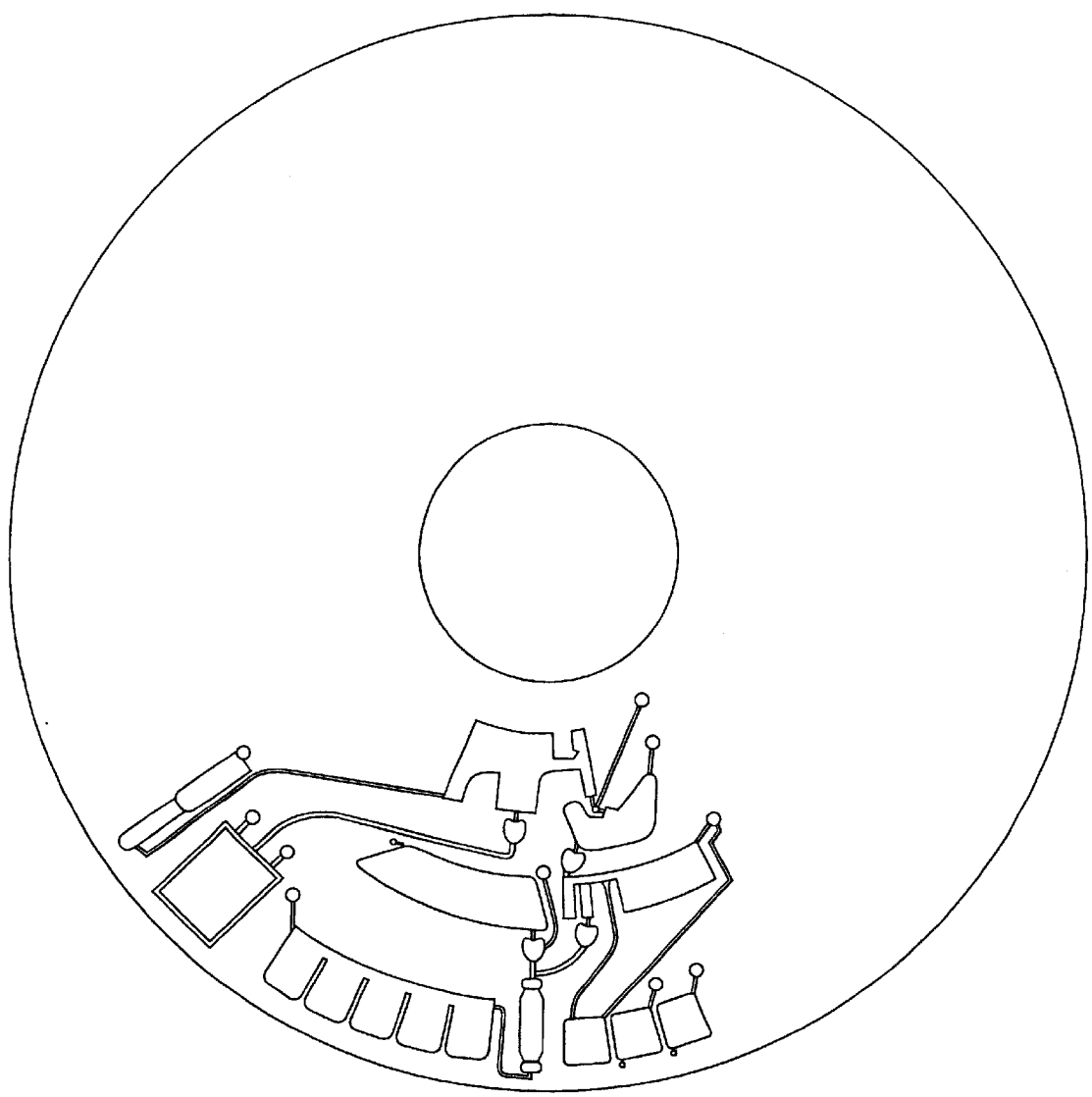
Figure 13B:
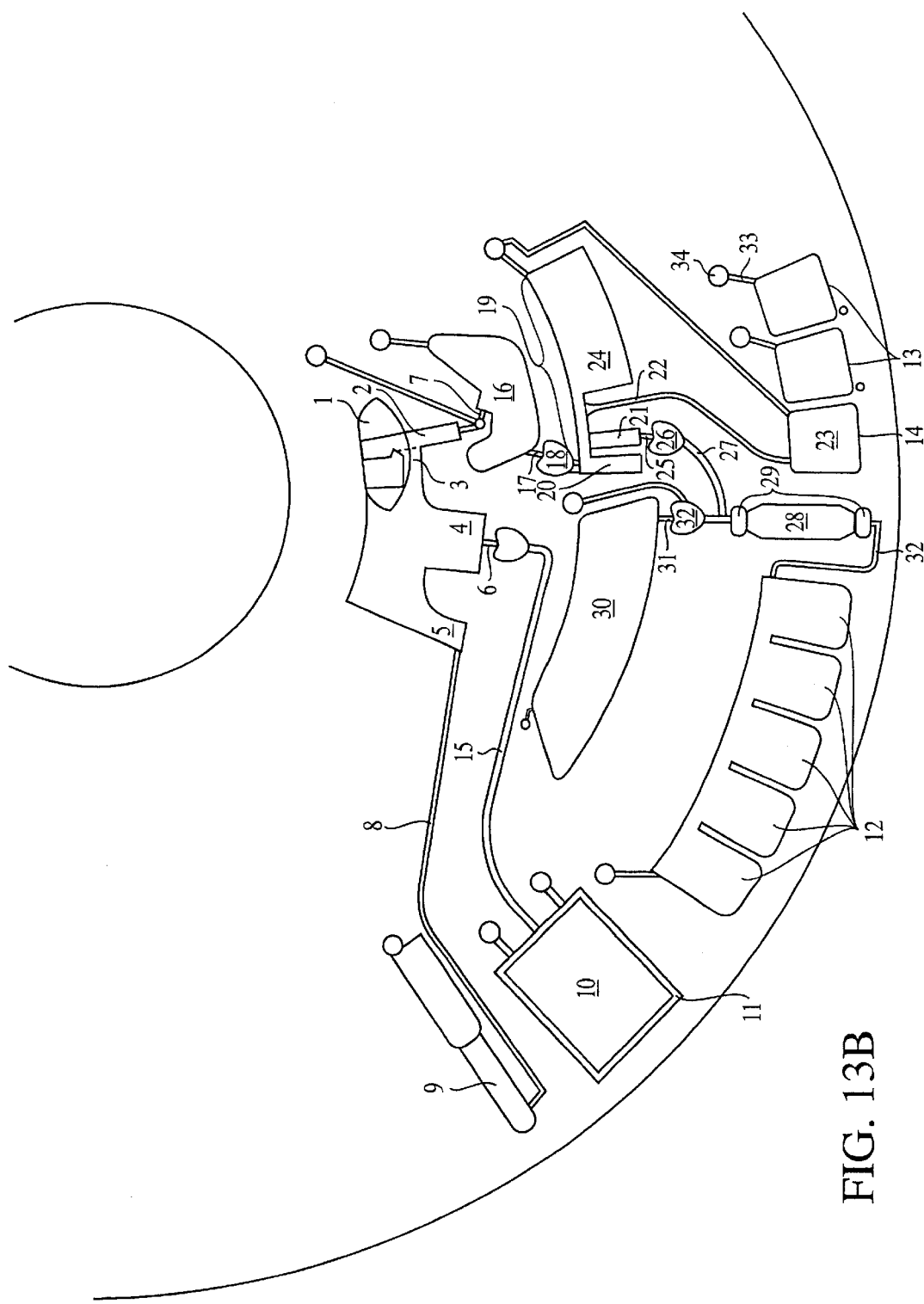
Figure 13C:
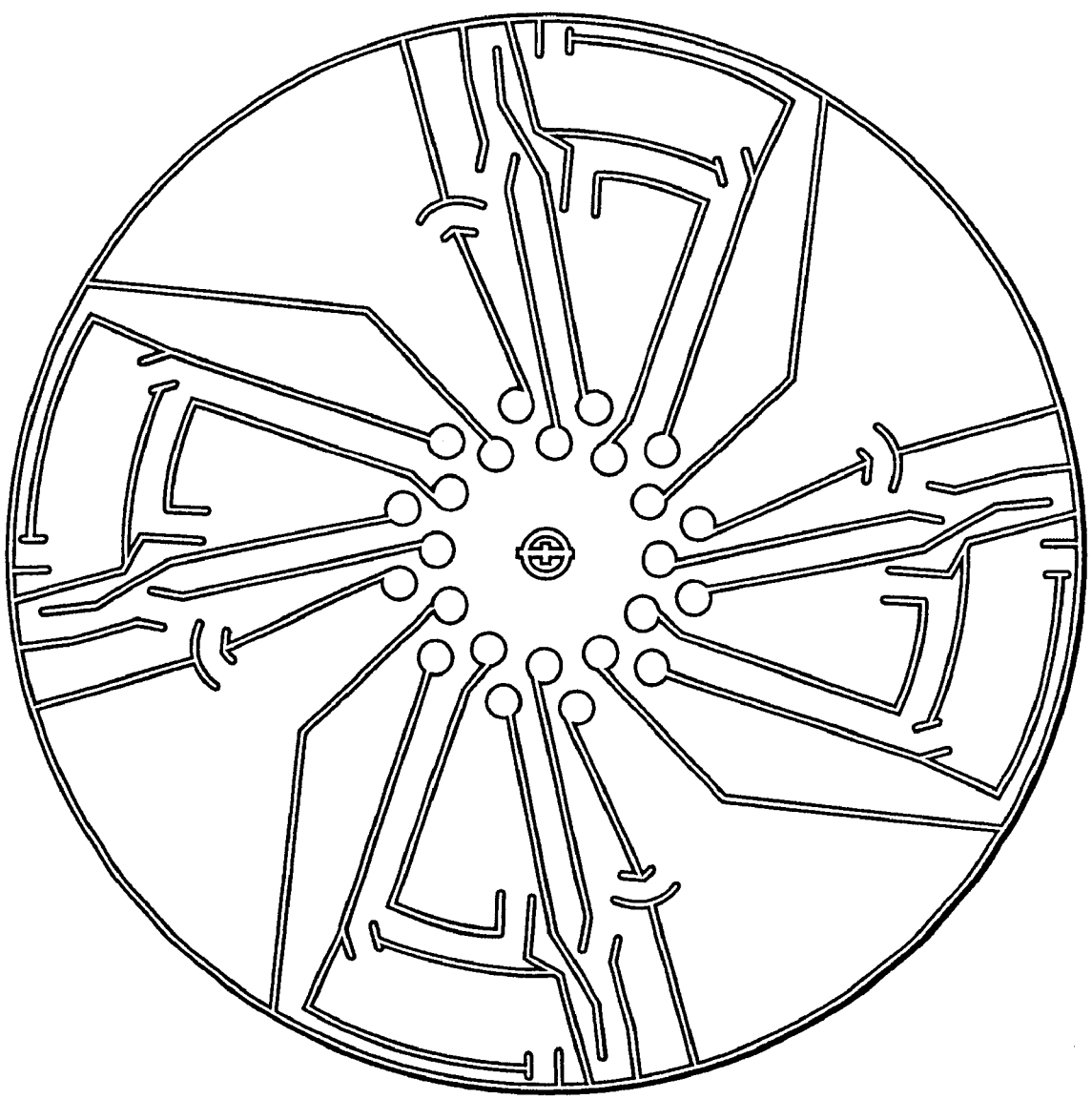
Figure 13D:
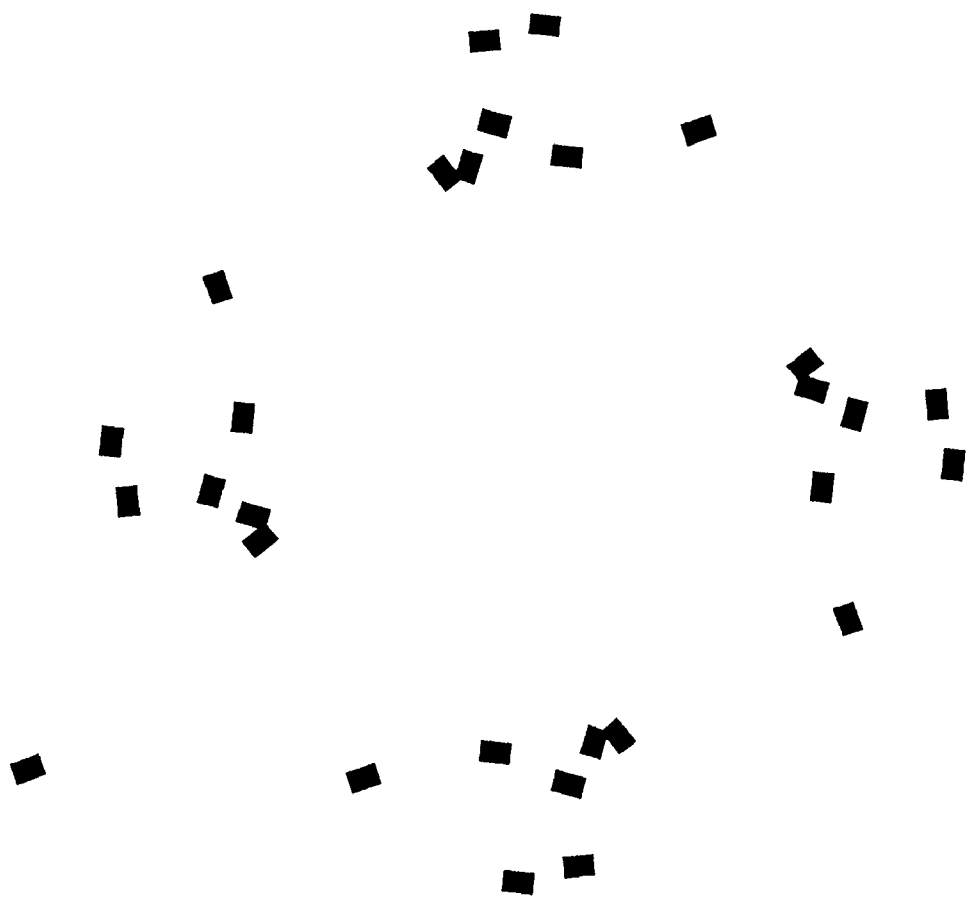
Figure 13E:
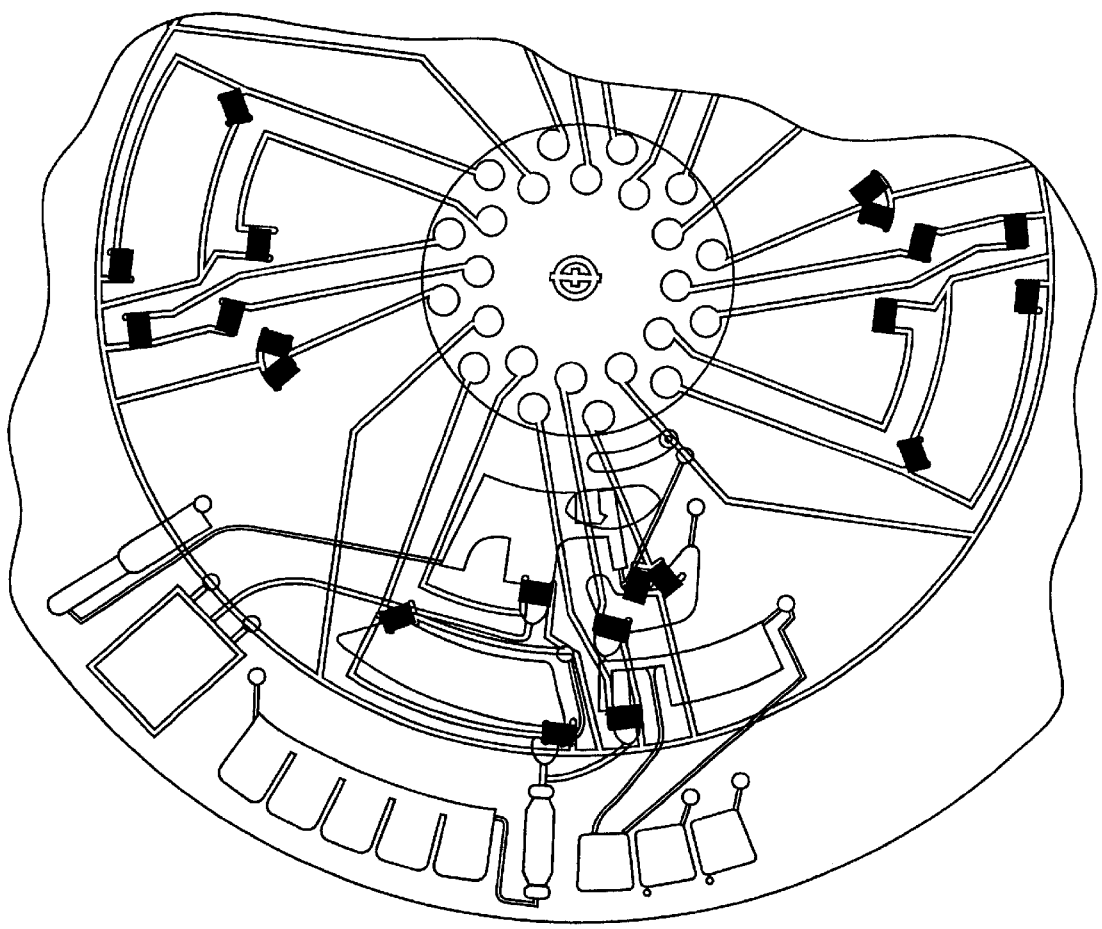

Construction of the disk embodiments of the platforms of the invention were as described above. FIG. 13B shows a detailed description of the microfluidics components of the platform, which are described in additional detail below. FIG. 13C shows the geometry of a screen printed electrical lead layer deposited on a mylar substrate. FIG. 13D shows the positions of screen printed heaters activated by the electrical leads of the lead layer and screen printed on mylar. FIG. 13E shows a overlay of these components in the assembled disc.

Referring to the microfluidics components of the platform shown in FIG. 13B, an entry port 1 is positioned on the top surface of the disc and is open for the user to apply an unmetered sample. Entry port 1 is from about 0.02 mm to about 3 cm deep, has a cross-sectional diameter of from about 0.02 mm to about 10 cm, is positioned from about 1.2 cm to about 14 cm from the center of rotation, and is fluidly connected to capillary channel 1A that is from about 0.02 mm to about 2 mm deep and has a cross-sectional diameter of from about 0.02 mm to about 2 mm. Capillary channel 1A is fluidly connected to metering component 2, which comprises four sections. The first section is rectangularly-shaped and extends in a direction proximal to the axis of rotation away from its fluid connection with capillary channel 1A. About half way up this rectangular section is a lateral chamber 3, which empties into a blood glucose metering chamber 4 and an overflow chamber 5. The first section of the metering component is from about 0.02 mm to about 3 cm deep, has a cross-sectional diameter of from about 0.02 mm to about 10 cm, is positioned from about 1.2 cm to about 14 cm from the center of rotation, and has a volumetric capacity of from about 15 $\mu$L to about 150 $\mu$L. The lateral chamber 3 is from about 0.02 mm to about 3 cm deep, has a cross-sectional diameter of from about 0.02 mm to about 10 cm, and is positioned from about 1.2 cm to about 14 cm from the center of rotation. Blood glucose metering chamber 4 is from about 0.02 mm to about 3 cm deep, has a cross-sectional diameter of from about 0.02 mm to about 10 cm, is positioned from about 1.2 cm to about 14 cm from the center of rotation and has a volumetric capacity of from about 1 $\mu$L to about 15 $\mu$L. Overflow chamber 5 is from about 0.02 mm to about 3 cm deep, has a cross-sectional diameter of from about 0.02 mm to about 10 cm, is positioned from about 1.2 cm to about 14 cm from the center of rotation and has a volumetric capacity of from about 5 $\mu$L to about 50 $\mu$L.

Overflow chamber 5 is fluidly connected to overflow channel 8 that is from about 0.02 mm to about 3 cm deep, has a cross-sectional diameter of from about 0.02 mm to about 10 cm and extends from about 10 mm to about 5 cm from overflow chamber 5. Overflow channel 5 is fluidly connected to short sample detection cuvette 9 that is from about 0.02 mm to about 3 cm deep, has a cross-sectional diameter of from about 0.02 mm to about 10 cm, is positioned from about 1.2 cm to about 10 cm from the center of rotation and has a volumetric capacity of from about 15 $\mu$L to about 150 $\mu$L Blood glucose metering chamber 4 is fluidly connected to capillary 15 that is from about 0.02 mm to about 3 cm deep, has a cross-sectional diameter of from about 0.02 mm to about 10 cm and extends from about 1 mm to about 5 cm from blood glucose metering chamber 4. Capillary 15 is connected to sacrificial wax valve 6, which is further fluidly connected with wax recrystallization chamber 6A that is from about 0.03 mm to about 2.2 mm deep and has a volumetric capacity sufficient to sequester melted wax from a released wax valve and prevent occlusion of the lumen of the capillary 15 controlled by the valve. Capillary 15 is further fluidly connected with glucose assay chamber 11 that is from about 0.02 mm to about 3 cm deep, has a cross-sectional diameter of from about 0.02 mm to about 10 cm, is positioned from about 1.2 cm to about 14 cm from the center of rotation and has a volumetric capacity of from about 5 µL to about 50 µL. Glucose assay chamber 11 comprises a depression 11A in the surface of the platform having a depth of from about 0.02 mm to about 3 cm, most preferably comprising a circular or concave depression connected to capillary 15 so that blood flows into the chamber through the bottom of depression 11A. Depression 11A is constructed to have a volumetric capacity of from half to twice the assay volume. Blood glucose assay chamber 11 also comprises a pad or matrix 10 of a hydrophilic substance possessing a pore size of 0.2–2.0 µm, most preferably comprising a positively-charged nylon matrix having a pore size of about 0.8 µm. The upper limit on pore size of matrix 10 is chosen to inhibit or prevent blood cell entry into the matrix. The matrix is positioned in blood glucose assay chamber 11 to be in fluidic contact with depression 11A, more preferably covering depression 11A, and most preferably having a surface area greater than the surface area of depression 11A. The matrix was further impregnated with immobilized reagents 11B which produce a detectable product proportional to the amount or concentration of glucose in a blood sample. Most preferably, the detectable product is a colored product 11C, i.e., a product absorbing light at a detectable, most preferably a visible, wavelength.

Lysis metering chamber 2 is fluidly connected to capillary 7 controlled by sacrificial valve 7A. Sacrificial wax valve 7A is further fluidly connected with wax recrystallization chamber 7B that is from about 0.03 mm to about 2.2 mm deep and has a volumetric capacity sufficient to sequester melted wax from a released wax valve and prevent occlusion of the lumen of the capillary 7 controlled by the valve. Capillary 7 is from about 0.02 mm to about 2 mm deep, has a cross-sectional diameter of from about 0.02 mm to about 2 mm, extends from about 1 mm to about 5 cm from lysis metering chamber 2 and is fluidly connected to blood lysis chamber 16. Blood lysis chamber 16 is from about 0.02 mm to about 3 cm deep, has a cross-sectional diameter of from about 0.02 mm to about 10 cm, is positioned from about 1.2 cm to about 14 cm from the center of rotation, and contains from about 25 µL to about 90 µL of blood lysis solution (0.1% Triton-X100 in 50 mM Tris, pH 9.5).

Blood lysis chamber 16 is fluidly connected at a distal aspect to capillary 17 controlled by sacrificial valve 18. Capillary 17 is from about 0.02 mm to about 2 mm deep and has a cross-sectional diameter of from about 0.02 mm to about 2 mm Sacrificial wax valve 18 is further fluidly connected with wax recrystallization chamber 18A that is from about 0.03 mm to about 2.2 mm deep and has a volumetric capacity sufficient to sequester melted wax from a released wax valve and prevent occlusion of the lumen of the capillary 17 controlled by the valve. Capillary 17 is fluidly connected to secondary metering structure 19. Secondary metering structure 19 is from about 0.02 mm to about 3 cm deep, and is positioned from about 1.2 cm to about 14 cm from the center of rotation. Secondary metering structure 19 is constructed to comprise three sections. A first section 20 comprises a throwaway section having a volumetric capacity of from about 5 µL to about 10 µL because it is thought that a more representative sample would be obtained thereby. Throwaway section 20 is arranged proximal to the entry position of capillary 17 and is separated from a metering section 21 by a septum that extends from the distal wall of the structure to a position just short of the proximal wall of the structure. This arrangement produces a fluid connection between throwaway section 20 and the metering section 21. Metering section has a volumetric capacity of from about 5 µL to about 10 µL and is fluidly connected to an overflow section 24 having an excess volumetric capacity of from about 15 µL to about 150 µL. The volumetric capacity of the overflow section is sufficient to accommodate the largest blood fluid volume applied to the disk.

Capillary 25 is in fluid connection with secondary metering structure 21 at the distal wall of the metering section. Capillary 25 is from about 0.02 mm to about 2 mm deep and has a cross-sectional diameter of from about 0.02 mm to about 2 mm and is connected to boronate affinity matrix chamber 28. Capillary 25 is fluidly connected to sacrificial wax valve 26 that is further fluidly connected with wax recrystallization chamber 26A Wax recrystallization chamber 26A is from about 0.03 mm to about 2.2 mm deep and has a volumetric capacity sufficient to sequester melted wax from a released wax valve and prevent occlusion of the lumen of the capillary 25 controlled by the valve.

Boronate affinity matrix chamber 28 is from about 0.02 mm to about 3 cm deep, has a cross-sectional diameter of from about 0.02 mm to about 10 cm and is positioned from about 1.2 cm to about 14 cm from the axis of rotation. Boronate affinity matrix chamber 28 further comprises boronate-functionalized agarose beads having a mean diameter of about 60 µm; the beads are maintained in the chamber 28 using a porous frit 29. Boronate affinity matrix chamber 28 is further fluidly connected to capillary 31. Capillary 31 is from about 0.02 mm to about 2 mm deep and has a cross-sectional diameter of from about 0.02 mm.to about 2 mm and is connected to column wash buffer reservoir 30. Column wash buffer reservoir 30 is from about 0.02 mm to about 3 cm deep and has a cross-sectional diameter of from about 0.02 mm to about 10 cm and is positioned from about 1.2 cm to about 14 cm from the axis of rotation, more proximal than boronate affinity matrix chamber 28. Column wash buffer reservoir 30 comprises from about 250 µL to about 350 µL of column wash buffer as described above. Fluid flow through capillary 31 is connected to sacrificial valve 32. Sacrificial wax valve 32 is further fluidly connected with wax recrystallization chamber 32A that is from about 0.03 mm to about 2.2 mm deep and has a volumetric capacity sufficient to sequester melted wax from a released wax valve and prevent occlusion of the lumen of the capillary 32 controlled by the valve.

Boronate affinity matrix chamber 28 is further fluidly connected to capillary 37. Capillary 37 is from about 0.02 mm to about 2 mm deep and has a cross-sectional diameter of from about 0.02 mm to about 2 mm and is connected to sample collection cuvette array 12. Sample collection cuvette array 12 is from about 0.02 mm to about 3 cm deep and has a cross-sectional diameter of from about 0.02 mm to about 10 cm and is positioned from about 1.2 cm to about 14 cm from the axis of rotation. Sample collection cuvette array 12 is separated into a multiplicity of individual chambers, each separated from one another by septa that extend from the distal wall of the cuvettes to a position adjacent to the proximal wall of the cuvettes, so that a fluid passage 50 is maintained between each of the cuvettes. The fluid passage 50 is formed by the back (proximal wall) of the sample collection cuvette array 12 and the row of septa separating each of the sections of the sample collection cuvettes 12. Capillary 37 is fluidly connected to sample collection cuvette array 12 at a position adjacent to the proximal wall of the array and directed to the cuvette most proximal to the boronate affinity matrix chamber 28. In alternative embodiments, collection cuvette array 12 can be constructed without such septa, and this structure is then just a single collection chamber.

Capillary 22 is fluidly connected to secondary metering structure 19. Capillary 22 is from about 0.02 mm to about 2 mm deep and has a cross-sectional diameter of from about 0.02 mm to about 2 mm and is connected to secondary metering structure 19 at a position between the metering section and the overflow section. Capillary 22 is further fluidly connected with total hemoglobin read chamber 23. Total hemoglobin read chamber 23 is from about 0.02 mm to about 3 cm deep, is positioned from about 1.2 cm to about 14 cm from the center of rotation, and has a volumetric capacity of from about 5 $\mu$L to about 100 $\mu$L. Total hemoglobin read chamber 23 is positioned radially more distal from the center of rotation than secondary metering structure 19, and comprises a read window translucent to light having a wavelength of from about 400 nm to about 950 nm. In addition, there is no capillary or sacrificial valving controlling fluid flow in capillary 23.

The platform also comprises control sample read cuvettes 13 and 14, advantageously positioned in proximity to total hemoglobin read chamber 23. Control sample read cuvettes 13 and 14 are each from about 0.02 mm to about 3 cm deep, positioned from about 1.2 cm to about 14 cm from the center of rotation, and have a volumetric capacity of from about 5 $\mu$L to about 100 $\mu$L. Control sample read cuvettes 13 and 14 comprise a read window translucent to light having a wavelength of from about 400 nm to about 950 nm. Control sample read cuvettes 13 and 14 are not fluidly connected to any other structure on the platform.

Air displacement channels 33 and capillary junction(s) 34, that permit venting of air displaced by fluid movement on the platform, are fluidly connected to the components of the platform to permit unimpeded fluid flow.

Figure 12A:
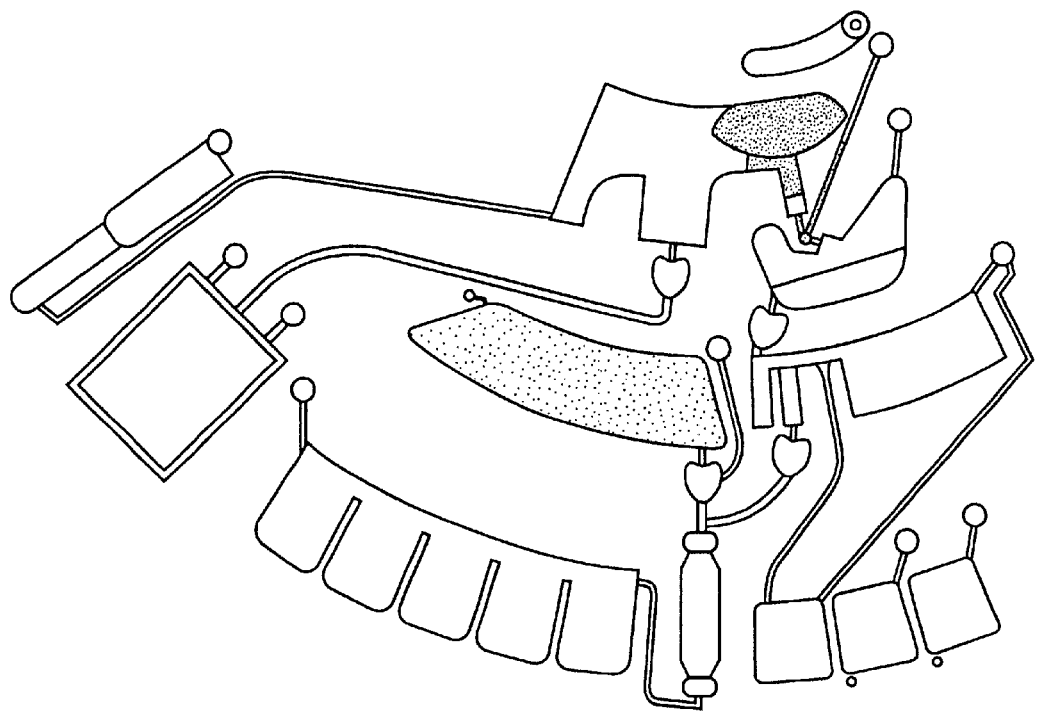
FIGS. 12 and 13 are schematic representations of microfluidics arrays and components for performing both direct analyte detection assays and analyte separations using the microsystems platforms of the invention.
Figure 12B:
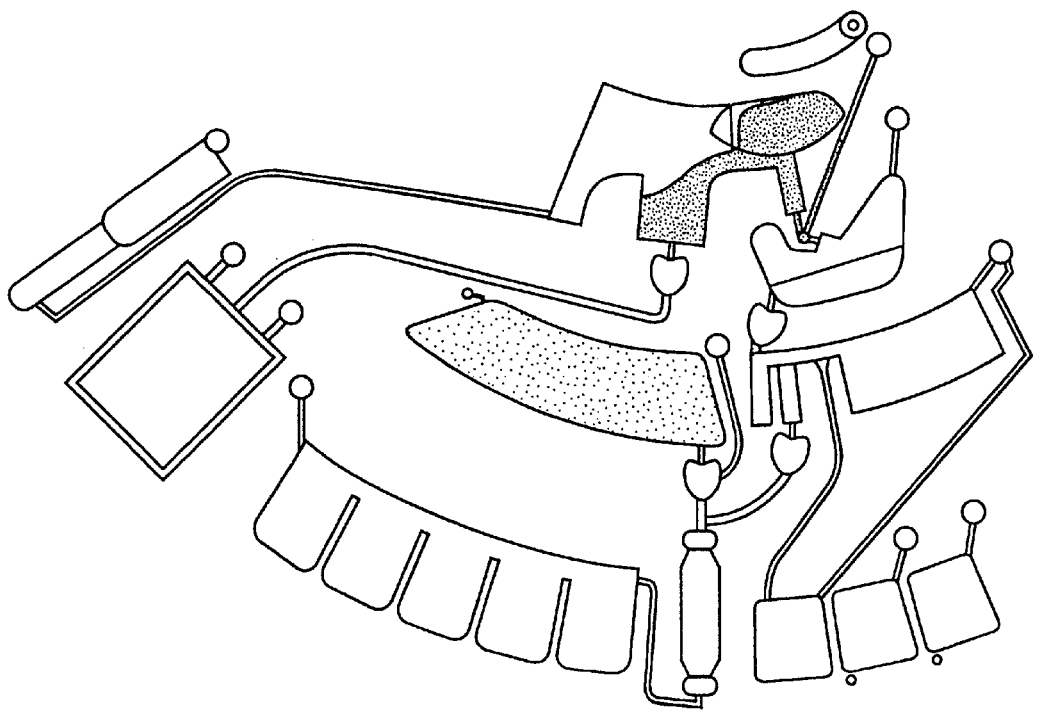
Figure 12C:
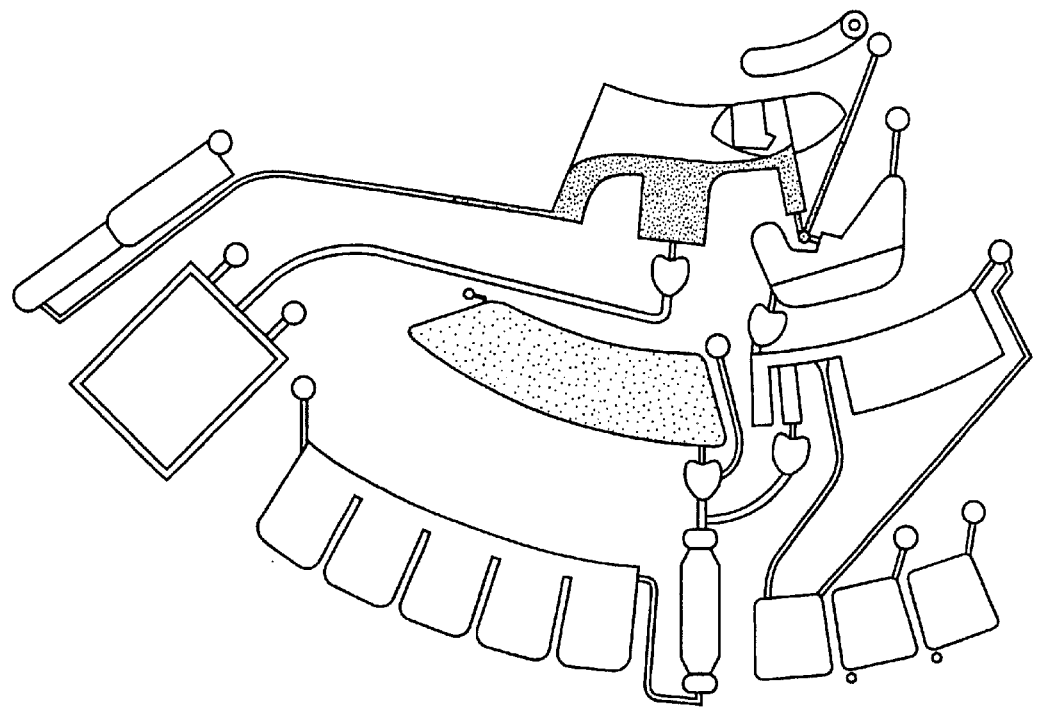
Figure 12D:
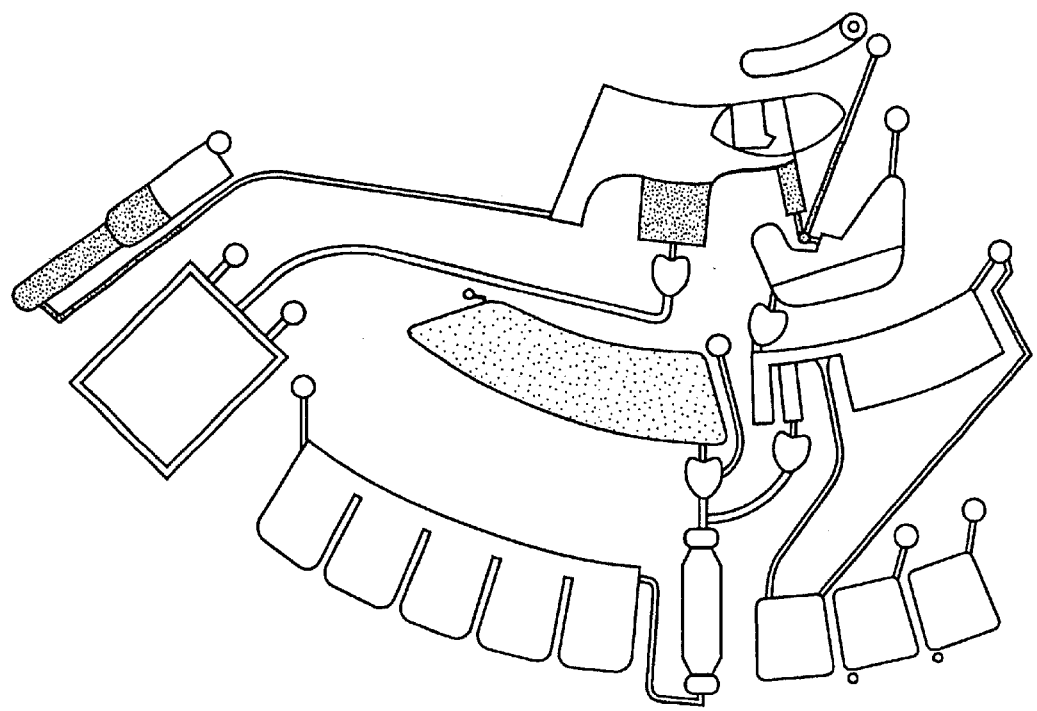
Figure 12E:
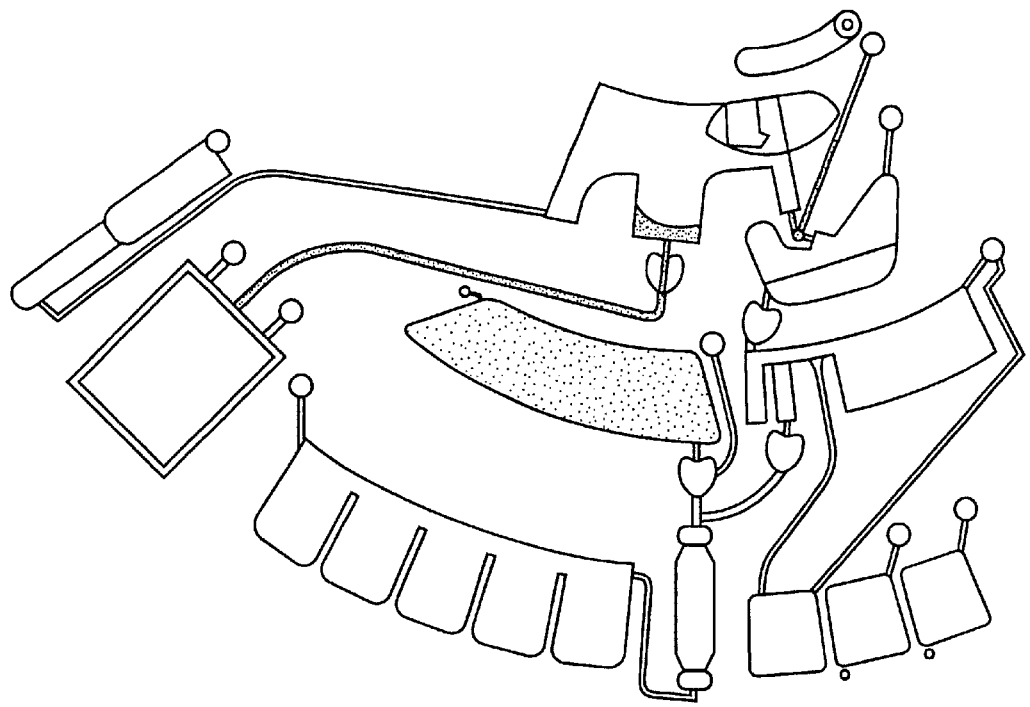
Figure 12F:
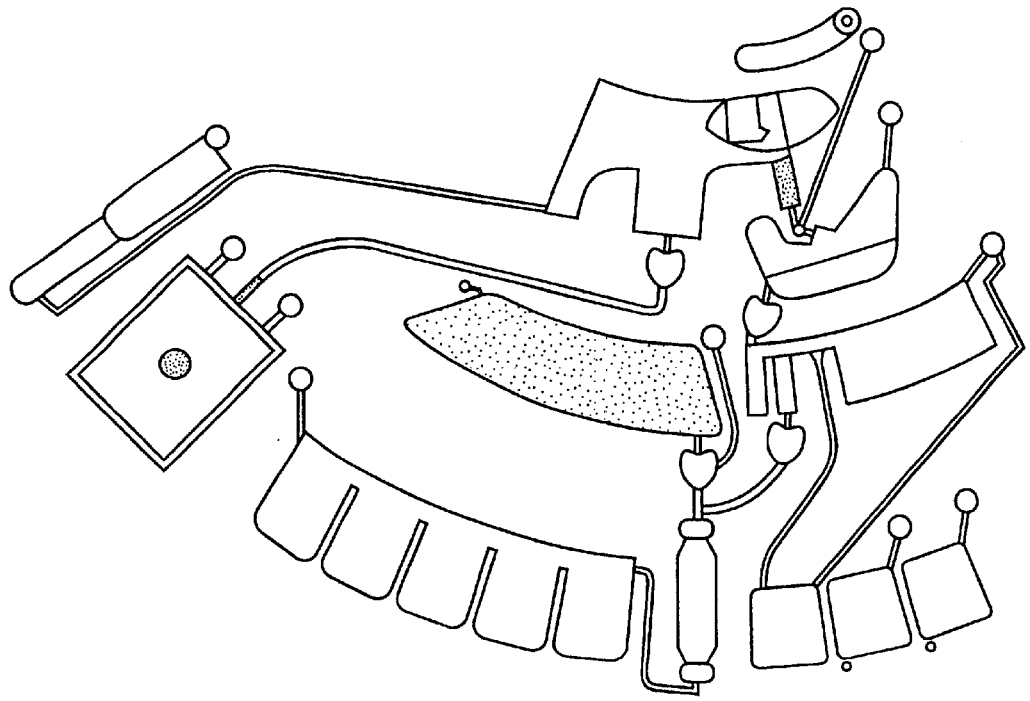
Figure 12G:
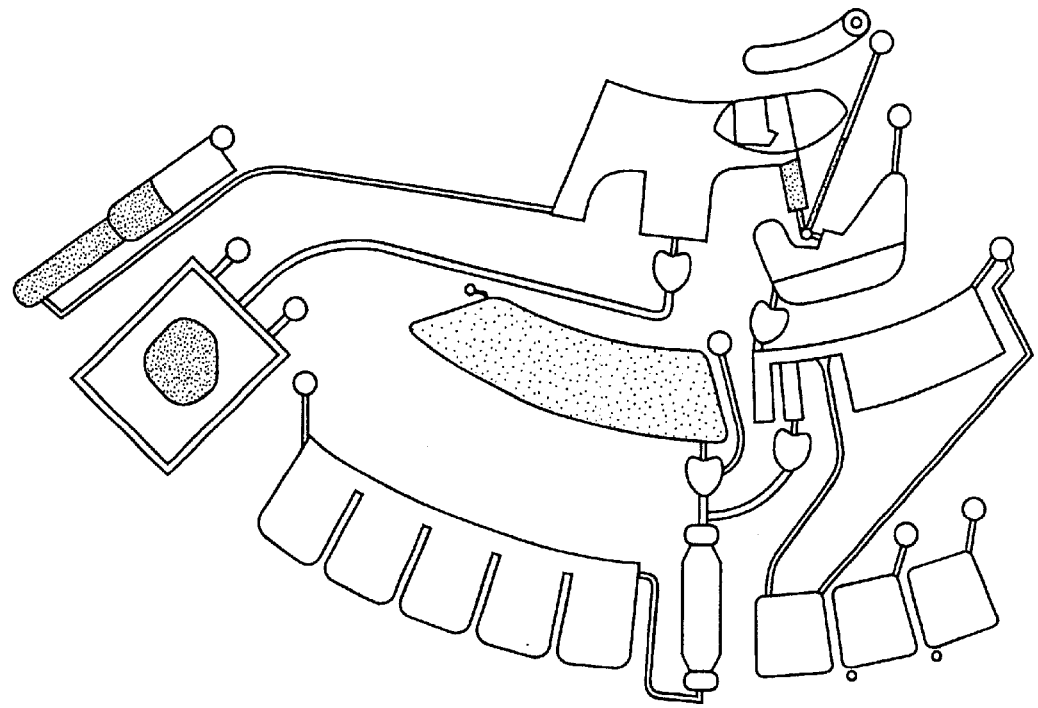
Figure 12H:
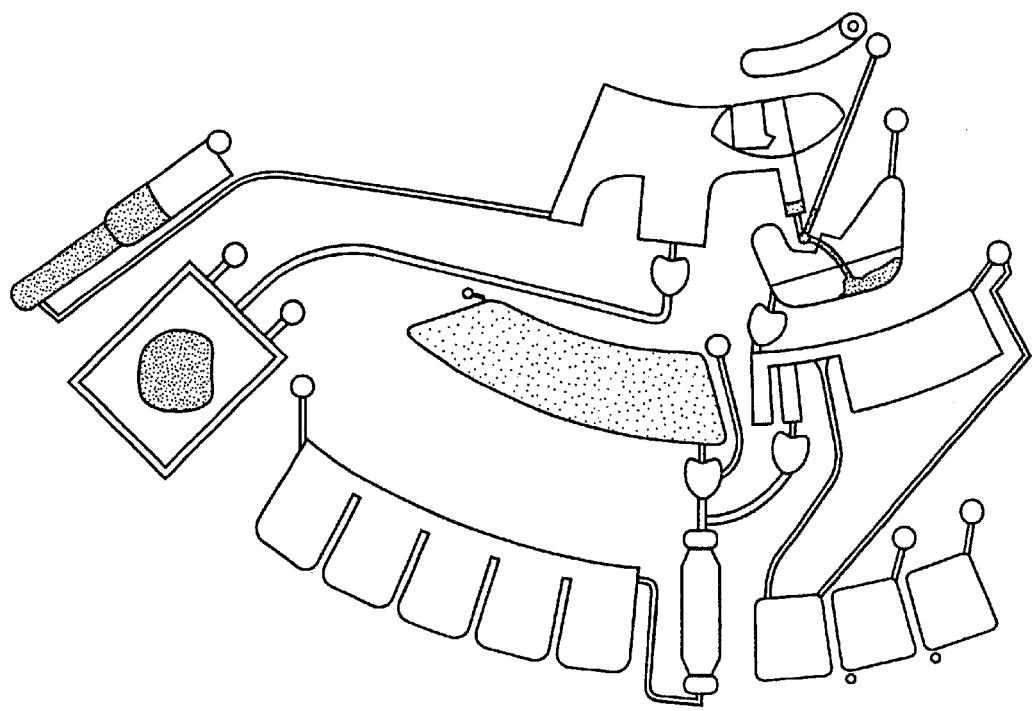
Figure 12I:
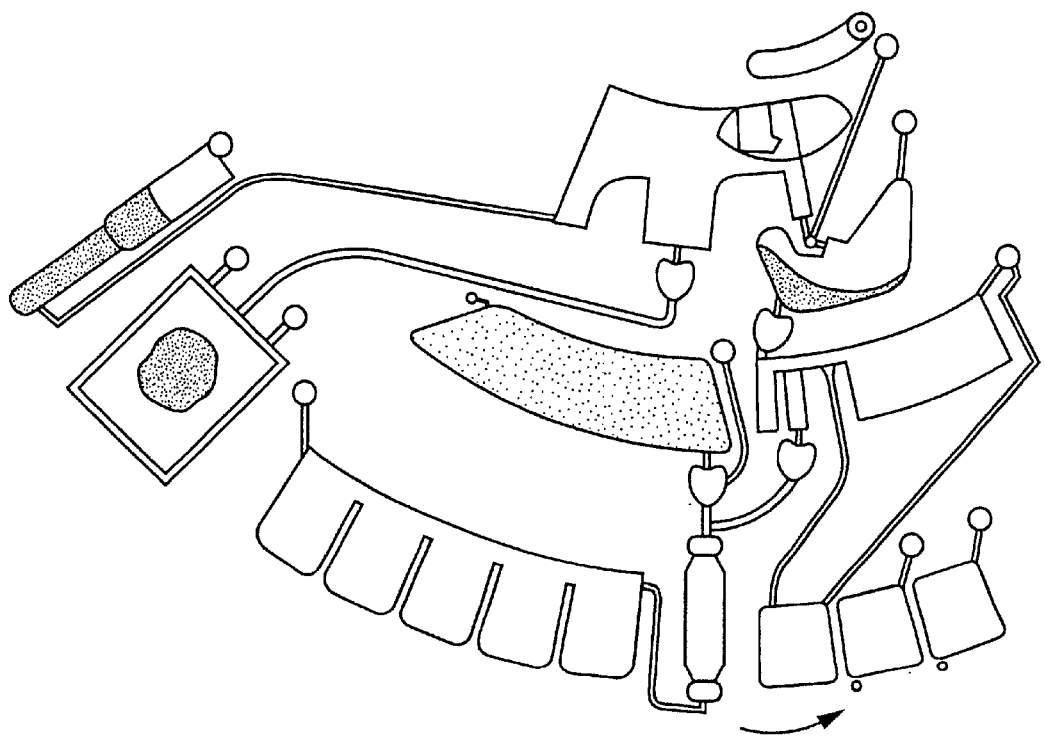
Figure 12J:
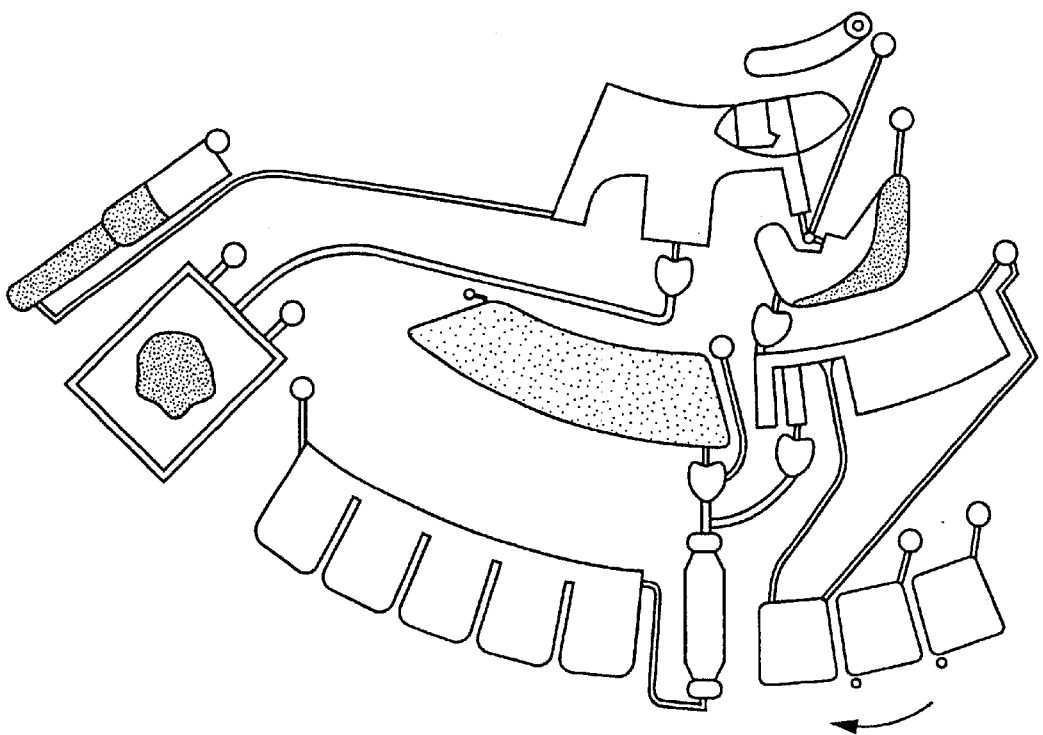
Figure 12K:
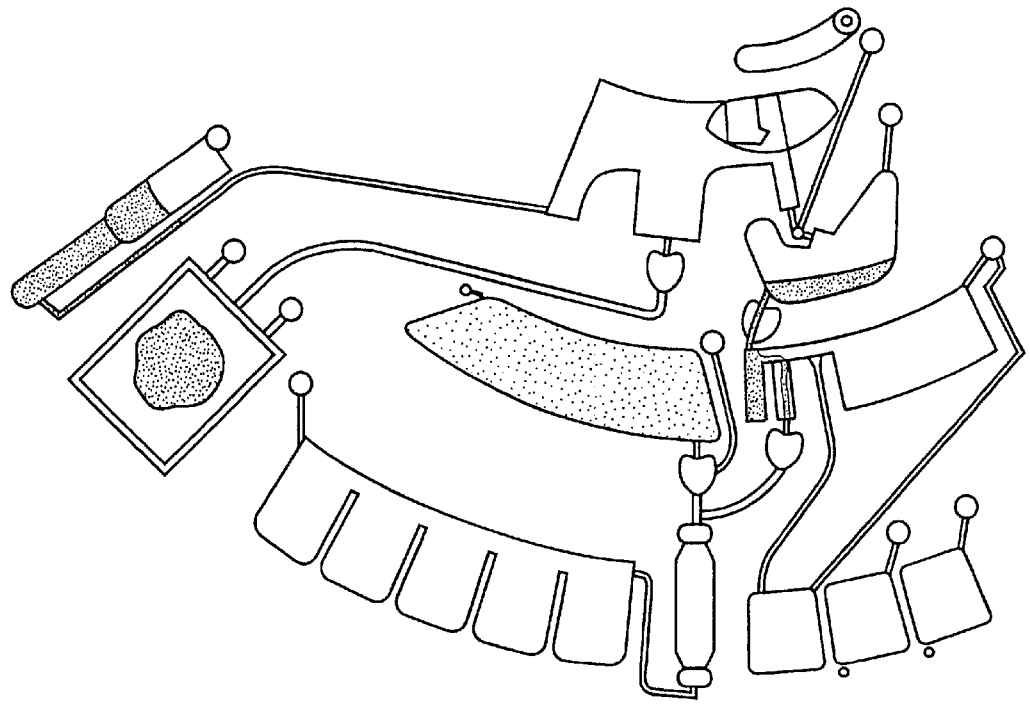
Figure 12L:
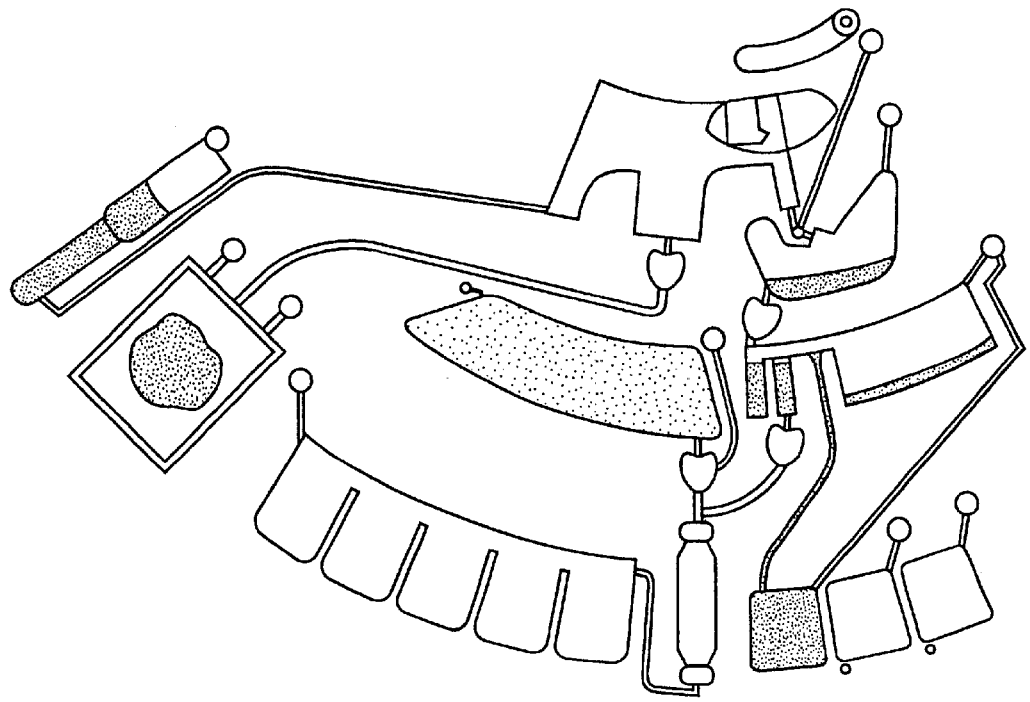
Figure 12M:
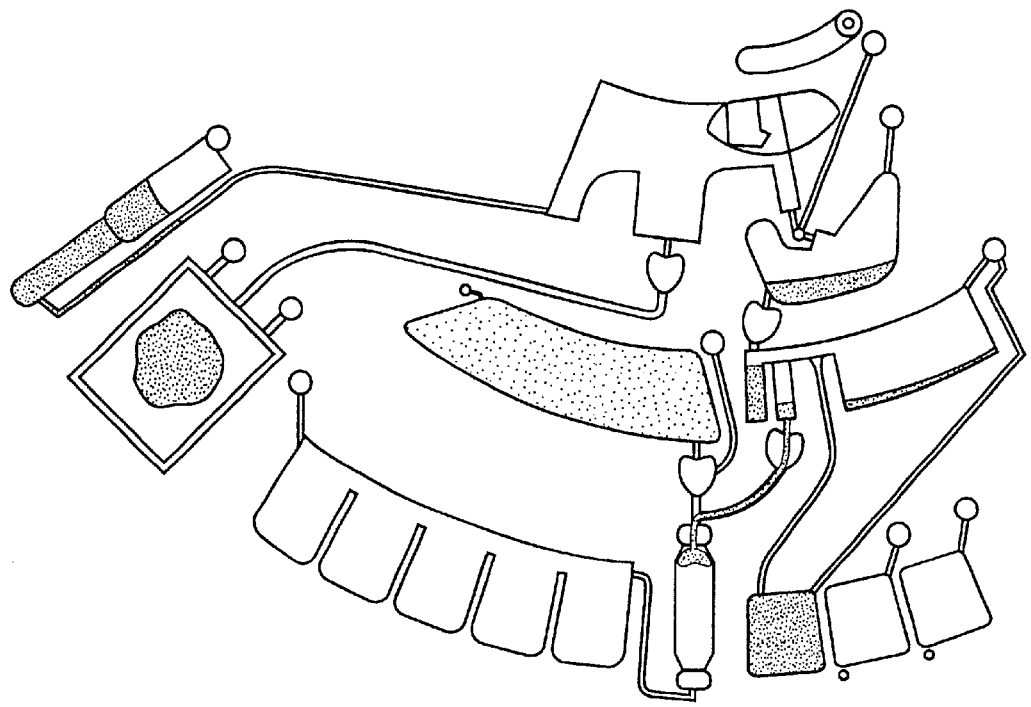
Figure 12N:
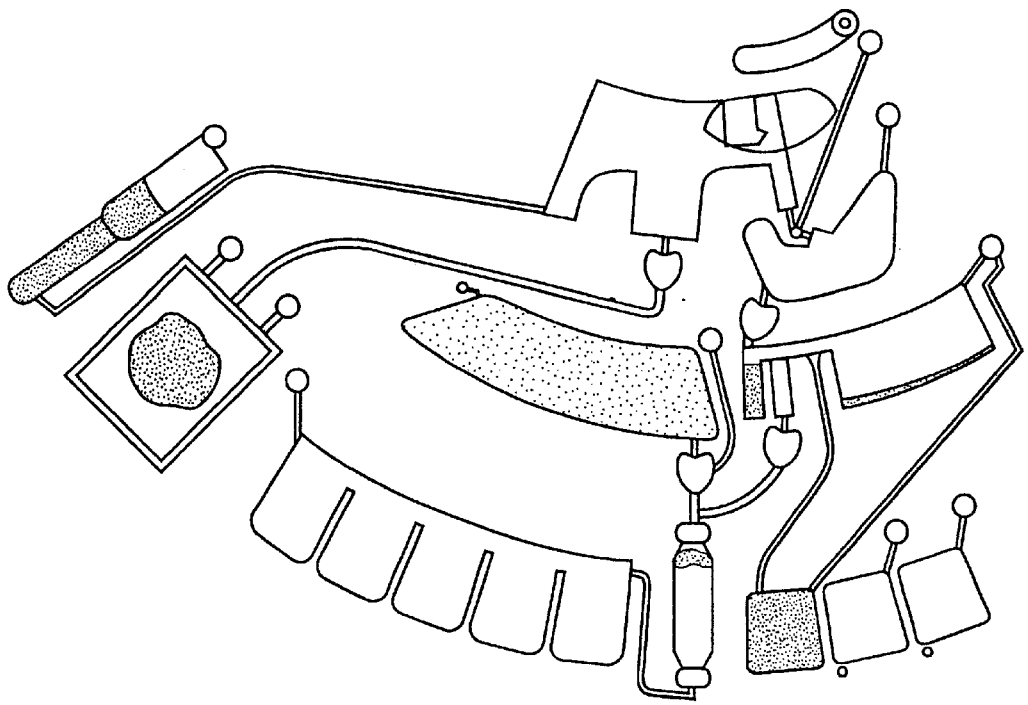
Figure 12O:
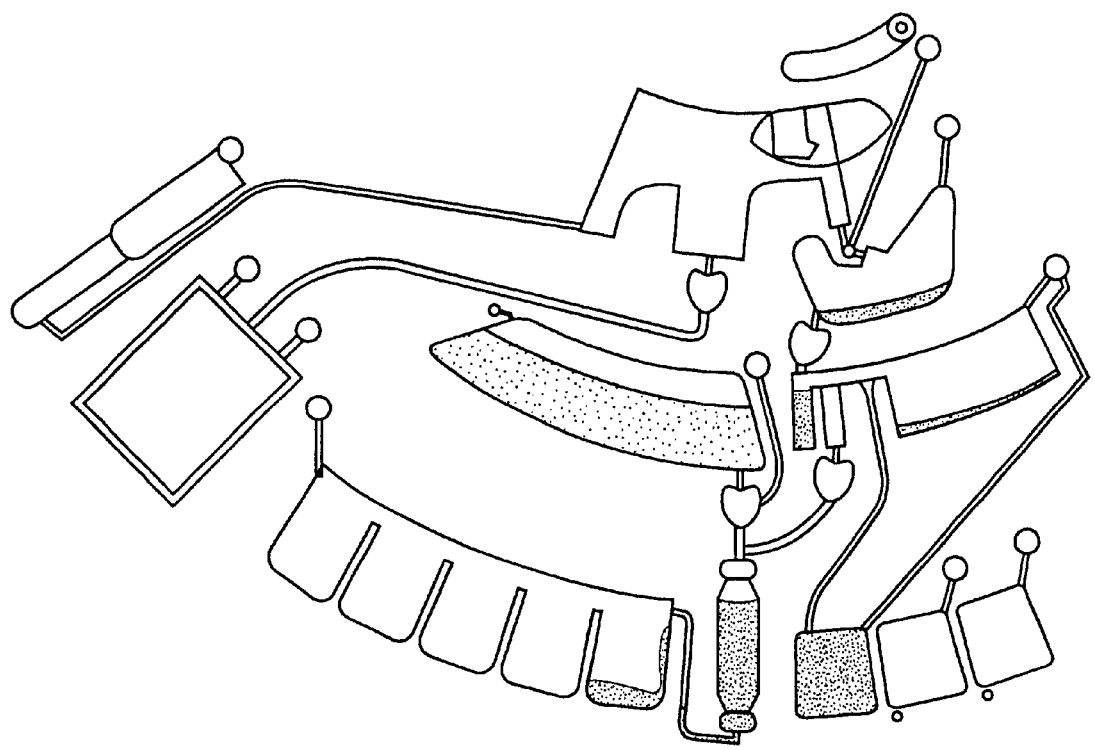
Figure 12P:
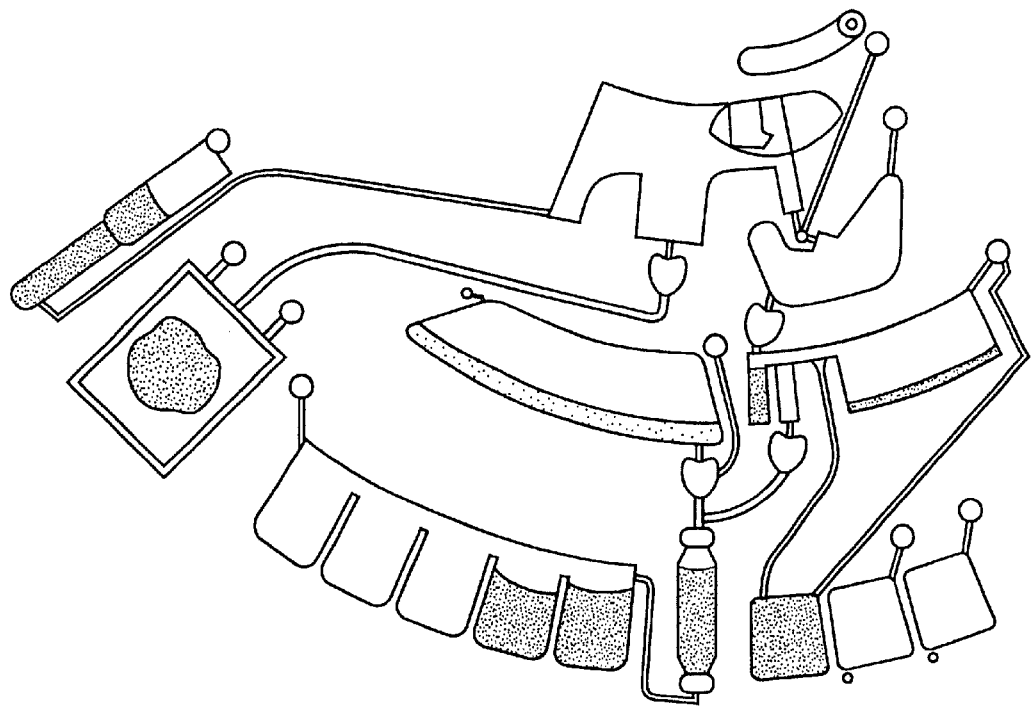
Figure 12Q:
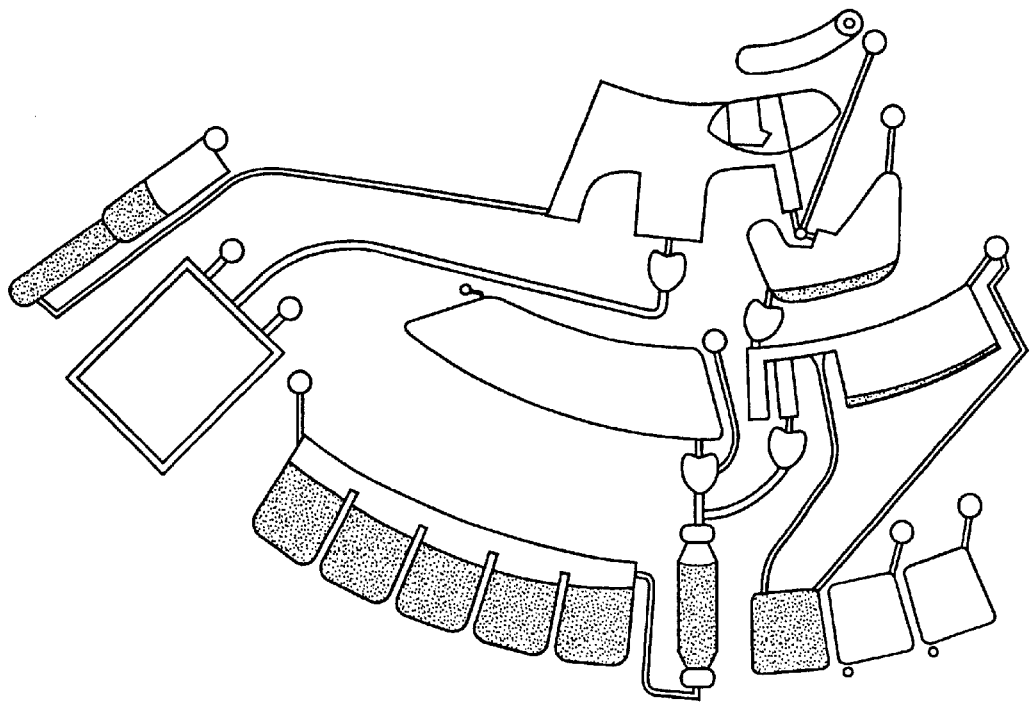

As illustrated in FIGS. 12A through 12Q, in the use of this platform a volume of blood from about 15 $\mu$L to about 150 $\mu$L is applied to entry port 1. Blood enters lysis subvolume 2 and lateral passageway 3 under the influence of gravity and capillary forces in the absence of rotation of the platform, as shown in FIG. 12A. Upon rotation of the platform at a first rotational speed $f_1$ of from about 50 rpm to about 1000 rpm, blood completely fills lysis subvolume 2 and also flows through passageway 3 and into blood glucose metering chamber 4 and overflow chamber 5, shown in FIG. 12B. Blood is retained in blood glucose chamber 4 either due to capillary pressure or by a sacrificial valve 6, most preferably a wax valve. Similarly, blood is retained in blood lysis subvolume 2 by a valve, most preferably a sacrificial valve 7. Excess blood flows at rotational speed $f_1$ through overflow channel 8 and into overflow chamber 9, shown in FIGS. 12C and 12D. Typical values for the first rotational speed are an acceleration of about 20 to about 60 rpm/sec to a final radial velocity of about 600 rpm.

After blood is metered and excess blood delivered to overflow chamber 9, the rotational speed of the disc is reduced to a rotational speed $f_{1a}$ of from about 0 rpm to about 500 rpm, typically to about 60 rpm, to perform a blanking measurement on sample collection cuvette array 12, total hemoglobin read chamber 23 and blood glucose assay chamber 11. Measurements of blanking cuvettes 13 and 14 are also advantageously performed.

The disc is then accelerated to a second rotational speed $f_2$ of about 200 rpm to about 2000 rpm, greater than $f_1$, and typically in the range of from about 800 rpm to about 1000 rpm. At this speed, capillary valve 6 is overcome or sacrificial valve 6 is released, and from about 1 $\mu$L to about 50 $\mu$L of blood from blood glucose metering chamber 4 flows through capillary 15 and into blood glucose assay chamber 11, shown in FIG. 12E. Upon entering assay chamber 11, blood fluid components are forced into absorbent matrix 10 through depression 11A. The blood fluid is incubated in matrix 10 for a time sufficient for the reagents 10A to produce a colored product 10B in an amount proportional to the amount of glucose in the blood fluid sample. The disc is slowed, typically to a rotational speed $f_4$ of from about 0 rpm to about 500 rpm, typically about 100 rpm, for glucose data acquisition using reflectance spectrometry; data acquisition as the disc is spinning down also enables to instrument to set t=0 for the assay, based on a decrease in reflectance when the matrix 10 is wet by the blood fluid components and hence the matrix's scattering decreases. Development of colored product 10B is shown in FIG. 12G.

The disc is then accelerated to rotational speed $f_3$ of about 500 rpm to about 3000 rpm, typically about 1000 rpm, with release of sacrificial valve 7A and fluid flow of from about 1 $\mu$L to about 50 $\mu$L, typically about 5 $\mu$L of blood from metered subvolume 2 through capillary 7 and into blood lysis chamber 16 containing from about 25 $\mu$L to about 90 $\mu$L, typically about 45 $\mu$L of blood lysis buffer. This is shown in FIG. 12H. The mixture of blood and blood lysis buffer in blood lysis chamber 16 is mixed by agitation, wherein the platform is accelerated repeatedly from about +2000 rpm/sec to −2000 rpm/sec (wherein + and − indicate rotation in different directions), typically from about 250–500 rpm/sec, over a time period of about 30 seconds to about 5 min, typically 1–2 min, as shown in FIGS. 12I and 12J.

The disc then is accelerated to a rotational speed $f_5$ from about 200 rpm to about 2000 rpm and typically about 750 rpm, and sacrificial valve 18 is released. Lysed blood from blood lysis chamber 16 flows through capillary 17 and into secondary metering structure 19, as shown in FIG. 12K. The lysed blood solution sequentially fills throwaway section 20, which is used as a trap for cell debris, metering section 21 and excess lysed blood then fills overflow section 24. Filling of metering chamber 21 is immediately followed by fluid flow through capillary 22 and filling of total hemoglobin read chamber 23. The disc is spun at rotational speed $f_5$ for a time sufficient to substantially completely drain blood lysis chamber 16. The configuration of the blood fluids on the disc after this spin is shown in FIG. 12L.

The disc is then accelerated to a rotational speed $f_7$ from about 200 rpm to about 3000 rpm and typically about 750 rpm, and sacrificial valve 26 is released. A metered volume of about 1 $\mu$L to about 50 $\mu$L, typically about 6 $\mu$L of lysed blood from metering section 21 flows through capillary 27 and into boronate affinity matrix chamber 28 (shown in FIG. 12M). The lysed blood solution is allowed to incubate in the chamber for a time from about 30 seconds to about 5 min, typically about 1 min, sufficient for glycated hemoglobin to bind to the matrix. This aspect of the disc is illustrated in FIG. 12N.

The disc is then accelerated to a rotational speed $f_7$ from about 500 rpm to about 3000 rpm and typically about 1000 rpm, and sacrificial valve 32 is released. A volume of about 250 $\mu$L to about 350 $\mu$L, typically about 290 $\mu$L of column wash buffer as described above flows from wash buffer reservoir 30 though capillary 31 and into boronate affinity matrix chamber 28 (shown in FIG. 12O). The wash buffer displaces the non-glycated hemoglobin and other components of the lysed blood fluid from the affinity column matrix and into sample collection cuvette array 12. FIGS. 12P through 12Q show sequential filling of the individual cuvettes in sample collection cuvette array 12. The rotation speed of the disc is reduced, to from about 0 rpm to about 500 rpm and typically to about 60 rpm for sample collection cuvette array 12 and total hemoglobin read chamber 23 to be interrogated spectrophotometrically. The glycated fraction of the blood sample is determined algorithmically by subtracting the non-glycated hemoglobin fraction in sample collection cuvette array 12 from the total hemoglobin detected in total hemoglobin read chamber 23.

2. Resistive Heater and Temperature Sensing Components

Temperature control elements are provided to control the temperature of the platform. The invention provides heating elements, specifically resistive heating elements, and elements for detecting temperature at specific positions on the platform. Heating devices are preferably arrayed to control the temperature of the platform over a particular and defined area, and are provided having a steep temperature gradient with distance on the platform from the heater.

Certain resistors, including commercially-available resistive inks (available from Dupont) exhibit a positive temperature coefficient (PTC), i.e., an increase in resistance with increasing temperature. Applying a fixed voltage across a PTC resistor screen-printed on a plastic substrate results in rapid heating, followed by self-regulation at an elevated temperature defined by the circuit design heat sink and ambient temperature. In such screen-printed resistors, connection to a power source is made by first printing parallel silver conductors followed by printing the PTC ink between the conductors.

A resistive heating element comprises a conductive ink connected with electrical contacts for activation of the heater, and resistive inks applied between the conductive ink and in electrical contact therewith, wherein application of a voltage (direct or alternating current) between the conductive inks results in current flow through the resistive inks and production of heat. There are two important types of resistive inks used in the resistive heating elements of this invention The first is a standard polymer thick film ink, such as Dupont 7082 or Dupont 7102 ink. These inks produce a surface temperature that is not self-limiting, and the temperature resulting from the use of these inks is dependent primarily on the magnitude of the applied voltage. In contrast, the positive temperature coefficient (PTC) inks show increase resistivity with increasing voltage, so that surface temperature is self-limiting because the amount of heat-producing current goes down as the applied voltage goes up. PTC inks are characterized as having a particular temperature where this self-limiting property is first exhibited; at voltages that produce temperatures less than the critical temperature, the amount of heat is dependent on the magnitude of the applied voltage.

Resistive inks useful according to the invention include Dupont 7082, 7102, 7271, 7278 and 7285, and other equivalent commercially available polymer thick film ink and PTC inks.

Conductive inks useful according to the invention include Dupont 5028, 5025, Acheson 423SS, 426SS and SS24890, and other equivalent commercially available conductive inks.

Additional components of the dielectric layer that serves to insulate the electrical circuit. Dielectric layers advantageously comprise dielectric inks such as Dupont 5018A. Insulation can also be achieved using pressure sensitive transfer adhesive such as 7952MP (3M Co.), or a pressure sensitive transfer adhesive deposited onto a polyester carrier layer such as 7953MP (3M Co.) or thermoplastic bonding films such as 3M 406, 560 or 615.

Resistive heaters of the invention are advantageously used to incubate fluids at a stable temperature and for melting sacrificial valves as described below, and also for thermal cyclic.

Resistive and conductive inks are preferably screen-printed using methods and techniques well known in the art. See Gilleo, 1995, *Polymer Thick Film* (Van Nostrand Reinhold). Inks are typically screen printed to a thickness of about 10 microns; however, repetitive screen printing of resistive inks can be used to deposit thicker layers having reduced resistances. Both conductive and resistive inks are heat cured, typically at between 110° C. and 120° C. for about 10 minutes. The outline of this printing process is shown in FIG. 30. Importantly, each of the layers must be correctly registered with one another for resistive heating to be, provided. Heaters can be screen printed to any required size; a minimum area for a screen-printed heater has been determined to be about 0.25 mm$^2$ (0.5 mm×0.5 mm).

The ability to tailor the resistance (and hence the temperature profile) of the resistive heaters using choice of ink formulation and reprinting of heater circuits provides control of the final electrical and thermal properties of the resistive heating elements of the invention. The resistance can also be controlled through connection of series and parallel configurations of resistive elements.

3. Sacrificial Valves

The ability to specifically generate heat at a particular location on a microsystems platform of the invention also enables the use of sacrificial valves that can be released or dissolved using heat. For the purposes of this invention, the term "sacrificial valve" is intended to encompass materials comprising waxes, plastics, and other material that can form a solid or semi-solid fluid-tight obstruction in a microchannel, capillary, chamber, reservoir or other microfluidics component of the platforms of the invention, and that can be melted or deformed to remove the obstruction with the application of heat. Sacrificial valves are preferably made of a fungible material that can be removed from the fluid flow path. In preferred embodiments, said sacrificial valves are wax valves and are removed from the fluid flow path by heating, using any of a variety of heating means including infrared illumination and most preferably by activation of resistive heating elements on or embedded in the platform surface as described herein. For the purposes of this invention, the term "wax" is intended to encompass any solid, semi-solid or viscous liquid hydrocarbon, or a plastic. Examples include mondisperse hydrocarbons such as eicosane, tetracosane and octasone, and polydisperse hydrocarbons such as paraffin. In the use of wax sacrificial valves, application of a temperature higher than the melting temperature of the wax melts the valve and removes the occlusion from the microchannel, capillary or other fluidic component of the microsystems platforms of the invention. Particularly when the sacrificial valve is melted on a rotating microsystems platform of the invention, the melted wax to flow through the microchannel, capillary or other fluidic component of the microsystems platforms of the invention and away from the original site of the valve.

One drawback, however, is the possibility that the wax will recrystallize as it flows away from the original valve site, and concomitantly, away from the localized heat source. Recrystallization results in re-occlusion of the microchannel, capillary or other fluidic component of the microsystems platforms of the invention, potentially and most likely at a site other than the site of a localized heat source, and therefore likely to foul fluid movement on the disc. One solution for this problem is the inclusion in the sacrificial wax valves of the invention of a wax recrystallization chamber positioned downstream from the position of the wax valve. Preferably, the wax recrystallization chamber is fluidly connected with the microchannel, capillary or other fluidic component of the microsystems platforms of the invention that was occluded by the wax sacrificial valve. Typically, the wax recrystallization chamber is a widening of the microchannel, capillary or other fluidic component of the microsystems platforms of the invention so that recrystallized wax can harden on the walls of the microchannel, capillary or other fluidic component of the microsystems platforms of the invention with enough distance between said walls that the recrystallized wax does not re-occlude the microchannel, capillary or other fluidic component of the microsystems platforms of the invention. Preferably, the heating element, most preferably the resistive heating element of the invention, extends past the site of the wax valve and overlaps at least a portion of the wax recrystallization chamber, thereby retarding the propensity of the wax valve to recrystallize.

It is also recognized that this propensity of wax valves to recrystallize can be exploited to create a wax valve at a particular location in a microchannel, capillary or other fluidic component of the microsystems platforms of the invention. In this embodiment, a particular location can be kept below a threshold temperature by failing to apply heat at that location, and a wax valve material can be mobilized from a storage area on a platform by heating and them allowed to flow under centripetal acceleration to a particularly cold site where a wax valve is desired. An advantage of wax valves in this regard is that the proper positioning an activation of resistive heater elements enables flexibility in choosing when and whether a particular microchannel, capillary or other fluidic component of the microsystems platforms of the invention is to be occluded by a wax sacrificial valve.

In particularly preferred embodiments, the sacrificial valves of the invention comprise a cross-linked polymer that displays thermal recover, most preferably a cross-linked, prestressed, semicrystalline polymer; an example of a commercially available embodiment of such a polymer is heat recoverable tubing (#FP301H, 3M Co., Minneapolis, Minn.). Using these materials, at a temperature less than the melting temperature ($T_m$), the polymer occludes a microchannel, capillary or other fluidic component of the Microsystems platforms of the invention. At a temperature greater than $T_m$, however, the polymer reverts to its prestressed dimensions by shrinking. Such shrinking is accompanied by release of the occlusion from the microchannel, capillary or other fluidic component of the microsystems platforms of the invention. Such embodiments are particularly preferred because the polymer remains in situ and does not recrystallize or otherwise re-occlude the microchannel, capillary or other fluidic component of the Microsystems platforms of the invention. Also, such embodiments do not require the more extensive manipulation in preparing the platforms of the invention that wax valves require.

In another embodiment, the sacrificial valves of the invention comprise a thin polymeric layer or barrier dividing two liquid-containing microchannel, capillary or other fluidic component of the microsystems platforms of the invention, that can burst when sufficient temperature and/or pressure is applied.

Another embodiment of the sacrificial valves of the invention are provided wherein a screen-printed resistive heater element is itself a valve. In this embodiment, the resistive heater element is screen-printed on a substrate such as polyester that divides two liquid-containing microchannel, capillary or other fluidic component of the microsystems platforms of the invention. In these embodiments, localized application of heat using a resistive heating element is used to melt the substrate dividing the liquid-containing microchannel, capillary or other fluidic component of the Microsystems platforms of the invention. Preferably, in this embodiment the two liquid-containing microchannel, capillary or other fluidic component of the Microsystems platforms of the invention are positioned in adjacent layers through the vertical thickness of the platform.

As described above, the screen-printed resistive heater elements of this invention provide localized application of heat to a microsystems platform. The degree of localization achieved using these resistive heating elements is sufficient to provide for the placement of two adjacent sacrificial valves separated by a distance of 0.15 cm.

4. Detectors and Sensors

Detection systems for use on the microsystem platforms of the invention include spectroscopic, electrochemical, physical, light scattering, radioactive, and mass spectroscopic detectors. Spectroscopic methods using these detectors encompass electronic spectroscopy (ultraviolet and visible light absorbance, fluorescence, luminescence, and refractive index), vibrational spectroscopy (IR and Ramar), and x-ray spectroscopies (x-ray fluorescence and conventional x-ray analysis using micromachined field emitters, such as those developed by the NASA Jet Propulsion Lab, Pasadena, Calif.).

General classes of detection and representative examples of each for use with the microsystem platforms of the invention are described below. In addition, the detection implementation systems utilizing.the detectors of the invention can be external to the platform, adjacent to it or integral to the disk platform.

Spectroscopic Methods:

1. Fluorescence

Fluorescence detector systems developed for macroscopic uses are known in the prior art and are adapted for use with the microsystem platforms of this invention. For example, an excitation source such as a laser is focused on an optically-transparent section of the disk. Light from any analytically-useful portion of the electromagnetic spectrum can be coupled with a disk material that is specifically transparent to light of a particular wavelength, permitting spectral properties of the light to be determined by the product or reagent occupying the reservoir interrogated by illumination with light. Alternatively, the selection of light at a particular wavelength can be paired with a material having geometries and refractive index properties resulting in total internal reflection of the illuminating light. This enables either detection of material on the surface of the disk through evanescent light propagation, or multiple reflections through the sample itself, which increases the path length considerably.

Alternative configurations appropriate for evanescent wave systems are provided as understood in the art (see Glass et al., 1987, Appl. Optics 26: 2181–2187). Fluorescence is coupled back into a waveguide on the disk, thereby increasing the efficiency of detection. In these embodiments, the optical component preceding the detector can include a dispersive element to permit spectral resolution. Fluorescence excitation can also be increased through multiple reflections from surfaces in the device whenever noise does not scale with path length in the same way as with signal.

In another type of fluorescence detection configuration, light of both the fluorescence excitation wavelength and the emitted light wavelength are guided through one face of the device. An angle of 90 degrees is used to separate the excitation and collection optical trains. It is also possible to use other angles, including 0 degrees, whereby the excitation and emitted light travels colinearly. As long as the source light can be distinguished from the fluorescence signal, any optical geometry can be used. Optical windows suitable for spectroscopic measurement and transparent to the wavelengths used are included at appropriate positions (i.e., in "read" reservoir embodiments of detecting chambers) on the disk. The use of this type of fluorescence in macroscopic systems has been disclosed by Haab et al. (1995, *Anal. Chem.* 67: 3253–3260).

2. Absorbance Detection

Absorbance measurements can be used to detect any analyte that changes the intensity of transmitted light by specifically absorbing energy (direct absorbance) or by changing the absorbance of another component in the system (indirect absorbance). Optical path geometry is designed to ensure that the absorbance detector is focused on a light path receiving the maximum amount of transmitted light from the illuminated sample. Both the light source and the detector can be positioned external to the disk, adjacent to the disk and moved in synchrony with it, or integral to the disk itself. The sample chamber on the disk can constitute a cuvette that is illuminated and transmitted light detected in a single pass or in multiple passes, particularly when used with a stroboscopic light signal that illuminates the detection chamber t a frequency equal to the frequency of rotation or multiples thereof Alternatively, the sample chamber can be a planar waveguide, wherein the analyte interacts on the face of the waveguide and light absorbance is the result of attenuated total internal reflection (i.e., the analyte reduces the intensity source light if the analyte is sequestered at the surface-of the sample chamber, using, for example, specific binding to a compound embedded or attached to the chamber surface; see Dessy, 1989, *Anal. Chem.* 61: 2191).

Indirect absorbance can be used with the same optical design. For indirect absorbance measurements, the analyte does not absorb the source light; instead, a drop in absorbance of a secondary material is measured as the analyte displaces it in the sample chamber. Increased transmittance therefore corresponds to analyte concentration.

3. Light Scattering

Turbidity can also be measured on the disk. Optics are configured as with absorbance measurements. In this analysis, the intensity of the transmitted light is related to the concentration of the light-scattered particles in a sample. An example of an application of this type of detection method is a particle agglutination assay. Larger particles sediment in a rotating disk more rapidly than smaller particles, and the turbidity of a solution in the sample chamber before and after spinning the disk can be related to the size of the particles in the chamber. If small particles are induced to aggregate only in the presence of an-analyte, then turbidity measurements can be used to specifically detect the presence of an analyte in the sample chamber. For example, small particles can be coated with an antibody to an analyte, resulting in aggregation of the particles in the presence of the analyte as antibody from more than one particle bind to the analyte. When the disk is spun after this interaction occurs, sample chambers containing analyte will be less turbid that sample chambers not containing analyte. This system can be calibrated with standard amounts of analyte to provide a gauge of analyte concentration related to the turbidity of the sample under a set of standardized conditions.

Other types of light scattering detection methods are provided for use with the Microsystems platforms and devices of the invention. Monochromatic light from a light source, advantageously a laser light source, is directed across the cross-sectional area of a flow channel on the disk. Light scattered by particles in a sample, such as cells, is collected at several angles over the illuminated portion of the channel (see Rosenzweig et al., 1994, *Anal. Chem.* 66: 1771–1776). Data reduction is optimally programmed directly into the device based on standards such as appropriately-sized beads to relate the signal into interpretable results. Using a calibrated set of such beads, fine discrimination between particles of different sizes can be obtained. Another application for this system is flow cytometry, cell counting, cell sorting and cellular biological analysis and testing, including chemotherapeutic sensitivity and toxicology.

Analytic Methods

It will be understood that the interpretation of the optical detection data from performance of analytical assays as provided by the invention may require transformation of "raw" data into information useful for the operator. For example, "reflectance" is determined as the difference between the "signal" and the "dark signal" (i.e., the signal detected in the absence of transmitted light), normalized by the difference between the "reference" and the "dark reference," wherein each of the reference values is determined for a "blank" cuvette not containing a sample. Similarly, the detection methods used by the invention also include methods for eliminating artifactual signal produced by interfering absorbing or light-scattering components, such as scratches or particulate matter. Advantageously, normalized readings are collected at a wavelength greater than 650 nm, more preferably 660±10 nm as a reference. This reading is then subtracted from the sample reading to as a correction thereof.

Absorbance from certain components of biological fluid sample, such as hemoglobin in blood, are advantageously removed by using a light source with a wavelength at the absorbance peak of the interfering material; for hemoglobin, this is about 425 nm. In preferred embodiments, light of this wavelength is provided by a blue light-emitting diode (LED) having a wavelength of about 430 nm. The light emission profile of the LED was found to overlap sufficiently with the hemoglobin absorbance profile to effectively quench the hemoglobin absorbance signal in the glucose assays of the invention. The glucose signal was then further treated analytically by subtracting a factor times the (blue-red) signal from the (orange-red) signal, wherein the (orange) signal was the wavelength specific for the glucose assay product. The factor used is dependent on the optics, the reading chamber structure, spectral properties of the light sources and filters, and the spectral absorbance characteristics of hemoglobin and the colored product of the glucose oxidase reaction. The factor can be determined empirically using solutions of known glucose and hemoglobin concentrations, both singly and in combination.

It will be understood in the art that similar combinations of light sources and interrogated wavelengths can be advantageously used to reduce or eliminate the contribution of other interfering species in optical detection methods used according to the invention.

5. Chemistries

As described above with regard to the microfluidic components of the microsystems platforms of the invention, the present invention provides platforms for performing chemical, biochemical, enzymatic, immunological and other assays on fluid samples, most preferably wherein the fluid sample is a biological fluid sample.

Two exemplary types of assay formats are explicitly set forth herein; one of ordinary skill will recognize that the disclosure is generally applicable to a variety of assay systems as set forth, for example, in *CLINICAL GUIDE TO LABORATORY TESTS*, Tibet, ed., W. B. Sanders Co: Philadelphia, 1995. A representative and non-limiting sample of assays advantageously performed using the microsystems platforms of the invention are set forth in Table I below.

TABLE I

| Assay for: | Analyte/Detection Type | Components on solid phase: |
| --- | --- | --- |
| Acid Phosphatase | enzyme/colorimetric | Alpha-naphthol phosphate, Fast Red TR dye[1] |
| Alanine Aminotransferase | enzyme/colorimetric | Alanine, alpha-ketoglutarate, 2,4-dinitrophenylhadrazine dye |
| Albumin | protein/colorimetric | Bromcresol green dye |
| Alkaline Phosphatase | enzyme/colorimetric | p-nitrophenyl phosphate |
| Amylase | enzyme/colorimetric | 4,6-ethylidine(G7)-p-nitrophenyl(G1)-alpha,D-maltoheptaside, alpha-glucosidase |
| Apolipoprotein A-1 | lipoprotein/immuno-turbidimetric | Anti-ApoA1 antibody, polyethylene glycol[2] |
| Direct Bilirubin | organic compound/colorimetric | Diazotized sulfanilic acid |
| Total Bilirubin | organic compound/colorimetric | Caffeine, benzoate, acetate, diazotized sulfanilic acid |
| Calcium | mineral/colorimetric | Cresolphthalein complexone |
| Cholesterol | lipid/colorimetric | Cholesterol esterase, cholesterol oxidase, 4-aminoantipyrine, p-hydroxybenzene sulfonate |
| Fructosamine | glycated serum protein/colorimetric | Nitroblue tetrazolium |
| Gamma-glutamyl transferase | enzyme/colorimetric | L-gamma-glutamyl-3-carboxy-4-nitroanilide, glycylglycine |
| Iron | mineral/colorimetric | Ferrozine, reducing agent |
| Microprotein (urine or CSF) | protein/colorimetric | Pyrogallol red-molybdate complex |
| Urea | organic compound/colorimetric | Diacetylmonoxime, heat |
| Specific Protein species, subspecies or variant | immunologically reactive proteins/immunoturbidimetry | Antibody reactive with unique species, etc, site; precipitation enhancers (e.g., anti-alpha-1-antitrypsin IgG, polyethylene glycol)[3] |
| Antibodies against infectious agents | immunoreaction to bacteria or virus infection/heterogeneous enzyme immunoassay | Immunoreactive component from infective agent, enzyme linked to antibody against the primary immunoglobulin species of reaction to the agent, enzyme substrate linked to color generation (e.g., Epstein-Barr early antigen, anti-human IgG conjugated to horseradish peroxidase, 3-3'-5-5'-tetramethylbenzidine) |
| Drugs | immunologically reactive therapeutic drugs or drugs of abuse/homogeneous enzyme immunoassay | Competition between drug and drug-enzyme reagent for anti-drug antibody binding sites where antibody binding inhibits enzyme activity, enzyme substrate linked to color generation (e.g., phenobarbital-glucose-6-phosphatase, anti-phenobarbital IgG, AND)[4] |

[1] Saw, D., et. al, Clin. Biochem., 1990; 23:505.
[2] Rifai, N., Warnick, G. R., eds., Methods for Clinical Laboratory Measurement of Lipid and Lipoprotein Risk Factors, Washington, D.C.; AACC Press, 1990
[3] Hills, L. P., and Tiffany, T. O., Comparison of turbidimetric and light-scattering measurements of immunoglobulins by use of a centrifugal analyzer with absorbance and fluorescence/light scattering optics. Clin. Chem. 1980; 26:1466.

The requirements for performing such assays on the solid phase (such as the matrices disclosed herein) include: the ability to link, by one or a series of chemical reaction steps, the presence of an analyte of interest in a fluid sample, most preferably a biological fluid sample, to the quantitative generation of a product detectable by optical methods as disclosed herein; stabilization of the necessary reagents (chemicals or biochemicals) onto the solid phase so that the reagents retain their potencies or activities.

A second general scheme for performing assays on the Microsystems platforms of the invention involve miniaturized versions of affinity chromatography column separations, wherein the analyte specifically binds to a material in a chamber or on a surface, most preferably a derivatized surface, of the platform, or is bound to a material such as a bead, chromatography resin, or membrane on the surface of the platform, so that the remainder of the fluid sample can be washed from the affinity matrix and the analyte separated thereby. In certain preferred embodiments, the analyte is detected indirectly, wherein the biological fluid sample is interrogated after passage of the sample over the chromatography matrix. Such detection methods can be subtractive, wherein the interrogated optical property of the biological fluid sample after passage over the chromatography matrix is compared with the same property of a portion of the sample that has not been passed over the matrix; or directly, wherein the analyte is dissociated from the chromatography matrix (either non-specifically, using for example a salt or dielectric gradient, or specifically, using a binding competitor that displaces the analyte from the chromatography matrix).

Examples of analytes advantageously separated from biological fluid samples and the column affinity material(s) used therefore are set forth in Table II.

TABLE II

| Column Affinity Material | Bound Species |
| --- | --- |
| Diatomateous earth | DNA |
| Protein A-agarose | IgG |
| Heparin-agarose | coagulation proteins, Protein C, growth factors, lipoproteins, steroid receptors |
| Blue agarose | albumin, coagulation factors, interferon, enzymes requiring cofactors with adenyl group |
| Streptavidin-agarose | biotinylated molecules |
| Con A-agarose | glycoproteins, polysaccharides with terminal mannose or glucose |

TABLE II-continued

| Column Affinity Material | Bound Species |
| --- | --- |
| Lentil lectin-agarose | glycoproteins, polysaccharides with branched mannose with frucose linked α(1,6) to N-acetyl-glucosamine |
| Wheat gern lectin-agarose | glycoproteins, polysaccharides with chitobiose core of N-linked oligosaccharides |
| Peanut lectin-agarose | glycoproteins, polysaccharides with terminal β-galactose |
| Arginine-agarose | serine proteases |
| Calmodulin-agarose | ATPases, phosphodiesterases, neurotransmitters, protein kinases |
| Gelatin-agarose | Fibronectin |
| Glutathione-agarose | S-transferases, glutathione-dependent proteins |
| Lysine-agarose | plasminogen, plasminogen activator, ribosomal RNA |
| DNA (denatured)-agarose | DNA polymerase, RNA polymerase, T4 polynucleotide kinase, exonuclease, deoxyribonucleases |
| DNA (native)-cellulose | Glucocorticoid receptor, DNA polymerase, DNA binding proteins |
| 2'5' ADP-agarose | NADP-dependent dehydrogenases |
| 5' AMP-agarose | NAD-dependent dehydrogenases, ATP-dependent kinases |
| 7-Methyl-GTP-agarose | eukaryotic mRNA, cap-binding protein |
| Poly(U)-agarose | mRNA, reverse transcriptase, interferon, plant nucleic acids |
| C8-silica | Proteins |

It will be appreciated that preparative embodiments of the affinity chromatographic column separations are within the scope of the invention.

The following Examples are intended to further illustrate certain preferred embodiments of the invention and are not limiting in nature.

EXAMPLE 1

Blood Glucose Assay Fluidics Structure

A microsystems platform provided by the invention and specifically designed for performing blood glucose assay is illustrated in FIG. 1. Disk embodiments of the platforms of the invention were fashioned from machined acrylic. The overall disc dimensions include an outer radius of about 6 cm and an inner radius of about 0.75 cm, wherein the disk was mounted on the spindle of a rotary device. The thickness of the fluidics disc was 3.2 mm, which was mounted on a conventional compact disc (CD) having a thickness of 1.2 mm. All surfaces coming into contact with blood on the platform are advantageously treated with heparin, EDTA or other anticoagulants to facilitate fluid flow thereupon.

The components of the blood glucose assay were prepared as follows. Blood sample entry port chamber 101 having a depth in the platform surface of about 0.32 cm and lateral dimensions of about 1 cm was constructed on the platform, and designed to accommodate a volume of 100 μL. This entry port was fluidly connected with a metering capillary 102 having a square cross-sectional diameter of about 0.1 cm deep×0.5 cm wide and proximal ends rounded with respect to entry port 101; the length of this metering capillary array was sufficient to contain a total volume of about 16 μL. The entry port was also fluidly connected with an overflow capillary 103 having a cross-sectional diameter of about 0.05 cm×0.075 cm and proximal ends rounded with respect to entry port 101. The overflow capillary was fluidly connected with a two-layered overflow chamber 105 having a first depth in the platform of about 0.025 cm and a second depth in the platform of about 0.25 cm, greater than the depth of the overflow capillary 103. Metering capillary 102 was fluidly connected to metered blood fluid chamber 104 having a depth in the platform surface of 1 mm and greater than the depth of the metering capillary 102. Each of the overflow and fluid chambers was also connected with air ports or air channels, such as 114, that have dimensions of 0.025 cm deep and permitted venting of air displaced by fluid movement on the platform. A capillary junction 115 that was 0.051 cm deep was present in the air channel to prevent fluid flow into the air channel.

Entry port 101 was positioned on the platform about 2 cm from the center of rotation. Metering chamber 102 extended about 1 cm from entry port 101. The extent of the length of overflow capillary 103 was 300% greater than the extent of the length of metering capillary 102. The position of blood fluid chamber 104 was about 4.6 cm from the center of rotation, and the position of overflow chamber 105 was about 4 cm from the.axis of rotation.

Blood fluid chamber 104 acted as a capillary barrier that prevented fluid flow from metering chamber 102 at a first, non-zero rotational speed $f_1$ of about 300 rpm that was sufficient to permit fluid flow comprising overflow from the entry port 101 through overflow capillary 103 and into overflow chamber 105. This capillary boundary was constructed to be overcome at a second rotational speed $f_2$ of about 600 rpm (so that $f_2 > f_1$). Blood fluid chamber 104 was fluidly connected to capillary 110 that was about 0.025 cm deep and had a cross-sectional diameter of about 0.025 cm and was connected to capillary or sacrificial valve 111. Sacrificial valve 111 was further fluidly connected with capillary 112 that was about 0.25 mm deep and had a cross-sectional diameter of about 0.05 cm, and capillary 112 was fluidly connected to assay chamber 107. Sacrificial valve chamber 111 was positioned to sequester melted wax produced by release of the sacrificial valve. Assay chamber 107 comprised a depression in the surface of the platform having a depth of about 0.1 cm, and further comprised a circular or rectangular concave depression 113 connected to capillary 112. Assay chamber 107 also comprised a pad or matrix 106 comprising a positively-charged nylon matrix having a pore size of about 0.8 μm. The pore size of matrix 106 was chosen to inhibit or prevent blood cell entry into the matrix. The matrix was positioned in assay chamber 107 to be in fluidic contact with depression 113, covering depression 113 and having a surface area greater than the surface area of depression 113. The matrix was impregnated with immobilized reagents 108 which produce a detectable product proportional to the concentration of glucose in a blood sample. The detectable product was a colored product 109, i.e., a product absorbing light at a detectable, visible wavelength.

As illustrated in FIGS. 2A through 2E, in the use of this platform an imprecise volume (about 30 μL of fluid) of blood was applied to the entry port 101. The fluid wicked into air channel 114 and was stopped by capillary junction 115. Fluid also wicked into metering capillary 102 and overflow capillary 103. Fluid flowed through the metering capillary 102 and overflow capillary 103 at no rotational speed until the fluid reached capillary junctions at the junction between metering chamber 102 and blood fluid chamber 104 and overflow capillary 103 and overflow chamber 105. Metering capillary 102 was constructed to define a precise volume of about 15 μL of blood between entry port 101 and the capillary junction at fluid chamber 104, which was designed to be at least the amount of the fluid placed by the user in entry port 101.

After sample loading by a user and filling of metering chamber 102 and overflow capillary 103 at zero rotational speed, the platform was spun at a first rotational speed $f_1$ of about 300 rpm, which was sufficient to motivate fluid flow through the overflow capillary 103 in this microfluidics array, wherein entry port 101 had a depth of about 0.3 cm, metering chamber 102 had dimensions of about 0.1 cm deep×0.4 cm wide in cross-section and about 0.5 cm in length from the center of rotation, and overflow capillary 103 had dimensions of about 0.05 cm×0.075 cm in cross-section and about 2.7 cm in length from the center of rotation.

Due to the greater distance from the center of rotation of the end of overflow capillary 103 than the end of metering chamber 102, at rotational speed $f_1$ fluid flowed through overflow capillary 103 into overflow chamber 105. The platform was spun until all excess fluid was evacuated from entry port 101 and into overflow chamber 105, except the fluid contained in metering capillary 102.

At a second rotational speed $f_2$ of about 1000 rpm, the precise amount of fluid (16 μL) contained in metering capillary 102 was delivered into fluid chamber 104. Fluid movement into fluid chamber 104 was accompanied by filling of capillary 110.

In embodiments comprising a sacrificial valve 111 in-line with capillary 110 at a position between capillary 110 and 112 shown in FIG. 2A, release of the sacrificial valve resulted in fluid flow through capillary 112 and into assay chamber 107. In said embodiments, fluid flow was achieved at rotational speed $f_2$ with removal of the sacrificial valve. In embodiments of the platforms of the invention comprising capillary valve 111 at a position between capillary 110 and 112 shown in FIG. 2B, capillary 110 filled along with filling of blood fluid chamber 104 until blood reached capillary junction 111 at the junction between capillary 110 and capillary 112; in such embodiments, the capillary junction had a depth of about 0.05 cm. At a third rotational speed $f_3$ of about 500 rpm, the fluid contained in blood fluid chamber 104 was delivered into assay chamber 107 (FIG. 2B). Blood flowing into assay chamber 107 was preferentially directed to depression 113 in the assay chamber; the dimensions of depression 113 are conveniently chosen to be able to contain substantially all of the blood fluid of the sample metered through metering chamber 102 into assay chamber 107 (FIG. 2C). Displaced air flows through air channel 114, and was vented to the surface of the disc.

Figure 2D:
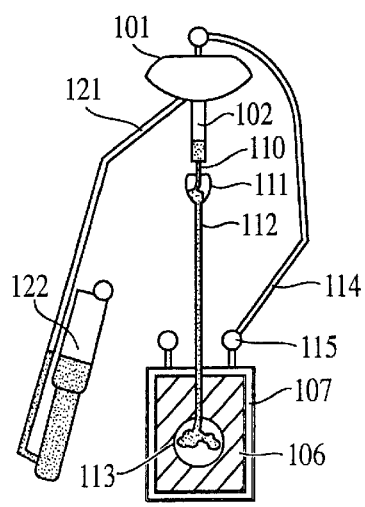
Figure 2E:
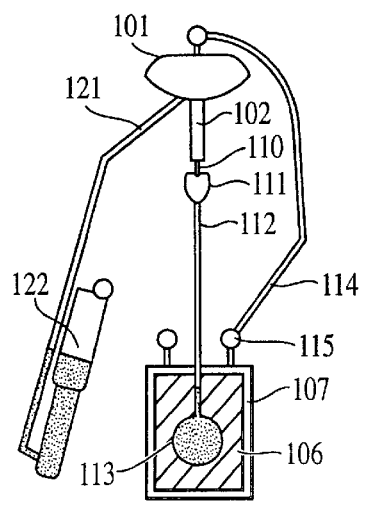

As blood flowed into depression 113, the fluid component of the blood is driven by pressure and hydrophilic forces into matrix 106, comprising a positively-charged nylon matrix having a pore size of about 0.8 μm; this pore size was chosen to prevent the cellular components of the blood from entering the matrix (FIG. 2D). The cellular blood components were retained in depression 113 and the fluid component was efficiently distributed into matrix 106. As the fluid component of the blood entered matrix 106, dried reagents 108 were solubilized and the reaction of the blood component catalyzed by said reagents proceeded. This reaction(s) went to completion within about 1 min. Reaction of the blood component(s) with reagents 108 produce colored product 109 which was then detected (FIG. 2E), as described below in Example 4.

EXAMPLE 2

Glycated Hemoglobin Assay—Fluidics Structure

A microsystems platform provided by the invention and specifically designed for performing a glycated hemoglobin assay is illustrated in FIG. 11.

Construction of the disk embodiments of the platforms of the invention are as described in Example 1. The blood application and metering components and their dimensions and relationships to one another are identical to those described above, comprising sample entry port chamber 901, metering capillary 902, overflow capillary 903, metered blood fluid chamber 904 and overflow chamber 905. As in Example 1, each of the overflow and fluid chambers is also connected with air ports or air channels, such as 914, and capillary junction(s) 915, that permit venting of air displaced by fluid movement on the platform.

Blood fluid chamber 904 was fluidly connected to capillary 910 that was about 0.25 mm deep and had a cross-sectional diameter of about 0.25 mm and was connected to sacrificial valve 911. Sacrificial valve 911 was further fluidly connected with capillary 912 that was about 0.25 mm deep and had a cross-sectional diameter of about 0.25 mm. Capillary 912 was further fluidly connected to mixing chamber 915 that was about 0.25 cm deep, had a cross-sectional diameter of about 1 cm, and was positioned about 2.5 cm from the center of rotation. Lysis buffer was loaded directly onto mixing chamber 915 in this embodiment and did not use capillary 918 or lysis buffer chamber 916 as shown in the Figure. 45 μL of lysis buffer was applied to the mixing chamber as a solution of 0.1% Triton X100 in 50 mM Tris pH 9.5.

Mixing chamber 915 was fluidly connected to capillary 917 that was about 0.25 mm deep and had a cross-sectional diameter of about 0.25 mm, and was connected to secondary metering structure 919. Secondary metering structure 919 was about 0.1 cm deep and was positioned about 3.5 cm from the center of rotation. Secondary metering structure 919 was constructed to comprise two sections. A metering section was arranged proximal to the entry position of capillary 917 and was separated from an overflow section by a septum that extended from the distal wall of the structure to a position just short of the proximal wall of the structure. This arrangement produced a fluid connection between the first metering section having a volumetric capacity of about 6.4 μL and the overflow section having an excess volumetric capacity of 90 μL. The volumetric capacity of the overflow section was sufficient to accommodate the largest blood fluid volume applied to the disk.

Capillary 921 was in fluid connection with secondary metering structure 919 at the distal wall of the metering section. Capillary 921 was about 0.15 cm deep and had a cross-sectional diameter of about 0.05 cm and was connected to boronate affinity matrix chamber 922. Boronate affinity matrix chamber 922 was about 0.15 cm deep, had a cross-sectional diameter of about 0.3 cm and was positioned about 4.8 cm from the axis of rotation. Boronate affinity matrix chamber 922 was filled with boronate-functionalized agarose beads having a mean diameter of about 60 μm; the beads were maintained in the chamber 922 using a porous frit 927. Fluid flow through capillary 921 was connected to capillary or sacrificial valve 923. Boronate affinity matrix chamber 922 was further comprised of a translucent window that permitted reflective spectrophotometry of the contents of the chamber.

Boronate affinity matrix chamber 922 was further fluidly connected to capillary 928. Capillary 928 was about 0.25 mm deep and had a cross-sectional diameter of about 0.25 mm and was connected to column wash buffer reservoir 929. Column wash buffer reservoir 929 was about 0.25 cm deep and had a cross-sectional diameter of about 2 cm and was positioned about 3.6 cm from the axis of rotation, more proximal to the axis of rotation than boronate affinity matrix chamber 922. Column wash buffer reservoir 929 comprises 290 µL of column preparation buffer that was a solution of magnesium chloride, taurine, D,L-methionine, sodium hydroxide, antibiotics and stabilizers constituted according to the manufacturer's instructions (Isolab Inc. #SG-6220). Fluid flow through capillary 928 was connected to capillary or sacrificial valve 936.

Boronate affinity matrix chamber 922 was further fluidly connected to capillary 932. Capillary 932 was about 0.5 m deep and had a cross-sectional diameter of about 0.5 mm and was connected to non-glycated hemoglobin read chamber 934. Chamber 934 was about 0.25 cm deep and had a cross-sectional diameter of about 2 cm and was positioned about 5 cm from the axis of rotation and was further comprised of a translucent window that permitted reflective spectrophotometry of the contents of the chamber at 430 nm.

As illustrated in FIG. 11, in the use of this platform about a 6.4 µL volume of blood was applied to blood fluid chamber 904, either directly or using the metering components of the platform described above. Blood flowing through capillary 910 and lysis buffer contained in mixing chamber 915 were mixed in the mixing chamber. A 45 µL volume of lysis buffer was mixed with the blood sample. Fluid flow within mixing chamber 915 was turbulent, in contrast to fluid flow through capillaries 910 or 918, which was primarily laminar, so that mixing occurred predominantly in mixing chamber 915. Fluid flow proceeded through channel 917 and into secondary metering structure 919. The mixture of lysis buffer and blood, comprising a lysed blood sample 941, flowed at a rotational speed $f_2$ of about 750 rpm into secondary metering structure 919 with release of a sacrificial valve 953. Lysed blood sample 941 entered and filled the metering section of secondary metering structure 919. Any additional lysed blood sample then emptied into the overflow chamber of secondary metering structure 919 and filled the total hemoglobin read chamber. Most preferably, a sufficient volume of lysis buffer and blood sample was applied to the disc to fill at least the metering sections of secondary metering structure 919 and the total hemoglobin read chamber.

After the lysed blood sample 941 was completely transferred to secondary metering structure 919, capillary or sacrificial valve 923 was released, allowing the metered lysed blood sample from the metering section of secondary metering structure 919 through capillary 921 and into boronate affinity matrix 922. Capillary or sacrificial valve 936 was then released, allowing about 290 µL of column wash buffer 943 to flow at rotational speed $f_2$ through capillary 930 and into boronate affinity matrix 922. Continued or discontinuous rotation motivates column preparation buffer through boronate affinity matrix 922 and into non-glycated hemoglobin read chamber 934. The control sample read cuvettes 8– and 8~ were then then illuminated by light at a wavelength of 430 nm and the blank reading, i.e. reflectance from cuvettes containing only buffer, was determined. The non-glycated hemoglobin read window was then illuminated by light at a wavelength of 430 nm and the concentration of non-glycated hemoglobin in the sample that has eluted from the column was determined by reflectance spectroscopy. The total hemoglobin read window was also illuminated by light at a wavelength of 430 nm and the concentration of total hemoglobin in the lysed sample was determined by reflectance spectroscopy.

The relative amount of non-glycated hemoglobin in the sample is determined by dividing the amount of hemoglobin obtained by illuminating the eluted fraction by the amount of hemoglobin obtained in the total fraction.

EXAMPLE 3

Combination Glucose Concentration—Glycated Hemoglobin Assay Platform

A Microsystems platform provided by the invention and specifically designed for performing both a determination of blood glucose concentration and a glycated hemoglobin assay is illustrated in FIGS. 12A through 12Q and 13A through 13E.

Construction of the disk embodiments of the platforms of the invention were as described above. FIG. 13B shows a detailed description of the microfluidics components of the platform, which are described in additional detail below. FIG. 13C shows the geometry of a screen printed electrical lead layer deposited on a mylar substrate. FIG. 13D shows the positions of screen printed heaters activated by the electrical leads of the lead layer and screen printed on mylar. FIG. 13E shows a overlay of these components in the assembled disc.

Referring to the microfluidics components of the platform shown in FIG. 13B, an entry port 1 is positioned on the top surface of the disc and is open for the user to apply an unmetered sample. Entry port 1 is about 0.32 cm deep, has a cross-sectional diameter of about 1 cm, is positioned about 2 cm from the center of rotation, and is fluidly connected to capillary channel 1A that is about '1 mm deep and has a cross-sectional diameter of about 1 mm. Capillary channel 1A is fluidly connected to metering component 2, which comprises four sections. The first section is rectangularly-shaped and extends in a direction proximal to the axis of rotation away from its fluid connection with capillary channel 1A. About half way up this rectangular section is a lateral chamber 3, which empties into a blood glucose metering chamber 4 and-an overflow chamber 5. The first section of the metering component is about 0.1 cm deep, has a cross-sectional diameter of about 0.4 cm, is positioned about 2.2 cm from the center of rotation, and has a volumetric capacity of about 5 microliters for Hb assay. The lateral chamber 3 is 1 mm deep, has a cross-sectional diameter of 1 mm, and is positioned 2.3 cm from the center of rotation. Blood glucose metering chamber 4 is 1 mm deep, has a cross-sectional diameter of 4.5 mm, is positioned 2.6 cm from the center of rotation and has a volumetric capacity of 16 µL. Overflow chamber 5 is 1 mm deep, has a cross-sectional diameter of 2 mm, is positioned 2.6 cm from the center of rotation and has a volumetric capacity of 7 µL.

Overflow chamber 5 is fluidly connected to overflow channel 8 that is 0.75 mm deep, has a cross-sectional diameter of 0.75 mm and extends 3.8 cm from overflow chamber 5. Overflow channel 5 is fluidly connected to short sample detection cuvette 9 that is two depths: 0.25 mm and 2.2 mm(inner) deep, has a cross-sectional diameter of 2.5 mm, is positioned 4–5.8 cm from the center of rotation and has a volumetric capacity of 50 µL.

Blood glucose metering chamber 4 is fluidly connected to capillary 15 that is about 0.25 mm deep, has a cross-sectional diameter of about 0.25 mm and extends about 0.1 cm from blood glucose metering chamber 4. Capillary 15 is connected to sacrificial wax valve 6, which is further fluidly connected with wax recrystallization chamber 6A that is about 0.5 mm deep and has a volumetric capacity sufficient to sequester melted wax from a released wax valve and prevent occlusion of the lumen of the capillary 15 controlled by the valve. Capillary 15 is further fluidly connected with glucose assay chamber 11 that is about 0.1 cm deep, has a cross-sectional diameter of about 0.5 mm, is positioned about 5 cm from the center of rotation and has a volumetric capacity of about 10 µL. Glucose assay chamber 11 comprises a depression 11A in the surface of the platform having a depth of about 0.1 cm, most preferably comprising a circular or rectangular depression connected to capillary 15 so that blood flows into the chamber through the bottom of depression 11A. Depression 11A is constructed to have a volumetric capacity of from half to twice the assay volume. Blood glucose assay chamber 11 also comprises a pad or matrix 10 of a positively-charged nylon matrix having a pore size of about 0.8 μm. The upper limit on pore size of matrix 10 is chosen to inhibit or prevent blood cell entry into the matrix. The matrix is positioned in blood glucose assay chamber 11 to be in fluidic contact with depression 11A, more preferably covering depression 11A, and most preferably having a surface area greater than the surface area of depression 11A. The matrix was further impregnated with immobilized reagents 11B which produce a detectable product proportional to the amount-or concentration of glucose in a blood sample. Most preferably, the detectable product is a colored product 11C, i.e., a product absorbing light at a detectable, most preferably a visible, wavelength.

Lysis metering chamber 2 is fluidly connected to capillary 7 controlled by sacrificial valve 7A. Sacrificial wax valve 7A is further fluidly connected with wax recrystallization chamber 7B that is 1 mm deep and has a volumetric capacity sufficient to sequester melted wax from a released wax valve and prevent occlusion of the lumen of the capillary 7 controlled by the valve. Capillary 7 is 0.25 mm deep, has a cross-sectional diameter of 0.25 mm, extends 0.1 cm from lysis metering chamber 2 and is fluidly connected to blood lysis chamber 16. Blood lysis is contained within the mixing chamber Blood lysis chamber 16 is 2.3 mm deep, has a cross-sectional diameter of 1 cm, is positioned 3 cm from the center of rotation, and contains 45 μL of blood lysis solution (0.1% Triton-X100 in 50 mM Tris, pH 9.5).

Blood lysis chamber 16 is fluidly connected at a distal aspect to capillary 17 controlled by sacrificial valve 18. Capillary 17 is about 0.25 mm deep and has a cross-sectional diameter of about 0.25 mm Sacrificial wax valve 18 is further fluidly connected with wax recrystallization chamber 18A that is about 0.5 mm deep and has a volumetric capacity sufficient to sequester melted wax from a released wax valve and prevent occlusion of the lumen of the capillary 17 controlled by the valve. Capillary 17 is fluidly connected to secondary metering structure 19. Secondary metering structure 19 is 1.5 mm deep, and is positioned 3.8 cm from the center of rotation. Secondary metering structure 19 is constructed to comprise three sections. A first section 20 comprises a throwaway section that is used to discard the first sample and taking the second sample to provide a better sample for analysis, having a volumetric capacity of about 6.4 μL. Throw away section 20 is arranged proximal to the entry position of capillary 17 and is separated from a metering section 21 by a septum that extends from the distal wall of the structure to a position just short of the proximal wall of the structure. This arrangement produces a fluid connection between throwaway section 20: and the metering section 21. Metering section has a volumetric capacity of about 6.4 μL and is fluidly connected to an overflow section 24 having an excess volumetric capacity of about 90 μL. The volumetric capacity of the overflow section is sufficient to accommodate the largest blood fluid volume applied to the disk.

Capillary 25 is in fluid connection with secondary metering structure 21 at the distal wall of the metering section. Capillary 25 is about 0.15 cm deep and has a cross-sectional diameter of about 0.5 mm and is connected to boronate affinity matrix chamber 28. Capillary 25 is fluidly connected to sacrificial wax valve 26 that is further fluidly connected with wax recrystallization chamber 26A Wax recrystallization chamber 26A is about 0.3 cm deep and has a volumetric capacity sufficient to sequester melted wax from a released wax valve and prevent occlusion of the lumen of the capillary 25 controlled by the valve.

Boronate affinity matrix chamber 28 is about 0.15 cm deep, has a cross-sectional diameter of about 0.3 cm and is positioned about 4.8 cm from the axis of rotation. Boronate affinity matrix chamber 28 is filled with boronate-functionalized agarose beads (Isolab, $SG-6220) having a mean diameter of about 60 μm; the beads are maintained in the chamber 28 using a porous frits 29. Boronate affinity matrix chamber 28 is further fluidly connected to capillary 31. Capillary 31 is about 0.25 mm deep and has a cross-sectional diameter of about 0.25 mm and is connected to column wash buffer reservoir 30. Column wash buffer reservoir 30 is about 0.25 cm deep and has a cross-sectional diameter of about 2 cm and is positioned about 3.6 cm from the axis of rotation, more proximal than boronate affinity matrix chamber 28. Column wash buffer reservoir 30 comprises about 290 μL of column wash buffer comprising a solution of asparagine, magnesium chloride, taurine and D,L-methionine (Isolab, #SG-6220). Fluid flow through capillary 31 is connected to sacrificial valve 32. Sacrificial wax valve 32 is further fluidly connected with wax recrystallization chamber 32A that is about 0.5 mm deep and has a volumetric capacity sufficient to sequester melted wax from a released wax valve and prevent occlusion of the lumen of the capillary 32 controlled by the valve.

Boronate affinity matrix chamber 28 is further fluidly connected to capillary 37. Capillary 37 is about 0.5 mm deep and has a cross-sectional diameter of about 0.5 mm and is connected to sample collection cuvette array 12. Sample collection cuvette array 12 is about 0.25 cm deep and has a cross-sectional diameter of about 2.1 cm and is positioned about 5 cm from the axis of rotation. Sample collection cuvette array 12 is separated into a multiplicity of individual chambers, each separated from one another by septa that extend from the distal wall of the cuvettes to a position adjacent to the proximal wall of the cuvettes, so that a fluid passage 50 is maintained between each of the cuvettes. The fluid passage 50 is formed by the back (proximal wall) of the sample collection cuvette array 12 and the row of septa separating each of the sections of the sample collection cuvettes 12. Capillary 37 is fluidly connected to sample collection cuvette array 12 at a position adjacent to the proximal wall of the array and directed to the cuvette most proximal to the boronate affinity matrix chamber 28.

Capillary 22 is fluidly connected to secondary metering structure 19. Capillary 22 is about 0.25 mm deep and has a cross-sectional diameter of about 0.25 mm and is connected to secondary metering structure 19 at a position between the metering section and the overflow section. Capillary 22 is further fluidly connected with total hemoglobin read chamber 23. Total hemoglobin read chamber 23 is about 0.25 cm deep, is positioned about 5 cm from the center of rotation, and has a volumetric capacity of about 50 μL. Total hemoglobin read chamber 23 is positioned radially more distal from the center of rotation than secondary metering structure 19, and comprises a read window translucent to light having a wavelength of 300–1000 nm. In addition, there is no capillary or sacrificial valving controlling fluid flow in capillary 23.

The platform also comprises control sample read cuvettes 13 and 14, advantageously positioned in proximity to total hemoglobin read chamber 23. Control sample read cuvettes 13 and 14 are each about 0.25 cm deep, positioned about 5 cm from the center of rotation, and have a volumetric capacity of about 50 μL. Control sample read cuvettes 13 and 14 comprise a read window translucent to light having a wavelength of 410 nm. Control sample read cuvettes 13 and 14 are not fluidly connected to any other structure on the platform.

Air displacement channels 33 and capillary junction(s) 34, that permit venting of air displaced by fluid movement on the platform, are fluidly connected to the components of the platform to permit unimpeded fluid flow.

As illustrated in FIGS. 12A through 12Q, in the use of this platform a volume of blood about 30 µL is applied to entry port 1. Blood enters lysis subvolume 2 and lateral passageway 3 under the influence of gravity and capillary forces in the absence of rotation of the platform, as shown in FIG. 12A. Upon rotation of the platform at a first rotational speed $f_1$ of 400–600 rpm, blood completely fills lysis subvolume 2 and also flows through passageway 3 and into blood glucose metering chamber 4 and overflow chamber 5, shown in FIG. 12B. Blood is retained in blood glucose chamber 4 either due to capillary pressure or by a sacrificial valve 6, most preferably a wax valve. Similarly, blood is retained in blood lysis subvolume 2 by a valve, most preferably a sacrificial valve 7. Excess blood flows at rotational speed $f_1$ through overflow channel 8 and into overflow chamber 9, shown in FIGS. 12C and 12D. Typical values for the first rotational speed are an acceleration of about 20 to 60 rpm/sec to a final radial velocity of about 600 rpm.

After blood is metered and excess blood delivered to overflow chamber 9, the rotational speed of the disc is reduced to a rotational speed $f_{1a}$ of 600 to 100 rpm, typically 60 rpm, to perform a blanking measurement on sample collection cuvette array 12, total hemoglobin read chamber 23 and blood glucose assay chamber 11. Measurements of blanking cuvettes 13 and 14 are also advantageously performed.

The disc is then accelerated to a second rotational speed $f_2$ greater than $f_1$, and typically in the range of 800 rpm to about 1000 rpm. At this speed, capillary valve 6 is overcome or sacrificial valve 6 is released, and about 16 µL of blood from blood glucose metering chamber 4 flows through capillary 15 and into blood glucose assay chamber 11, shown in FIG. 12E. Upon entering assay chamber 11, blood fluid components are forced into absorbent matrix 10 through depression 11A. The blood fluid is incubated in matrix 10 for a time sufficient for the reagents 10A to produce a colored product 10B in an amount proportional to the amount of glucose in the blood fluid sample.

The disc is slowed, typically to a rotational speed $f_4$ of about 100 rpm, for glucose data acquisition using reflectance spectrometry; data acquisition as the disc is spinning down also enables to instrument to set t=0 for the assay, based on a decrease in reflectance when the matrix 10 is wet by the blood fluid components and hence the matrix's scattering decreases. Development of colored product 10B is shown in FIG. 12G.

The disc is then accelerated to rotational speed $f_3$ of about 1000 rpm, with release of sacrificial valve 7A and fluid flow of about 5–6.4 µL of blood from metered subvolume 2 through capillary 7 and into blood lysis chamber 16 containing about 40 µL of blood lysis buffer. This is shown in FIG. 12H. The mixture of blood and blood lysis buffer in blood lysis chamber 16 is mixed by agitation, wherein the platform is accelerated repeatedly +250 rpm/sec to −250 rpm/sec (wherein "+" and "−" indicate acceleration in different directions), typically 250–500 rpm/sec, over a time period of about 2 min, typically 1–3 min, as shown in FIGS. 12I and 12J.

The disc then is accelerated to a rotational speed $f_5$ of 1000 rpm and sacrificial valve 18 is released. Lysed blood from blood lysis chamber 16 flows through capillary 17 and into secondary metering structure 19, as shown in FIG. 12K.

The lysed blood solution sequentially fills throwaway section 20, which is used as a trap for cell debris, metering section 21 and excess lysed blood then fills overflow section 24. Filling of metering chamber 21 is immediately followed by fluid flow through capillary 22 and filling of total hemoglobin read chamber 23. The disc is spun at rotational speed $f_5$ for a time sufficient to substantially completely drain blood lysis chamber 16. The configuration of the blood fluids on the disc after this spin is shown in FIG. 12L.

The disc is then decelerated to a rotational speed of 750 rpm, and sacrificial valve 26 is released. A metered volume of about 6.4 µL of lysed blood from metering section 21 flows through capillary 27 and into boronate affinity matrix chamber 28 (shown in FIG. 12M). The lysed blood solution is allowed to incubate in the chamber for a time of about 1 min, sufficient for glycated hemoglobin to bind to the matrix. This aspect of the disc is illustrated in FIG. 12N.

The disc is then accelerated to a rotational speed of 1000 rpm, and sacrificial valve 32 is released. A volume of about 290 µL of column wash buffer (Isolab #SG-6220) flows from wash buffer reservoir 30 though capillary 31 and into boronate affinity matrix chamber 28 (shown in FIG. 12O). The wash buffer displaces the non-glycated hemoglobin and other components of the lysed blood fluid from the affinity column matrix and into sample collection cuvette array 12. FIGS. 12P through 12Q show sequential filling of the individual cuvettes in sample collection cuvette array 12. The rotation speed of the disc is reduced, to 60 rpm for sample collection cuvette array 12 and total hemoglobin read chamber 23 to be interrogated spectrophotometrically. The glycated fraction of the blood sample is determine algorithmically by subtracting the non-glycated hemoglobin fraction in sample collection cuvette array 12 from-the total hemoglobin detected in total hemoglobin read chamber 23.

EXAMPLE 4

Blood Glucose Assay—Chemistries

Microsystems platforms as provided by the invention were used to perform blood glucose and glycated hemoglobin assays as described herein.

Blood Glucose Assay

A series of blood glucose assays were performed to determine the precision of repeated glucose assays using the microsystems platforms of the invention.

The assays were performed on a microsystems platform according to Example 3 using a round reagent cuvette (113). 60–70 µL of human whole blood was applied to the disk, and 15 µL metered into the metering capillary. A glucose reagent pad obtained from LifeScan was used for performing the glucose determination. Optical absorbance readings were obtained at 430 nm, 590 nm and 660 nm on the unreacted reagent pad as a control. Blood was released into the reaction chamber and optical data gathered at one-second intervals for about 1 min. Absorbance at 590 nm was specific for the amount of glucose in the sample; absorbance at 430 nm was specific for hemoglobin in the sample; and absorbance at 660 nm was used to detect non-specific background absorbance, as described above.

A total of seven assays were performed for each of two samples and the amount of glucose (in mg/dL) determined as follows:

|  | Sample 1 | Sample 2 |
| --- | --- | --- |
| Glucose mg/dL | 136.0 | 113.2 |
| % CV | 4.4% | 4.5% |

These assays were repeated as above using a microsystems platform according to Example 1 comprising a rectangular reagent cuvette (113). A Biodyne-B membrane (Pall) was impregnated with glucose oxidase reagents as described above and used for performing the glucose determination. In these embodiments, chamber 113 had dimensions of 4 mm×5 mm.

The glucose determination was performed exactly as described in the first series of experiments. Standard blood glucose assays were run on these samples in parallel to compare the results obtained with the microsystems platforms of the invention with conventional assays. These results were as follows:

| mg/dL Reference Method | mg/dL Invention |
| --- | --- |
| 46.8 | 61.9 |
| 85.9 | 76.8 |
| 107.0 | 115.8 |
| 149.0 | 144.2 |

These results established that the microsystems platforms of the invention were capable of determining blood glucose concentrations.

Correction for Interfering Substances

In addition, assays were performed on a microsystems platform to Example 3 using a round reagent cuvette (113) and the glucose results obtained were corrected for hemoglobin interferences as discussed herein. In these experiments, the spectrophotometric results obtained were used to calculate blood glucose with and without correction for the hemoglobin absorbance signal at 590 nm. The correction factor was determined empirically using samples comprised of phosphate buffered saline to which known qualities of glucose and/or hemoglobin were added. The resulting samples were assayed on the microsystems platform according to Example 3 using a round reagent cuvette (113) to give the following data:

| Sample | Glucose Concentration (mg/dL) | Hemoglobin Concentration (mg/dL) | Reflectance (590 nm) | Reflectance (430 nm) |
| --- | --- | --- | --- | --- |
| A | 0 | 0 | 0.0152 | −0.0204 |
| B | 0 | 1.25 | 0.2116 | 0.3041 |
| C | 75 | 5 | 1.2767 | 0.3452 |
| D | 78 | 0 | 0.9576 | 0.1311 |

Figure 14A:
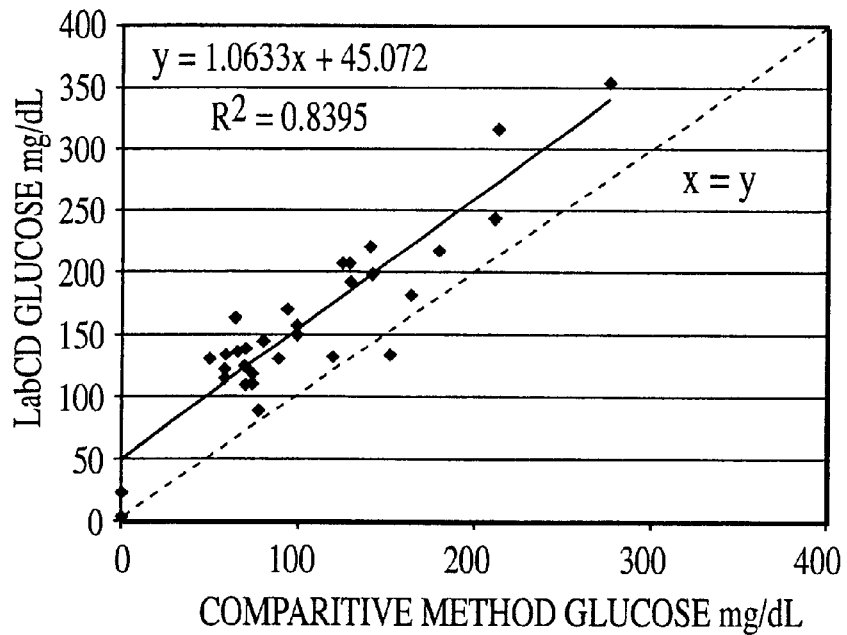
FIGS. 14A and 14B illustrate the results of the assays disclosed in Example 4.
Figure 14B:
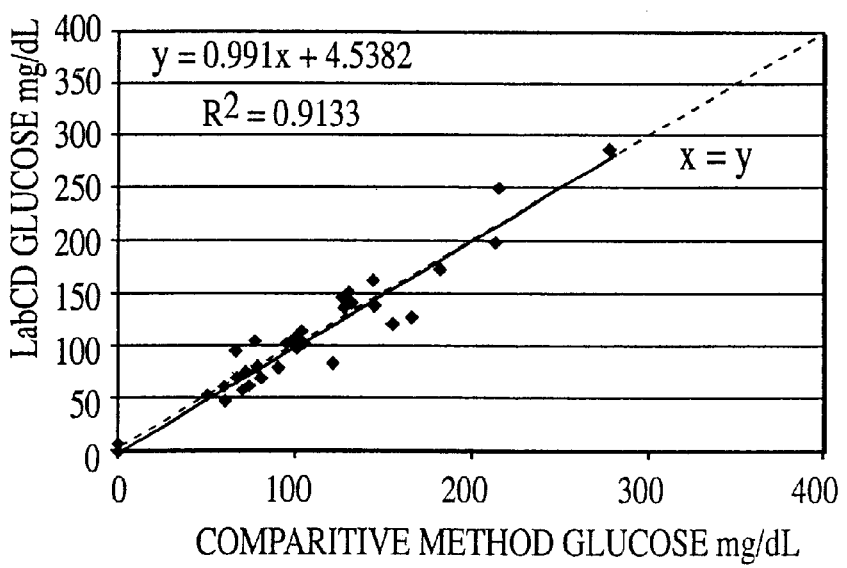

For glucose chromagen alone, Sample D, the Reflectance (430 nm) is 16.1% of the Reflectance(590 nm) [(0.131−(−0.0204))/(0.9576−0.152)]. For hemoglobin alone, Sample B, the Reflectance(590 nm) is 60.5% of the Reflectance(430) [(0.2116−0.0152)/(0.3041−(−0.0204))]. For the combination of glucose and hemoglobin, Sample C, the Reflectance (430nm) is the sum of the Reflectance (430 nm) due to the hemoglobin plus 16.1% of the Reflectance(590 nm) due to the glucose chromagen; similarly, the Reflectance(590 nm) is the sum of the Reflectance(590 nm) due to the glucose chromagen plus 60.5% of the Reflectance(430 nm) due to the hemoglobin. Using standard algebraic methods, the factor to be used was calculated to be:

The results shown in FIGS. 14A and 14B illustrate the difference in the accuracy of the data obtained with and without correcting for the hemoglobin absorbance signal.

Glycated Hemoglobin Assay

A series of glycated hemoglobin assays were performed to determine the precision of repeated binding of glycated hemoglobin by measuring the amount of hemoglobin put on a phenyl boronate column and the amount of (non-glycated) hemoglobin that could be eluted from the column.

These experiments were performed using a Microsystems platform of the invention as disclosed in Example 3; the phenyl boronate column material was from a kit obtained from IsoLab Glyc-Affin GHb. 60–70 μL of human whole blood was applied to the disk, and 5 μL metered into and mixed with 45 μL of lysis buffer in the mixing chamber of the platform. 5 μL of the lysed blood was metered onto the phenyl boronate column and non-glycated hemoglobin eluted with 290 μL of elution buffer. The reflective absorbance of the lysed blood and the eluted non-glycated hemoglobin was determined spectrophotometrically at 430 nm and used to calculate the amount of non-glycated hemoglobin in the sample.

Seven separate assays were performed on each of 2 different whole blood samples. These results are as follows:

|  | Sample 1 | Sample 2 |
| --- | --- | --- |
| % NGHb, reference method | 93 | 90 |
| % NGHb, invention | 93 | 92 |
| % CV | 1.2% | 1.7% |

DNA Binding Assays

These experiments were performed to show that the Microsystems platforms of the invention could efficiently isolate plasmid DNA from a sample. In these experiments, diatomeceous earth was used to specifically bind plasmid DNA, and the results were compared with a standard plasmid DNA extraction kit (Qiagen).

In these experiments, the Qiagen assay was performed until the bacterial culture had been disrupted with chaotropic salts. At this point, the solution was split in half, and one half assayed using the Qiagen reagents and columns, and the other half 300 μL assayed using a microsystem platform adapted from the one described in Example 2. In this embodiment, the diatomeceous earth column was loaded onto the platform and the sample applied thereto by centrifugation at about 800 rpm. The column was washed twice with 100 μL of Qiagen buffer PE at about 850 rpm, and the plasmid DNA was then eluted twice, with 50 μL of Qiagen Buffer EB, once at 600 rpm and again at at 900 rpm. The eluted plasmid DNA from each preparation was precipitated by the addition of ice cold ethanol to 70% and the DNA pellet collected by centrifugation and resuspended in 50 μL of 10 mM Tris-HCl, pH 8. 15 μL were analyzed by conventional agarose gel electrophoresis, stained with ethidium bromide and osverved under ultraviolet light illumination.

The results of these assays are shown in FIG. 15, and illustrate the use of the microsystems platforms of the invention for isolating plasmid DNA from a biological fluid sample.

It should be understood that the foregoing disclosure emphasizes certain specific embodiments of the invention and that all modifications or alternatives equivalent thereto are within the spirit and scope of the invention as set forth in the appended claims.

What is claimed is:

1. A microsystem platform for performing an assay to detect an analyte in a fluid sample, comprising:
   a) a rotatable platform, comprising a substrate having a first flat, planar surface and a second flat, planar surface opposite thereto, each surface comprising a center about which the platform is rotated, wherein the first surface comprises in combination
   b) an entry port comprising a depression in the first surface having a volumetric capacity of about 1 to about 150 µL, that is fluidly connected with
   c) a capillary microchannel having a cross-sectional diameter of less than 800 microns, that is further fluidly connected with
   d) an assay chamber fluidly connected with the entry port, the assay chamber further comprising
      i) a porous matrix comprising reagents for performing an analyte detection assay, wherein the porous matrix has an average pore size that prevents cells from entering the matrix; and
   wherein a fluid sample applied to the entry port is delivered to the assay chamber through the capillary microchannel by rotation of the platform, and wherein delivery of the fluid sample to the assay chamber initiates the analyte detection assay.

2. The microsystem platform of claim 1 wherein the entry port is fluidly connected with
   e) an entry passageway having a cross-sectional diameter of about 0.1 mm to about 5 mm that is fluidly connected with
   f) a fluid entry chamber comprising a fluid metering volume and an overflow passageway, wherein the overflow passageway is further connected to an overflow capillary, wherein the overflow capillary is further fluidly connected to
   g) an overflow chamber comprising a first shallow outer portion having a depth from about 0.05 mm to about 0.5 mm and an inner portion having a depth of from about 0.1 mm to 5 mm;
   wherein the overflow capillary is fluidly connected with the overflow chamber at a position on the platform that is at least 20% farther from the center of rotation that the fluid metering volume, and wherein the overflow and fluid chambers also comprise air displacement channels whereby air displaced by fluid movement is vented from the platform.

3. The microsystem platform of claim 1 further comprising
   e) a metering capillary and an overflow capillary, each being fluidly connected with the entry port, wherein each capillary defines a cross-sectional area of about 0.02 mm to about 800 microns in diameter, and wherein each capillary extends radially from the center of the platform and defines a first end proximally arrayed towards the center of the platform and a second end distally arrayed from the center of the platform, wherein the proximal end of each capillary defines a curved opening; wherein the metering capillary defines a volume of the fluid and wherein the metering capillary is fluidly connected with the assay chamber and wherein the overflow capillary is fluidly connected with
   f) an overflow chamber having a depth equal to or greater than the overflow capillary depth and positioned radially more distant from the center of the platform than the assay chamber and the entry port,
   wherein a capillary junction is formed at the junction of the metering capillary and the assay chamber and at the junction of the overflow capillary and the overflow chamber, whereby fluid in the entry port flows by capillary action to the junction of the metering capillary and the assay chamber, and excess fluid flows by capillary action to the junction of the overflow capillary and the overflow chamber; and wherein rotation of the platform at a first rotation speed motivates fluid displacement in the overflow capillary into the overflow chamber but not fluid displacement in the metering capillary, whereby rotation of the platform at a first rotational speed drains the fluid from the entry port into the overflow chamber; and wherein rotation of the platform at a second rotational speed that is greater than the first rotational speed motivates fluid displacement of the volume of the fluid in the metering capillary into the assay chamber; and wherein each of the assay chamber and overflow chamber also comprise air displacement channels whereby air displaced by fluid movement is vented from the platform.

4. The microsystem platform of claim 3, wherein the porous matrix comprises a hydrophilic matrix.

5. The microsystem platform of claim 4, wherein said analyte detection assay is a glucose detection assay.

6. The microsystem platform of claim 3, further comprising
   g) a sacrificial valve between the metering capillary and the assay chamber, wherein release of the sacrificial valve permits fluid flow from the metering capillary to the assay chamber at a non-zero rotational speed.

7. The microsystem platform of claim 6 wherein the sacrificial valve is a solid, semi-solid or viscous liquid hydrocarbon, or a plastic.

8. The microsystem platform of claim 7 further comprising a heating element in the platform in thermal contact with the sacrificial valve, wherein heating the heating element releases the sacrificial valve.

9. The microsystem platform of claim 3, wherein the assay chamber has a top and bottom surface and the chamber further comprises
   e) a depression in the bottom surface of the assay chamber having a volumetric capacity about equal to the volume contained in the metering capillary.

10. The microsystem platform of claim 9, wherein the top surface of the assay chamber is translucent.

11. The microsystem platform of claim 1 further comprising
    e) a read chamber fluidly connected to the assay chamber by a first microchannel, and
    f) a wash buffer reservoir containing a wash buffer and fluidly connected to the assay chamber by a second microchannel
    wherein rotation of the platform at a rotational speed greater than the rotational speed of the platform that delivers the fluid sample to the assay chamber motivates wash buffer through the second microchannel and into the assay chamber, whereby the wash buffer displaces the fluid sample from the assay chamber and into the read chamber through the first microchannel.

12. The microsystem platform of claim 11, further comprising
   g) a sacrificial valve in the second microchannel, wherein release of the sacrificial valve permits wash buffer flow from the wash buffer reservoir to the assay chamber when the platform is rotated at a non-zero rotational speed.

13. The microsystem platform of claim 12 wherein the sacrificial valve is a solid, semi-solid or viscous liquid hydrocarbon, or a plastic.

14. The microsystem platform of claim 13 further comprising a heating element in the platform in thermal contact with the sacrificial valve, wherein heating the heating element releases the sacrificial valve.

15. The microsystem platform of claim 11, wherein the read chamber comprises a top surface that is translucent.

16. The microsystem platform of claim 15, wherein the assay chamber has a top and bottom surface and the chamber further comprises
   e) a depression in the bottom surface of the assay chamber having a volumetric capacity about equal to the volume contained in the metering capillary and in fluidic contact with the second matrix element.

* * * * *

UNITED STATES PATENT AND TRADEMARK OFFICE
CERTIFICATE OF CORRECTION

PATENT NO. : 6,632,399 B1
DATED : October 14, 2003
INVENTOR(S) : Kellogg et al.

It is certified that error appears in the above-identified patent and that said Letters Patent is hereby corrected as shown below:

Drawings,
Sheets 22/38 through 30/38, please insert reference numbers in Figures 12A - 12Q.
Sheet 32/38, please insert reference numbers in Figures 13B.

Column 41,
Line 51, please delete "7" and substitute -- 7A --

Signed and Sealed this

Eleventh Day of May, 2004

JON W. DUDAS
*Acting Director of the United States Patent and Trademark Office*